United States Patent [19]

Baker et al.

[11] Patent Number: 5,389,647
[45] Date of Patent: Feb. 14, 1995

[54] RENIN INHIBITORS

[75] Inventors: William R. Baker, Libertyville; Steven A. Boyd, Mundelein; Anthony K. L. Fung, Gurnee; Herman H. Stein, Highland Park; Jon F. Denissen, McHenry; Charles W. Hutchins, Gurnee, all of Ill.

[73] Assignee: Abbott Laboratories, Abbott Park, Ill.

[21] Appl. No.: 71,747

[22] Filed: Jun. 9, 1993

Related U.S. Application Data

[60] Division of Ser. No. 736,364, Jul. 31, 1994, Pat. No. 5,244,910, and a continuation-in-part of Ser. No. 680,811, Apr. 9, 1991, Pat. No. 5,122,514, said Ser. No. 736,364, is a continuation-in-part of Ser. No. 568,557, Aug. 15, 1990, abandoned.

[51] Int. Cl.$^6$ .............. A61K 31/445; C07D 413/08; C07D 401/08
[52] U.S. Cl. .............. 514/326; 514/227.8; 514/237.8; 514/256; 514/318; 514/327; 544/60; 544/130; 544/335; 546/194; 546/209; 546/210; 546/221
[58] Field of Search .......... 544/60, 130, 335; 546/194, 209, 210, 221, 226; 514/227.8, 237.8, 256, 318, 326, 327, 330

[56] References Cited

U.S. PATENT DOCUMENTS

| | | |
|---|---|---|
| 4,895,834 | 1/1990 | Hudspeth et al. .............. 514/18 |
| 4,900,745 | 2/1990 | Hanson et al. .............. 514/400 |
| 5,055,466 | 10/1991 | Weller et al. .............. 514/235.8 |
| 5,268,374 | 12/1993 | Fung .............. 514/237.2 |

FOREIGN PATENT DOCUMENTS

WO90/03971 4/1990 WIPO .
WO90/05531 5/1990 WIPO .

*Primary Examiner*—Celia Chang
*Attorney, Agent, or Firm*—Steven R. Crowley

[57] ABSTRACT

A renin inhibiting compound of the formula:

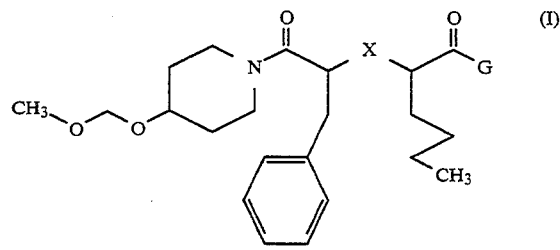

wherein X is O, NH or S and G is a mimic of the Leu-Val cleavage site of angiotensinogen; or a pharmaceutically acceptable salt, ester or prodrug thereof; with the proviso that the compound is not N-(3-(4-Morpholino)-propyl)-5(S)-(2(S)-(1(S)-(4-methoxymethoxy)piperidin-1-yl)carbonyl-2-phenyl)ethoxyhexanamido)-6-cyclohexyl-4(S)-hydroxy-2(S)-isopropylhexanamide.

6 Claims, No Drawings

RENIN INHIBITORS

This is a division of U.S. patent application Ser. No. 07,736,364, filed Jul. 31, 1991, now U.S. Pat. No. 5,244,910, which is a continuation-in-part of U.S. patent application Ser. No. 568,557, filed Aug. 15, 1990, now abandoned, which is incorporated herein by reference. This is also a continuation-in-part of U.S. patent application Ser. No. 680,811, filed Apr. 9, 1991, now U.S. Pat. No. 5,122,514, which is incorporated herein by reference.

TECHNICAL FIELD

The present invention relates to novel compounds and compositions which inhibit renin, processes for making the compounds and a method of treating hypertension or congestive heart failure, glaucoma, vascular disease, renal failure or psoriasis with a compound of the invention. In addition, the present invention relates to a method for inhibiting a retroviral protease or treating a retroviral infection with a compound of the invention.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. Renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

The renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

Inhibitors of renin have been sought as agents for control of hypertension and as diagnostic agents for identification of cases of hypertension due to renin excess.

In efforts to identify compounds which inhibit renin, compounds have been prepared which mimic angiotensinogen, the natural substrate for renin. In particular, compounds have been prepared which incorporate mimics of the dipeptide sequence of angiotensinogen preceeding the renin cleavage site (i.e., mimics of Phe-His) and which also incorporate non-cleavable mimics of the renin cleavage site of angiotensinogen (i.e., Leu-Val). Compounds comprising mimics of both portions of angiotensinogen bind to renin, but are not cleaved. Thus, renin is inhibited from acting on its natural substrate.

DISCLOSURE OF THE INVENTION

In accordance with the present invention, there are compounds of the formula:

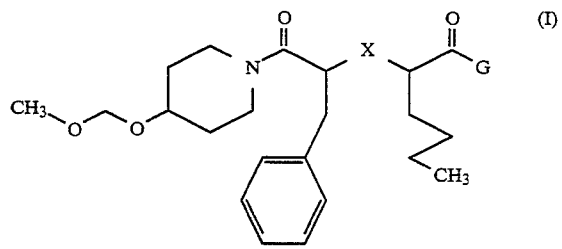

wherein X is O, NH or S and G is a mimic of the Leu-Val cleavage site of angiotensinogen; or a pharmaceutically acceptable salt, ester or prodrug thereof; with the proviso that the compound is not N-(3-(4-Morpholino)-propyl)-5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide.

Preferred compounds of the invention are compounds of the formula:

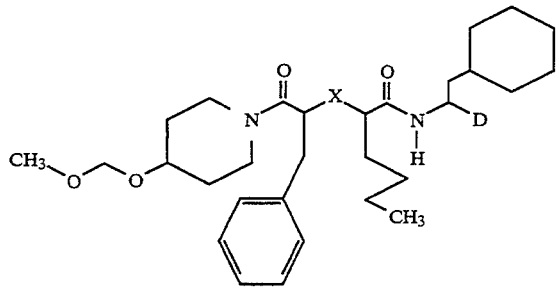

wherein X is O, NH or S; and D is

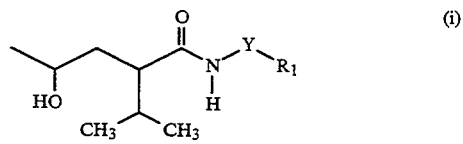

wherein Y is $C_1$ to $C_6$ alkylene or $C_1$ to $C_6$ substituted alkylene; and $R_1$ is —CN, tetrazolyl, pyridyl, pyrimidinyl, imidazolyl, thiazolyl, morpholinyl, substituted morpholinyl, thiomorpholinyl, substituted thiomorpholinyl, thiomorpholinyl dioxide, substituted thiomorpholinyl dioxide, —C(O)OR$_{24}$ wherein R$_{24}$ is hydrogen, loweralkyl or benzyl or —NHR$_2$ wherein R$_2$ is hydrogen, alkanoyl, hydroxyalkyl, an N-protecting group, —C(O)NHR$_{17}$ wherein R$_{17}$ is hydrogen or loweralkyl, —C(S)NHR$_{18}$ wherein R$_{18}$ is hydrogen or loweralkyl, —C(=N—CN)—NHR$_{19}$ wherein R$_{19}$ is hydrogen or loweralkyl, —C(=N—CN)—SR$_{22}$ wherein R$_{22}$ is loweralkyl,

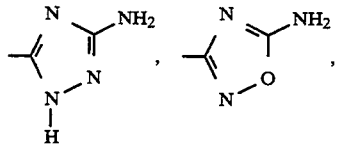

—C(O)O-benzyl, —C(O)R$_{23}$ wherein R$_{23}$ is loweralkyl, —SO$_2$NR$_{26a}$R$_{26b}$ wherein R$_{26a}$ and R$_{26b}$ are independently selected from loweralkyl or —SO$_2$R$_{27}$ wherein R$_{27}$ is loweralkyl or —Y—R$_1$ is

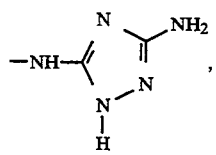

—NH$_2$, —NHC(O)NH$_2$, —NHC(S)NH$_2$, —NHSO$_2$R$_{27}$ wherein R$_{27}$ is as defined herein, —NHC(=N-CN)NHR$_{19}$ wherein R$_{19}$ is as defined herein, —NHC(=N—CN)SR$_{22}$ wherein R$_{22}$ is as defined herein or —NHSO$_2$NHR$_{26}$ wherein R$_{26}$ is as defined herein;

(ii) —CH(OH)CH(OH)CF$_2$CH$_2$N(R$_{20}$)(R$_{21}$) wherein R$_{20}$ and R$_{21}$ are independently selected from hydrogen and loweralkyl;

(iii) —CH(OH)C(O)CF$_2$CH$_2$N(R$_{20}$)(R$_{21}$) wherein R$_{20}$ and R$_{21}$ are defined as herein;

(iv) —CH(OH)CF$_2$CH$_2$N(R$_{20}$)(R$_{21}$) wherein R$_{20}$ and R$_{21}$ are defined as herein;

(v) —C(O)CF$_2$CH$_2$N(R$_{20}$)(R$_{21}$) wherein R$_{20}$ and R$_{21}$ are defined as herein;

(vi) —CH(OH)CH$_2$CH(CH(CH$_3$)$_2$)-C(O)—N=C(N(CH$_3$)$_2$)(N(CH$_3$)$_2$);

(vii) —CH(OH)CH$_2$CH(CH(CH$_3$)$_2$)CH$_2$R$_{50}$ wherein R$_{50}$ is (a) —OR$_{51}$ wherein R$_{51}$ is hydrogen, —CH$_2$OCH$_3$ or —CH$_2$OCH$_2$CH$_2$OCH$_3$, (b) —SR$_{52}$ wherein R$_{52}$ is loweralkyl, phenyl, benzyl, pyridyl, pyrimidyl, imidazolyl, loweralkyl substituted imidazolyl, piperidinyl or —R$_{54}$—O—R$_{55}$ wherein R$_{54}$ is alkylene or substituted alkylene and R$_{55}$ is —CH$_2$OCH$_3$ or —CH$_2$OCH$_2$CH$_2$OCH$_3$, (c) S(O)$_2$R$_{53}$ wherein R$_{53}$ is loweralkyl, phenyl, benzyl, pyridyl, pyrimidyl, imidazolyl, loweralkyl substituted imidazolyl, thiazolyl, loweralkyl substituted thiazolyl, piperidinyl or —R$_{54}$—O—R$_{55}$ wherein R$_{54}$ is alkylene or substituted alkylene and R$_{55}$ is —CH$_2$OCH$_3$ or —CH$_2$OCH$_2$CH$_2$OCH$_3$, (d) —N(R$_{56}$)(R$_{57}$) wherein R$_{56}$ and R$_{57}$ are independently selected from hydrogen, loweralkyl, cycloalkyl and hydroxy substituted cycloalkyl, (e)

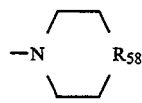

wherein R$_{58}$ is O, S, S(O)$_2$ or N(R$_{59}$) wherein R$_{59}$ is hydrogen, loweralkyl or benzyl, or (f)

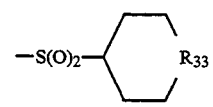

wherein R$_{33}$ is —N(R$_{34}$) wherein R$_{34}$ is hydrogen, loweralkyl or benzyl; or (viii)

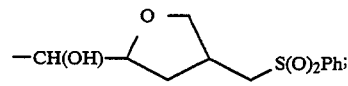

or a pharmaceutically acceptable salt, ester or prodrug thereof; with the proviso that the compound is not N-(3-(4-Morpholino)propyl)-5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide.

More preferred compounds of the invention are compounds of the formula:

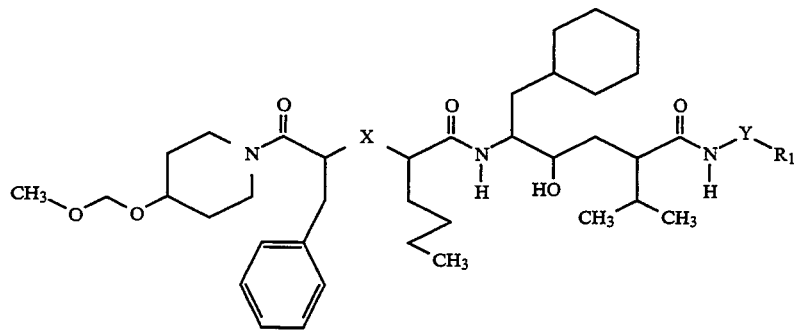

wherein X is O, NH or S; and Y is C$_1$ to C$_6$ alkylene or C$_1$ to C$_6$ substituted alkylene; and R$_1$ is —CN, tetrazolyl, pyridyl, pyrimidinyl, imidazolyl, thiazolyl, morpholinyl, substituted morpholinyl, thiomorpholinyl, substituted thiomorpholinyl, thiomorpholinyl dioxide, substituted thiomorpholinyl dioxide, —C(O)OR$_{24}$ wherein R$_{24}$ is hydrogen, loweralkyl or benzyl or —NHR$_2$ wherein R$_2$ is hydrogen, alkanoyl, hydroxyalkyl, an N-protecting group, —C(O)NHR$_{17}$ wherein R$_{17}$ is hydrogen or loweralkyl, —C(S)NHR$_{18}$ wherein R$_{18}$ is hydrogen or loweralkyl, —C(=N—CN)—NHR$_{19}$ wherein R$_{19}$ is hydrogen or loweralkyl, —C(=N—CN)—SR$_{22}$ wherein R$_{22}$ is loweralkyl,

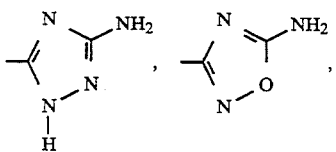

—C(O)O-benzyl, —C(O)R$_{23}$ wherein R$_{23}$ is loweralkyl, —SO$_2$NR$_{26a}$R$_{26b}$ wherein R$_{26a}$ and R$_{26b}$ are independently selected from loweralkyl or —SO$_2$R$_{27}$ wherein R$_{27}$ is loweralkyl or —Y—R$_1$ is

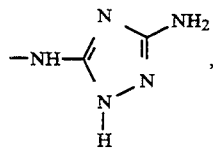

—NH$_2$, —NHC(O)NH$_2$, —NHC(S)NH$_2$, —NHSO$_2$R$_{27}$ wherein R$_{27}$ is as defined herein, —NHC(=N—CN)NHR$_{19}$ wherein R$_{19}$ is as defined herein, —NHC(=N—CN)SR$_{22}$ wherein R$_{22}$ is as defined herein or —NHSO$_2$NHR$_{26}$ wherein R$_{26}$ is as defined herein; or a pharmaceutically acceptable salt, ester or prodrug thereof; with the proviso that the compound is not N-(3-(4-Morpholino)propyl)-5(S)-(2(S)-(1(S)-(4-(methoxymethoxy)piperidin-1-yl) carbonyl-2-phenyl)ethoxyhexanamido)-6-cyclohexyl-4(S)-hydroxy-2(S)-isopropylhexanamide.

The term "mimic of the Leu-Val cleavage site of angiotensinogen" as used herein refers to the substituent G having the formula:

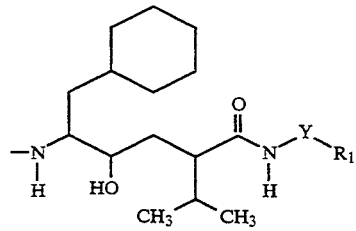

wherein Y and R$_1$ are defined as above.

The term "mimic of the Leu-Val cleavage site of angiotensinogen" as used herein also refers to the substituents corresponding to G which are disclosed in the following references:

U.S. Pat. No. 4,851,387, issued Jul. 25, 1989, which is incorporated herein by reference, discloses mimics of the Leu-Val cleavage site of angiotensinogen having the formula —N(R$_4$)CH(R$_5$)CH(OH)CH$_2$CH(R$_6$)C(O)R$_7$ wherein R$_4$, R$_5$, R$_6$ and R$_7$ are as defined therein;

European Patent Application No. EP356796, published Mar. 7, 1990, discloses mimics of the Leu-Val cleavage site of angiotensinogen having the formula —NHCH(R$_1$)CH(OR$_2$)CH(CH$_2$CHNHR$_3$)C(O)—F—R$_4$ wherein R$_1$, R$_2$, R$_3$, R$_4$ and F are as defined therein;

German Patent Application No. DE3829594, published Mar. 15, 1990, discloses mimics of the Leu-Val cleavage site of angiotensinogen having the formula —NHCH(R$_1$)CH(OH)CH$_2$CH(R$_2$)N(R$_3$)(R$_4$) wherein R$_1$, R$_2$, R$_3$ and R$_4$ are as defined therein;

U.S. Pat. No. 4,889,869, issued Dec. 26, 1989, which is incorporated herein by reference, discloses mimics of the Leu-Val cleavage site of angiotensinogen having the formula —N(R$_2$)CH(R$_3$)CH(R$_4$)CH$_2$CH(R$_5$)C(O)R$_6$ wherein R$_2$, R$_3$, R$_4$, R$_5$ and R$_6$ are as defined therein;

European Patent Application No. EP320204, published Jun. 14, 1989, discloses mimics of the Leu-Val cleavage site of angiotensinogen having the formula —NHCH(CH$_2$R$_2$)CH(OH)CH$_2$CH(R$_3$)C(O)NH—X$_3$—N(R$_4$)(R$_5$) wherein R$_2$, R$_3$, R$_4$, R$_5$ and X$_3$ are as defined therein;

European Patent Application No. EP320205, published Jun. 14, 1989, discloses mimics of the Leu-Val cleavage site of angiotensinogen having the formula —NHCH(CH$_2$R$_2$)CH(OH)CH$_2$CH(R$_3$)C(O)NH—X$_3$—N(R$_4$)(R$_5$) wherein R$_2$, R$_3$, R$_4$, R$_5$ and X$_3$ are as defined therein;

European Patent Application No. EP350163, published Jan. 10, 1990, discloses mimics of the Leu-Val cleavage site of angiotensinogen having the formula —NHCH(R$_3$)CH(OH)(CH$_2$)$_p$(CH(R$_z$))$_q$-A-R$_4$ wherein R$_3$, R$_4$, R$_z$, A, p and q are as defined therein;

European Patent Application No. EP316965, published May 24, 1989, discloses mimics of the Leu-Val cleavage site of angiotensinogen having the formula -A-B—Z—W wherein A, B, Z and W are as defined therein;

European Patent Application No. EP353211, published Jan. 31, 1990, discloses mimics of the Leu-Val cleavage site of angiotensinogen having the formula —NHCH(R$_3$)CH(OH)CH$_2$CH(R$_4$)CH$_2$S(O)$_q$R$_5$ wherein R$_3$, R$_4$, R$_5$ and q are as defined therein;

European Patent Application No. EP329013, published Aug. 23, 1989, discloses mimics of the Leu-Val cleavage site of angiotensinogen having the formula —NHCH(R$_1$)CH(OR$_9$)CH(R$_2$)(R$_3$) wherein R$_1$, R$_2$, R$_3$, and R$_9$ are as defined therein;

European Patent Application No. EP370454, published May 30, 1990, discloses mimics of the Leu-Val cleavage site of angiotensinogen having the formula —N(R$_1$)CH((CH$_2$)$_m$R$_2$)CH(OR$_3$)CH(OR$_4$)(CH$_2$)$_n$D wherein R$_1$, R$_2$, R$_3$, R$_4$, n and D are as defined therein;

European Patent Application No. EP332008, published Aug. 23, 1989, discloses mimics of the Leu-Val cleavage site of angiotensinogen having the formula —NHCH(R$_3$)CH(OR$_4$)CH(OR$_5$)(R$_6$) wherein R$_3$, R$_4$, R$_5$ and R$_6$ are as defined therein;

European Patent Application No. EP272444, published Jun. 29, 1988, discloses mimics of the Leu-Val cleavage site of angiotensinogen having the formula —N(R$_2$)CH(R$_3$)CH(R$_4$)(CH(R$_5$))$_n$)C(O)NH—E—W—Y wherein R$_2$, R$_3$, R$_4$, R$_5$,n, E, W and Y are as defined therein;

European Patent Application No. EP328978, published Aug. 23, 1989, discloses mimics of the Leu-Val cleavage site of angiotensinogen having the formula —N(R$_2$)CH(R$_3$)CH(R$_4$)(CH(R$_5$))$_n$)C(O)NH—E—Q—Y wherein R$_2$, R$_3$, R$_4$, R$_5$, n, E, Q and Y are as defined therein;

European Patent Application No. EP330925, published Sep. 6, 1989, discloses mimics of the Leu-Val cleavage site of angiotensinogen having the formula —N(R$_2$)CH(R$_3$)CH(R$_4$)(CH(R$_5$))$_n$)C(O)N-

H—E—Q—Y An⁻ wherein $R_2$, $R_3$, $R_4$, $R_5$, n, E, Q, Y and An⁻ are as defined therein;

European Patent Application No. EP339483, published Nov. 2, 1989, discloses mimics of the Leu-Val cleavage site of angiotensinogen having the formula —N($R_2$)CH($R_3$)CH($R_4$)$CH_2$C($R_5$)($R_6$)(Y) wherein $R_2$, $R_3$, $R_4$, $R_5$, $R_6$ and Y are as defined therein;

European Patent Application No. EP326364, published Aug. 2, 1989, discloses mimics of the Leu-Val cleavage site of angiotensinogen having the formula —NHCH($CH_2R_4$)CH(OH)$CH_2$CH(C((OH)($R_5$)($R_6$))C(O)N($R_7$)($R_8$) wherein $R_4$, $R_5$, $R_6$, $R_7$ and $R_8$ are as defined therein;

European Patent Application No. EP331105, published Sep. 6, 1989, discloses mimics of the Leu-Val cleavage site of angiotensinogen having the formula —NHCH($R_3$)CH(OH)P(=M)(Z'—$R_2$)-(Z—$R_1$) wherein $R_1$, $R_2$, $R_3$, M, Z' and Z are as defined therein;

PCT Patent Application No. WO89/03842, published May 5, 1989, discloses mimics of the Leu-Val cleavage site of angiotensinogen having the formula —NHC($R_{90}$)($R_{91}$)CH(OH)(CH($R_{100}$)-)$_n$—N($R_{101}$)($R_{102}$) wherein $R_{90}$, $R_{91}$, $R_{100}$, $R_{101}$, $R_{102}$ and n are as defined therein;

PCT Patent Application No. WO89/04833, published June 1, 1989, discloses mimics of the Leu-Val cleavage site of angiotensinogen having the formula —NHCH($CH_2R_2$)(X) wherein $R_2$ and X are as defined therein;

European Patent Application No. EP331921, published Sep. 13, 1989, discloses mimics of the Leu-Val cleavage site of angiotensinogen having the formula —W—U—V wherein W, U and V are as defined therein;

PCT Patent Application No. WO90/07521, published Jul. 12, 1990, discloses mimics of the Leu-Val cleavage site of angiotensinogen having the formula —NHCH($R_4$)CH(OH)$CH_2$C($R_5$)($R_6$)($R_7$) wherein $R_4$, $R_5$, $R_6$ and $R_7$ are as defined therein;

European Patent Application No. EP391179, published Oct. 10, 1990, discloses mimics of the Leu-Val cleavage site of angiotensinogen having the formula —NHCH($R_3$)CH(OH)$CH_2$CH(CH($CH_3$)$_2$)($R_4$) wherein $R_3$ and $R_4$ are as defined therein;

European Patent Application No. EP391180, published Oct. 10, 1990, discloses mimics of the Leu-Val cleavage site of angiotensinogen having the formula —NHCH($R_3$)CH($R_4$)($CH_2$)$_n R_5$ wherein $R_3$, $R_4$, $R_5$ and n are as defined therein;

British Patent Application No. GB2196958, published May 11, 1988, discloses mimics of the Leu-Val cleavage site of angiotensinogen having the formula —NHCH(R)C($R_1$)($R_2$)CH($R_3$)($R_4$)C($R_5$)($R_6$)-C(O)—B wherein R, $R_1$, $R_2$, $R_3$, $R_4$, $R_5$, $R_6$ and B are as defined therein;

European Patent Application No. EP373549, published Jun. 20, 1990, discloses mimics of the Leu-Val cleavage site of angiotensinogen having the formula —NHCH($R_2$)CH(=N(O)($R_4$)) wherein $R_2$ and $R_4$ are as defined therein;

German Patent Application No. DE3840452, published Jun. 7, 1990, discloses mimics of the Leu-Val cleavage site of angiotensinogen having the formula —NHCH($R_4$)CH(B(O$R_6$)(O$R_7$))—$R_5$ wherein $R_4$, $R_5$, $R_6$ and $R_7$ are as defined therein;

European Patent Application No. EP373497, published Jun. 20, 1990, discloses mimics of the Leu-Val cleavage site of angiotensinogen having the formula —NHCH($R_2$)CH(OH)CH($R_3$)($R_4$) wherein $R_2$, $R_3$ and $R_4$ are as defined therein;

European Patent Application No. EP372537, published Jun. 13, 1990, discloses mimics of the Leu-Val cleavage site of angiotensinogen having the formula —NHCH($R_2$)CH(OH)CH($R_3$)($CH_2$)$_p$—X—($CH_2$)$_q$—$R_4$ wherein $R_2$, $R_3$, $R_4$, X, p and q are as defined therein;

PCT Patent Application No. WO91/01327, published Feb. 7, 1991, discloses mimics of the Leu-Val cleavage site of angiotensinogen having the formula —NHCH($CH_2R_1$)CH(OH)CH(OH)$CH_2$C($R_2$)($R_3$)(NH$X_1$) wherein $R_1$, $R_2$, $R_3$ and $X_1$ are as defined therein; and Australian Patent Application No. AU39445/89, published Jan. 3, 1990, discloses mimics of the Leu-Val cleavage site of angiotensinogen having the formula —NHCH($R_1$)CH(O$R_2$)CH($CH_2$NH$R_3$)-C(O)—F—$R_4$ wherein $R_1$, $R_2$, $R_3$, $R_4$ and F are as defined therein.

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 2-methylbutyl, 2,2-dimethylpropyl, n-hexyl, 2-methylpentyl, 2,2-dimethylbutyl, n-heptyl and the like.

The term "cycloalkyl" as used herein refers to an aliphatic ring having 3 to 7 carbon atoms including, but not limited to, cyclopropyl, cyclopentyl, cyclohexyl and the like.

The term "cycloalkylalkyl" as used herein refers to a cycloalkyl group appended to a loweralkyl radical including, but not limited to, cyclohexylmethyl and the like.

The term "alkylene" as used herein refers to a 1 to 6 carbon straight or branched chain diradical including, but not limited to, —$CH_2$—, —CH($CH_3$)—, —$CH_2CH_2CH_2$—, —CH($CH_3$)$CH_2CH_2$— and the like.

The term "substituted alkylene" as used herein refers to an alkylene group which is substituted with one or two groups independently selected from loweralkyl, alkoxy and thioalkoxy.

The term "hydroxyalkyl" as used herein refers to an —OH group appended to a loweralkyl radical including, but not limited to, hydroxymethyl, hydroxyethyl, hydroxypropyl and the like.

The term "halo-substituted loweralkyl" or "haloalkyl" as used herein refers to a loweralkyl group which is substituted with one or more halo groups including, but not limited to, chloromethyl, trifluoromethyl, trichloroethyl, bromoethyl and the like.

The term "alkanoyl" as used herein refers to —C(O)$R_4$ wherein $R_4$ is a loweralkyl group.

The term "alkoxycarbonyl" as used herein refers to —C(O)O$R_5$ wherein $R_5$ is loweralkyl or halo-substituted loweralkyl.

The terms "alkoxy" and "thioalkoxy" as used herein refer to —O$R_7$ and —S$R_7$, respectively, wherein $R_7$ is a loweralkyl group.

The term "alkylamino" as used herein refers to —NH$R_8$ wherein $R_8$ is a loweralkyl group.

The term "dialkylamino" as used herein refers to —NR$_9$R$_{10}$ wherein R$_9$ and R$_{10}$ are independently selected from loweralkyl.

The term "halogen" or "halo" as used herein refers to I, Br, Cl or F.

The term "aroyl" as used herein refers to —C(O)R$_6$ wherein R$_6$ is an aryl group.

The term "aryl" as used herein refers to a C$_6$ monocyclic aromatic ring system or a C$_9$ or C$_{10}$ bicyclic carbocyclic ring system having one or more aromatic rings including, but not limited to, phenyl, naphthyl, tetrahydronaphthyl, indanyl, indenyl and the like. Aryl groups can be unsubstituted or substituted with one, two or three substituents independently selected from loweralkyl, haloalkyl, alkoxy, thioalkoxy, alkoxycarbonyl, alkanoyl, hydroxy, halo, mercapto, nitro, amino, alkylamino, dialkylamino, carboxaldehyde, carboxy and carboxamide.

The term "N-protecting group" or "N-protected" as used herein refers to those groups intended to protect nitrogen atoms against undesirable reactions during synthetic procedures or to prevent the attack of exopeptidases on the final compounds or to increase the solubility of the final compounds. N-protecting groups include alkanoyl, alkoxycarbonyl or aroyl and include but are not limited to formyl, acetyl, pivaloyl, t-butylacetyl, trichloroethoxycarbonyl, t-butyloxycarbonyl (Boc), benzyloxycarbonyl (Cbz) or benzoyl groups or an L- or D-aminoacyl residue, which may itself be N-protected similarly.

The terms "substituted morpholinyl" (Z is O), "substituted thiomorpholinyl" (Z is S) and "substituted thiomorpholinyl dioxide" (Z is S(O)$_2$) as used herein refer to a morpholinyl group, a thiomorpholinyl group or a thiomorpholinyl dioxide group, respectively, which is substituted with one, two, three or four groups independently selected from loweralkyl including, but not limited to,

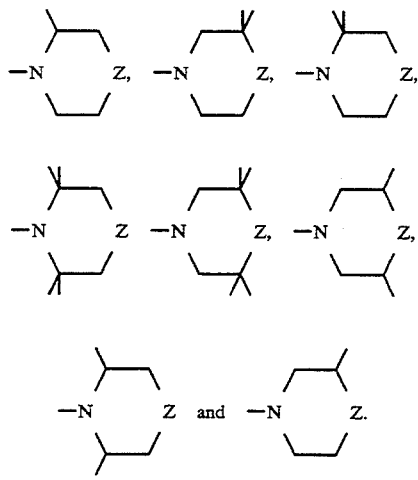

Substituted morpholinyl, substituted thiomorpholinyl or substituted thiomorpholinyl dioxide also include

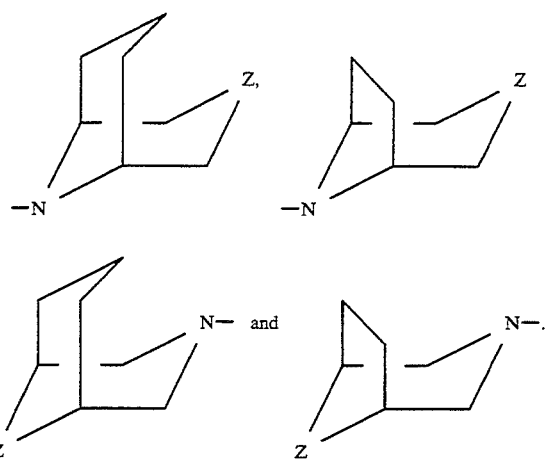

In addition, the term "substituted morpholinyl" as used herein also refers to

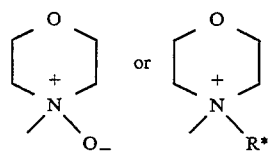

wherein R* is loweralkyl.

The compounds of formula I contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

The compounds of the invention can be prepared as shown in Schemes 1-9. In Scheme 1, the diprotected hydroxyethylene dipeptide isostere 1 (European Patent Application No. EP364804, published Apr. 25, 1991), or an activated derivative thereof, is coupled to an appropriately functionalized amine 2 (Y and R$_1$ are defined as above) to provide the amide 3. Standard peptide coupling conditions known to those skilled in the art can be used. In particular, the scheme illustrates the use of 1-hydroxybenzotriazole (HOBT), 1-(3-dimethylaminopropyl)-3-ethyl-carbodiimide (EDCI) and N-methylmorpholine (NMM). This coupling reaction can be achieved by other standard peptide coupling methods (active ester method, BOP-chloride, as well as other carbodiimides, e.g. DCC, DIC). The derived amide then can be deprotected by the two-stage method of 1) BOC-removal with trifluoroacetic acid, followed by 2) aqueous hydrolysis of the aminal, which produces the aminoalcohol 4. Standard peptide coupling of 4 to 5 yields the product 6. Again, any peptide coupling method could be used for this transformation.

Activated derivatives of carboxylic acids as mentioned herein refer to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

Scheme 2 illustrates a method to prepare compounds of the invention wherein the C-terminus is further functionalized. For example, the amino-terminal diprotected hydroxyethylene dipeptide isostere 7 can be reacted with appropriate electrophiles 8 to produce amides, carbamates, ureas or amidines or guanidines, using methods available in the chemical literature. The same deprotection/coupling sequence described in Scheme 1 then leads to the N-terminal functionalized compound 10. It should be noted that amines such as 7 also may be reacted with sulfur-based electrophiles (sulfenyl, sulfinyl, sulfonyl, or sulfamoyl halides) to produce sulfenamides, sulfinamides, sulfonamides or sulfamides, respectively. In addition, it should be apparent to those skilled in the art that the method of Scheme 1 can be used to prepare compound 10 wherein intermediate 2 is appropriately functionalized.

Scheme 3 illustrates an alternate preparation of compound 6. Alkylation of (R)-2-bromohexanoic acid with the sodium salt of alcohol 11 (European Patent Application No. EP364804, published Apr. 25, 1991), provides carboxylic acid 5a as a single diastereomer after silica gel column chromatography. (Alternatively, crude compound 5a can be converted to an active ester derivative (such as the mono- or di-nitrophenylester) prior to chromatographic separation of the diastereomers). The acid 5a (or an active ester derivative) is then coupled to the amino lactone 12 (Bradbury, R. H.; Revill, J. M.; Rivett, J. E.; Waterson, D. *Tetrahedron Lett.* 1989, 3845) using standard peptide coupling procedures to give the key intermediate 13. Lactone 13 is then reacted with amine 2 to give the amide 6.

Scheme 4 illustrates the preparation of a representative compound of the invention having a C-terminal carboxyl-derivative. Diprotected acid 1 and beta-alanine ethyl ester are coupled to give amide 15, which is then deprotected and coupled to the desired acid 5 in a manner analogous to that described in Scheme 1. The derived C-terminal ester 16 is hydrolyzed to the corresponding carboxylic acid 17 by standard methods.

As illustrated in Scheme 5, benzyl carbamates 18 serve as convenient sources of the primary amines 19, by catalytic hydrogenation. The derived amines 19 can be derivatized by standard methods. Thus, elaboration with N-acetoxy-norbornene-2,3-dicarboximide gives the N-acetyl compound 20. Treatment with trimethylsilyl isocyanate gives urea 21. Sequential reaction with N,N'-thiocarbonyldiimidazole and an alkylamine gives N-substituted thiourea 22. Sulfamide 23 may be prepared by reaction of 19 with a sulfamoyl chloride.

Scheme 6 illustrates the preparation of guanidine derivatives and the related 1,2,3-triazoles and 1,3,4-oxadiazoles from amines 19. Amine 19 can be reacted with dimethyl N-cyanoimidodithiocarbonate to give N-cyano-S-methylisothiourea 24. Compound 24 can be further elaborated by reaction with hydrazine to give 3,5-diaminotriazole 25, with hydroxylamine to give 2,5-diamino-oxadiazole 26, or with ammonia ($R_{19}$=H) or an alkylamine ($R_{19}$=alkyl) to give N-unsubstituted or N-substituted guanidine 27.

Scheme 7 illustrates another method for preparing the compounds of the invention (6). The protected amino lactone 28 may be converted to amido carbamates 29 by reaction with neat amines at temperatures ranging from 25°–75° C. Alternatively, alkylaluminum-mediated lactone openings of 28 have been described to effect this transformation (Chakravarty, P. K.; de Laszlo, S. E.; Sarnella, C. S.; Springer, J. P.; Schuda, P. F. *Tetrahedron Lett.* 1989, 30, 415–8). The Boc group can be removed with TFA, and the resulting amine (preferably as the free base) can be coupled to acids 5a, 5b or 5c using standard peptide coupling methodology to provide the compound 6.

Scheme 8 illustrates the preparation of C-terminal derivatives in which the C-terminal amide has been replaced by methyleneoxy, methyleneamino, methylenethio or methylenesulfonyl-derivatives. Boc-lactone 28 is reduced with, for example, sodium borohydride-calcium chloride to the diol carbamate 30. The procedures of Karlsson, J. O.; Lundblad, A.; Malm, B.; Nilsson, I.; Nitenberg, T.; Starke, I.; Sörenson, H.; Westerlund, C. *Tetrahdron Lett.* 1989, 30, 2653–6, are adapted for the following transformations. The secondardary alcohol is internally protected by conversion to the oxazolidinone 31, and the primary hydroxyl group is derivatized. For example, the primary hydroxyl group is converted to the methoxymethyl ether 32, or transformed to the sulfide 34 via the intermediate mesylate 33. The sulfide is oxidized to the corresponding sulfone 35 with a peroxyacid (e.g. m-CPBA or Oxone and the like). Treatment of oxazolines 32, 34, and 35 with barium hydroxide affords amino alcohols 36, 37, and 38, respectively. Standard peptide coupling of amino alcohols 36, 37, and 38 with acids 5a or 5b afford products 39.

Scheme 9 illustrates an alternative method for the preparation of compound 5a. Reaction of aldehyde 40 with an n-butyl organometallic reagent (for example, n-butyl magnesium bromide and the like), followed by oxidative resolution using (−) DIPT t-BuOOH Ti $(OCH(CH_3)_2)_4$, provides 41 as a single enantiomer. (DIPT is diisopropyl tartrate). Reaction of the alcohol 41 with a halo acetic acid, optionally followed by esterification, or a halo acetic acid ester provides 42 or 43. Alternatively, reaction with t-butyl bromoacetate provides 44. Alkylation with a benzyl halide (for example, benzyl bromide and the like) provides a mixture of 45 and the desired 46. Compound 46 can be separated from the mixture by silica gel chromatography. Hydrogenolysis or hydrolysis of the ester, coupling with 4-methoxymethoxypiperidine and oxidation provides the desired carboxylic acid 5a.

Scheme 10 illustrates an alternative preparation of intermediate 41. 2-Valeryl furan 47 (prepared by Friedel-Crafts acylation of furan) is stereoselectively reduced with diborane and a chiral catalyst (10–20 mole % of a compound such as 48, 49 or 50 and the like (see Scheme 11)) in a solvent such as tetrahydrofuran and the like.

Scheme 11 illustrates the preparation of the chiral catalysts 48 and 49. The known (5S or 5R) 4-(t-butoxycarbonylamino)-5-(substituted)-2H-1,4-oxazine-2-ones (PCT Application No. WO90/03971, published Apr. 19, 1990) are alkylated to give 51 $R_{80}$ and $R_{81}$ are independently selected from hydrogen, loweralkyl, cycloalkyalkyl, phenyl and benzyl and $R_{82}$ and $R_{83}$ are independently selected from hydrogen, loweralkyl, cycloalkylalkyl and benzyl). The alkylated compound 51 is reduced with diborane to the Boc diol which is deprotected to give the amine diol 52. Reaction of 52 with $BH_3$, trimethyl borate, trimethyl aluminum or titanium isopropoxide and the like gives 48 (M=B, Al, TiOisopropyl). Similarly, 51 can be deprotected with HCl dioxane and the crude salt reacted with excess Grignard reagent ($R_{82}$=loweralkyl, cycloalkylalkyl, phenyl or benzyl) to give the amine diol 53. Reaction of 53 with $BH_3$, trimethyl borate, trimethyl aluminum or titanium isopropoxide and the like gives compound 49 (M=B, Al, TiOisopropyl). Catalyst 50 and DAIB are prepared by literature procedures.

Scheme 12 illustrates the preparation of compound 5b. N-CBz-L-phenylalanine (54) is coupled to the 4-methoxymethyl ether of 4-hydroxypiperidine. Hydrogenolysis of the CBz group gives amine 55, which is used without further purification. Alkylation of 55 with optically active (2R) ethyl 2-bromohexanoate in a polar solvent such as DMSO, nitromethane or DMF and the like (nitromethane preferred) with a base present (for example, triethylamine, sodium carbonate, ammonium carbonate and the like (ammonium carbonate preferred) gives ester 56. Base hydrolysis of 56 with sodium hydroxide, lithium hydroxide, potassium hydroxide and the like, gives 5b.

Scheme 1

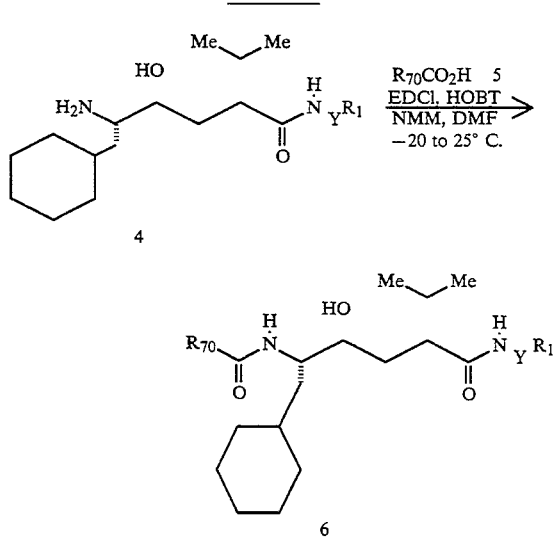

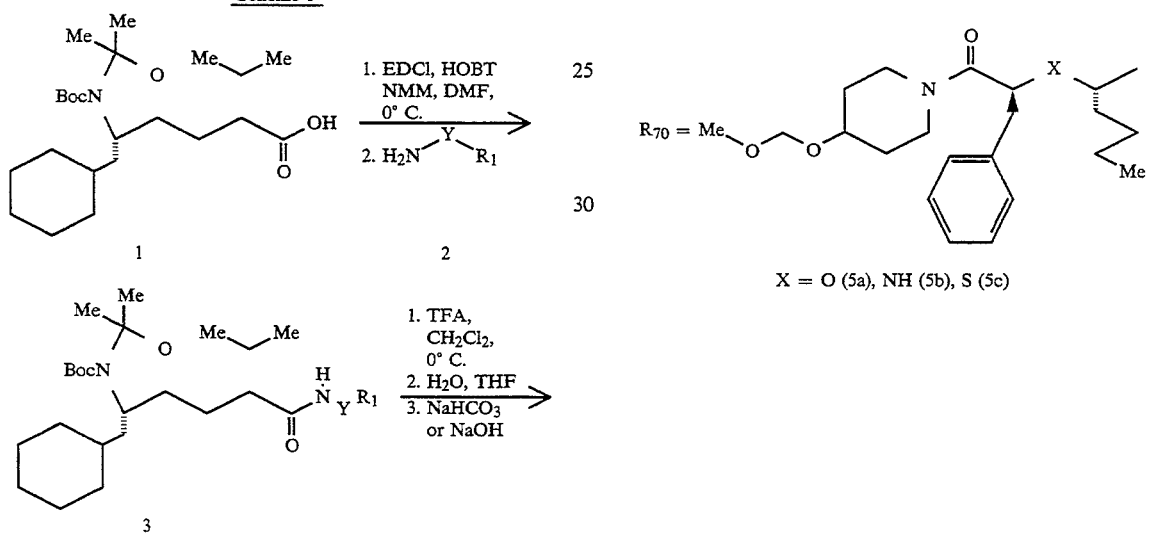

X = O (5a), NH (5b), S (5c)

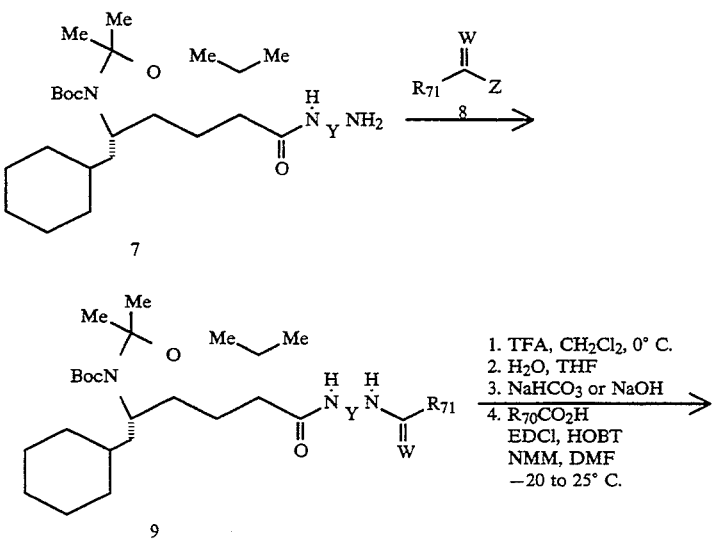

Scheme 2
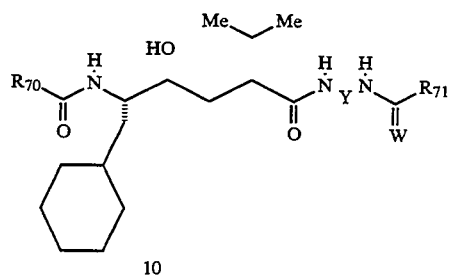
10
$R_{71}$ = $NH_2$, —$NHR_{19}$, —$SR_{22}$, loweralkyl, alkoxy or thioalkoxy
W = O, NH, NCN, S
Z = Cl, $SCH_3$
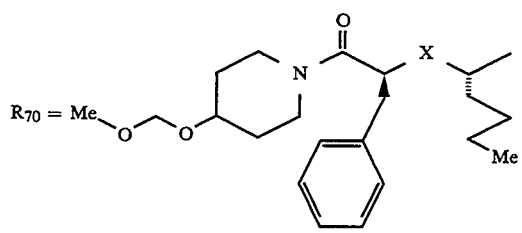
X = O (5a), NH (5b), S (5c)
Scheme 3
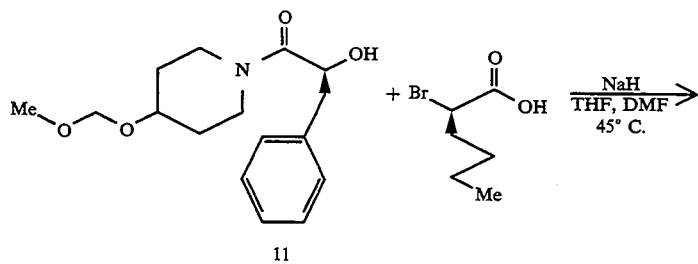
11
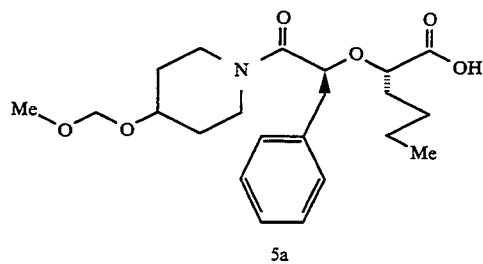
5a
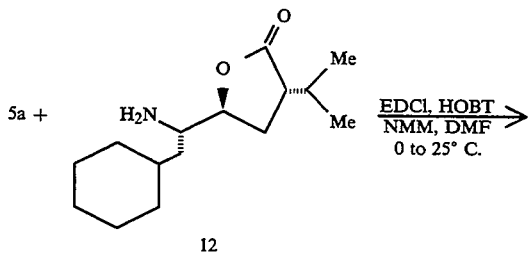
12

Scheme 3
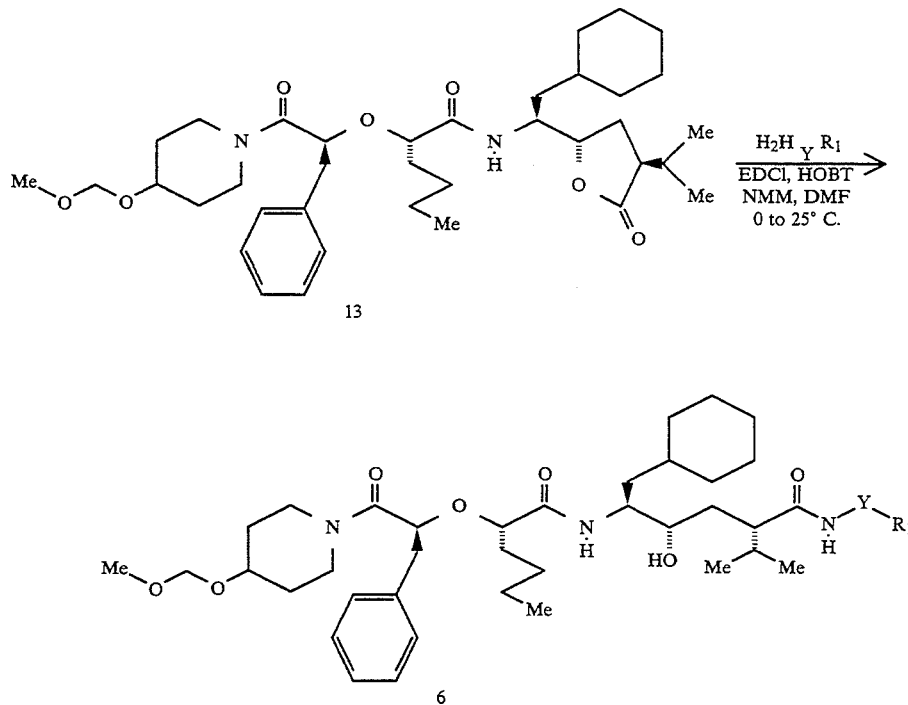
Scheme 4
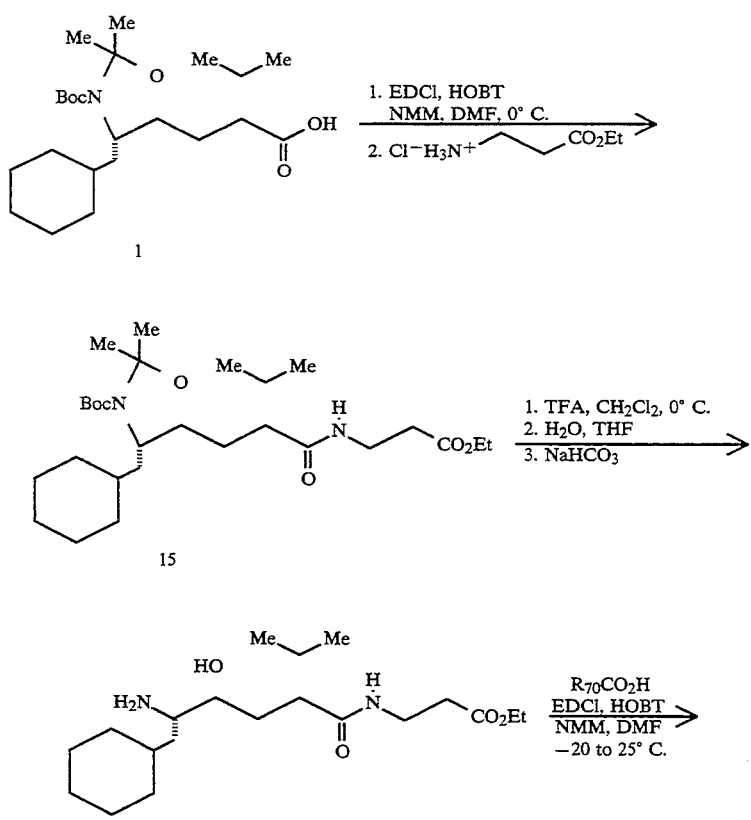

Scheme 4
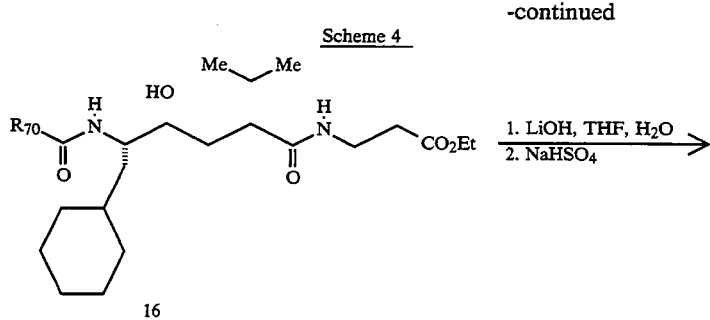
16
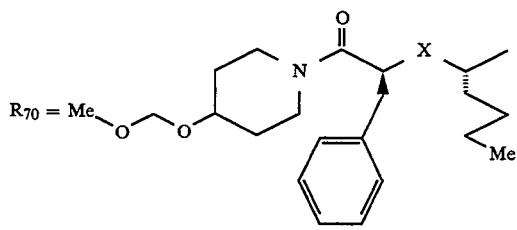
17
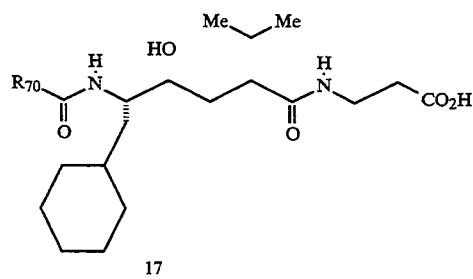
X = O (5a), NH (5b), S (5c)
Scheme 5
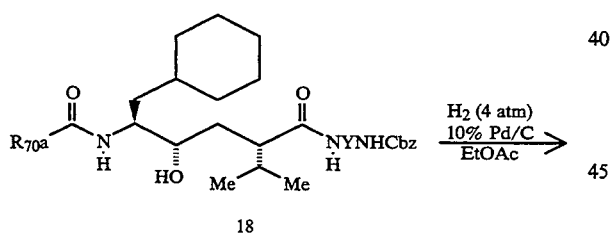
18
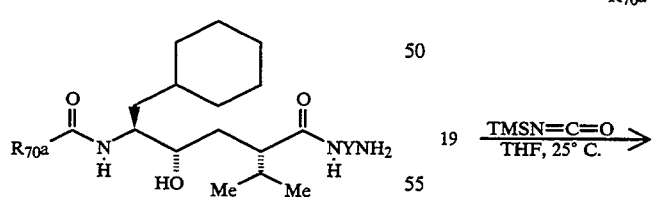
19
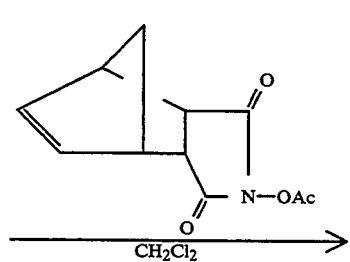
19
-continued Scheme 5
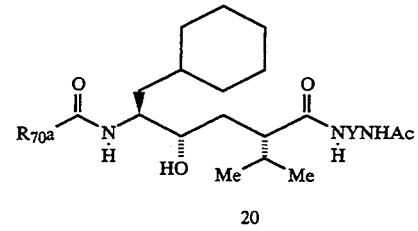
20
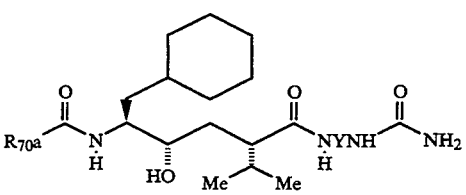
21
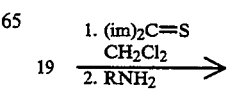

-continued
Scheme 5
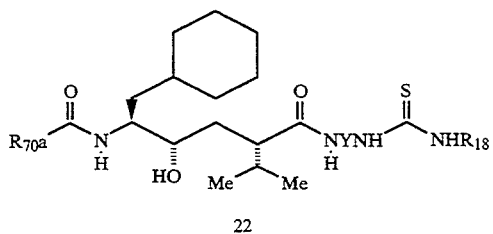
22
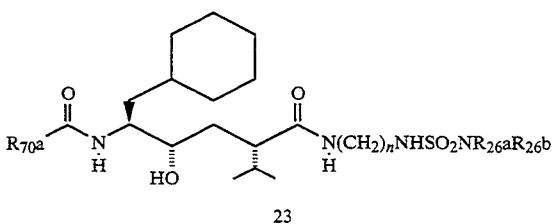
23
19 $\xrightarrow{R_{26a}R_{26b}NSO_2Cl}{Et_3N, CH_2Cl_2}$
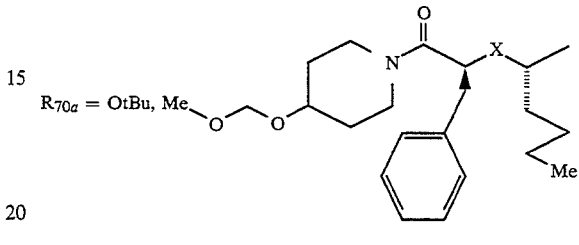
$R_{70a}$ = OtBu, Me$\diagdown$O$\diagdown$O$\diagdown$
X = O, NH, S
Scheme 6
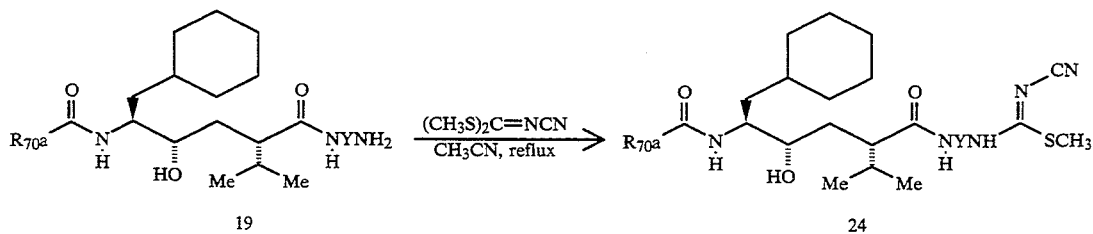
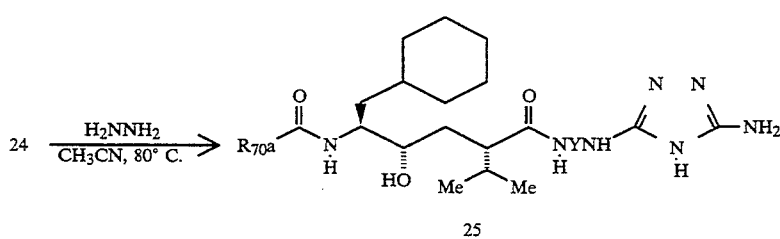
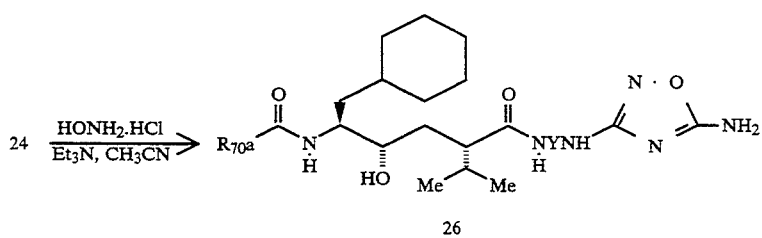
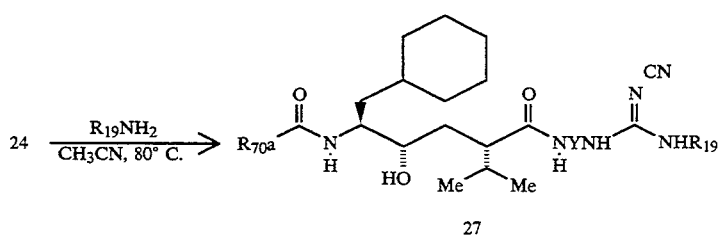

-continued
Scheme 6
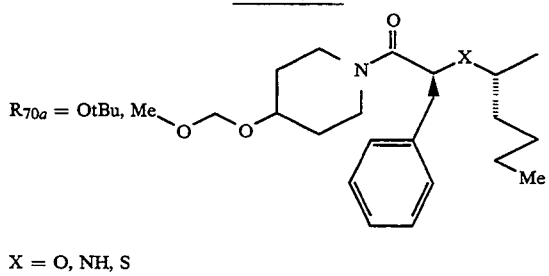
X = O, NH, S
Scheme 7
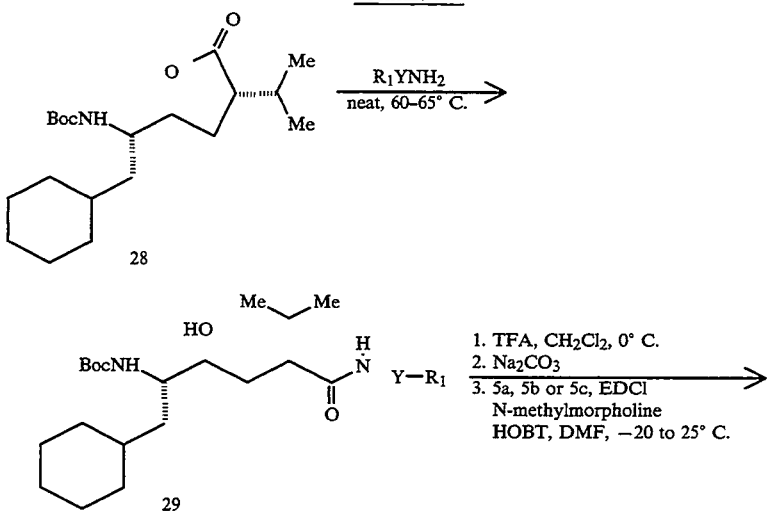
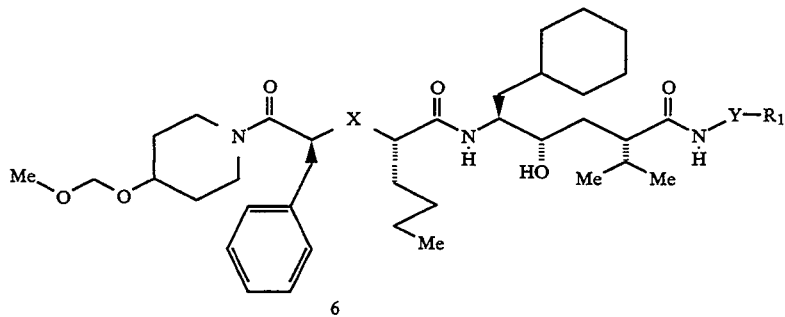

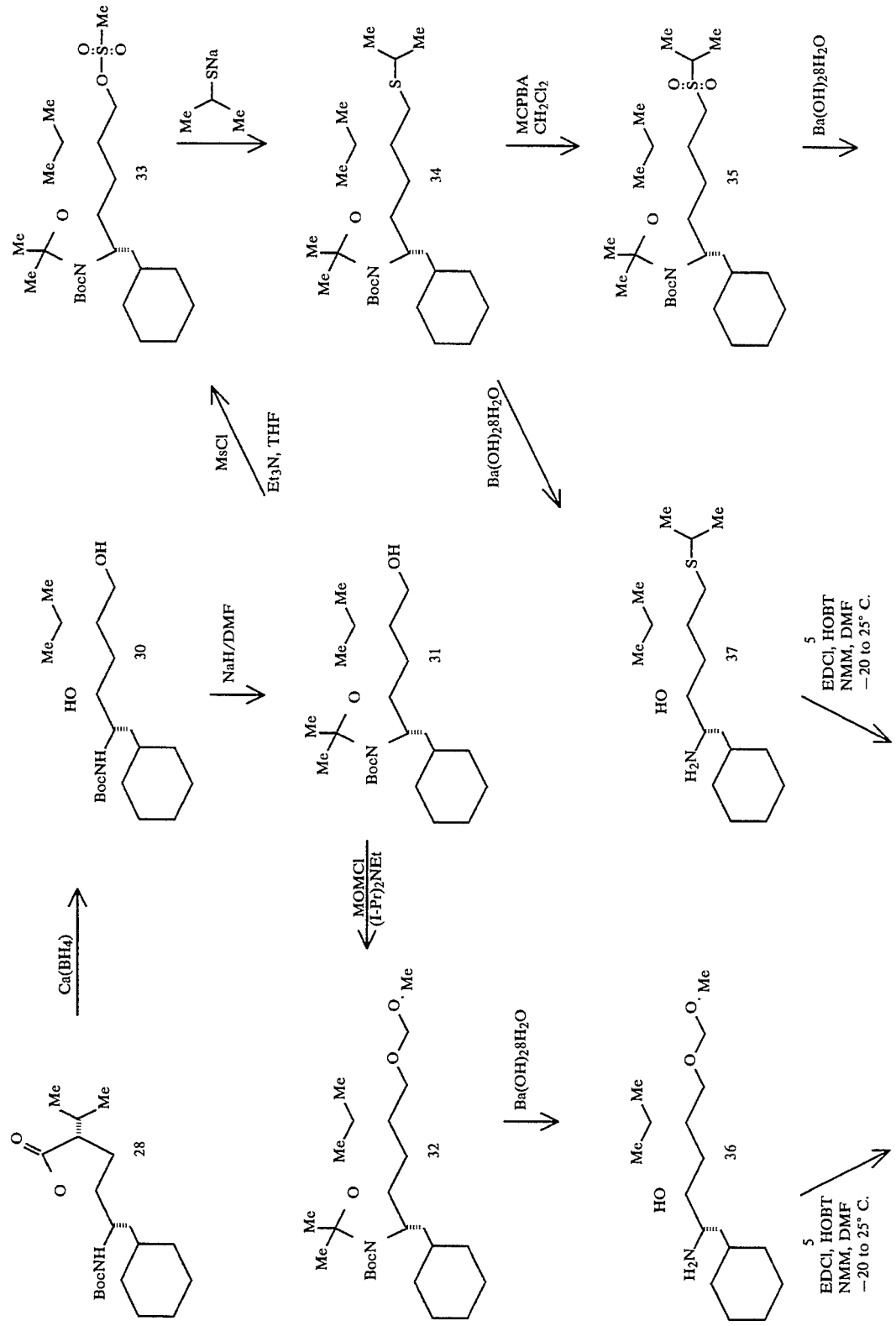

Scheme 8 -continued
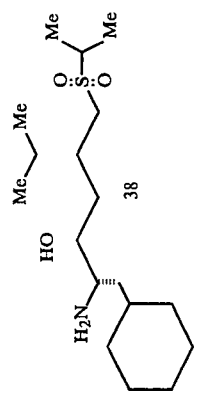
EDCI, HOBT
NMM, DMF
−20 to 25° C.
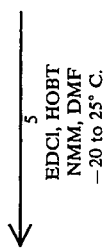
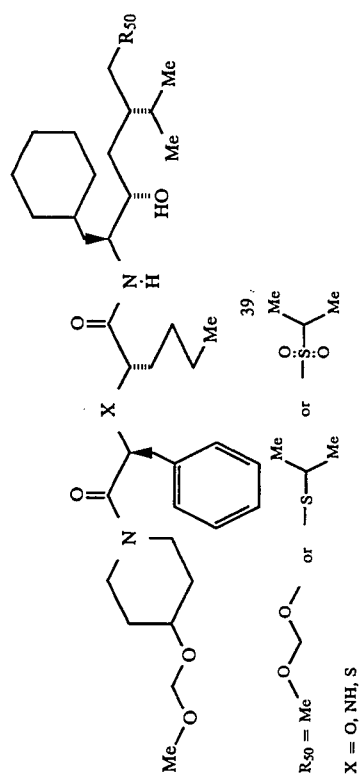
$R_{50}$ = Me$\diagup$O$\diagup$O$\diagup$Me
X = O, NH, S

29
Scheme 9
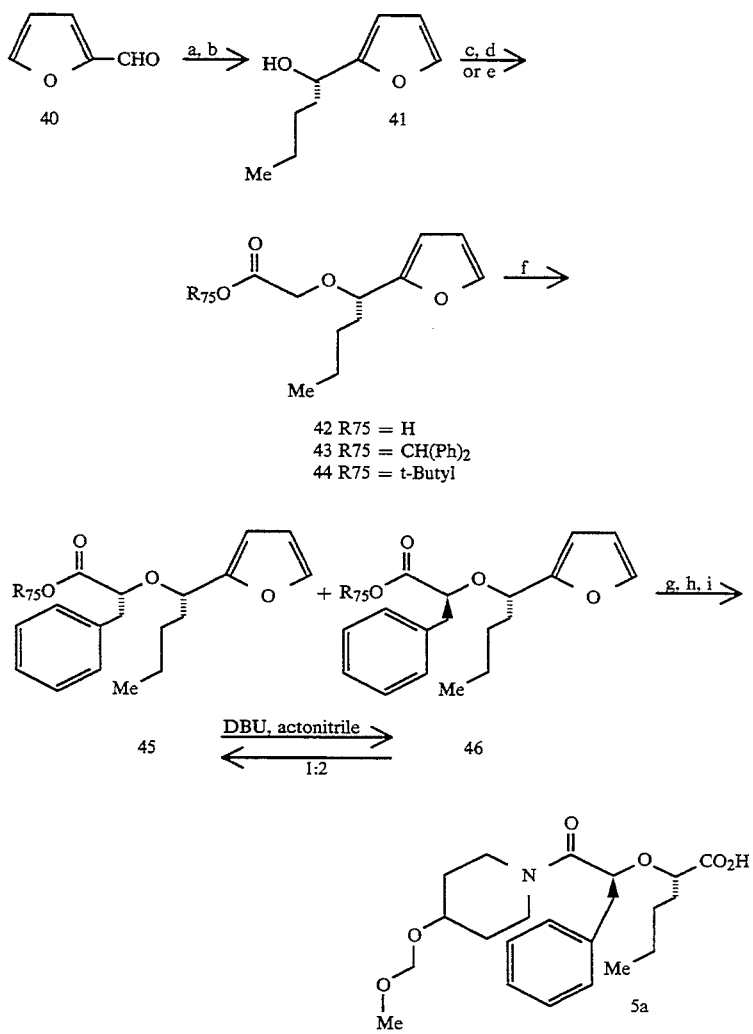
Reagents:
a) n-BuMgBr,
b) (—) DIPT t-BuOOH Ti(OCH(CH$_3$)$_2$)$_4$,
c) NaH BrCH$_2$CO$_2$H,
d) CH$_2$N$_2$ or C(Ph)$_2$N$_2$,
e) KN(TMS)$_2$ BrCH$_2$CO$_2$t-Bu,
f) NaN(TMS)$_2$ BnBr,
g) when R$_{75}$ = CH(Ph)$_2$ H$_2$ Pd/C, when R$_{75}$ = t-BuHCl methanol,
h) EDC 4-methoxymethoxypiperidine,
i) O$_3$ or NaIO$_4$ RuCl$_3$
30
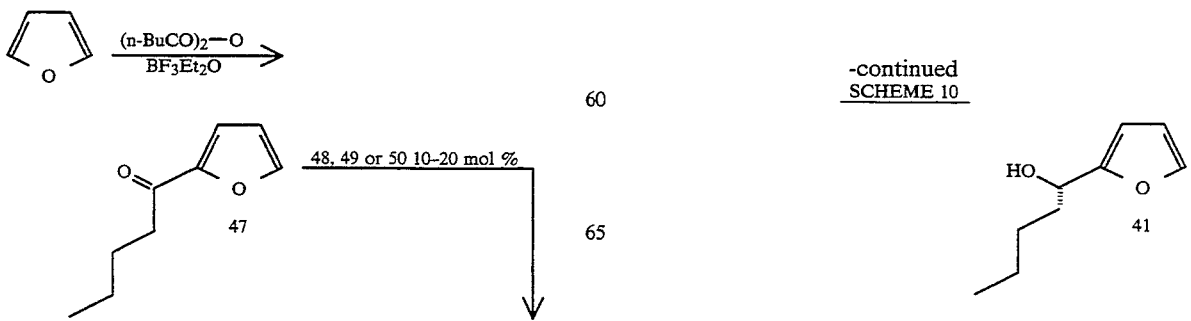

SCHEME 11

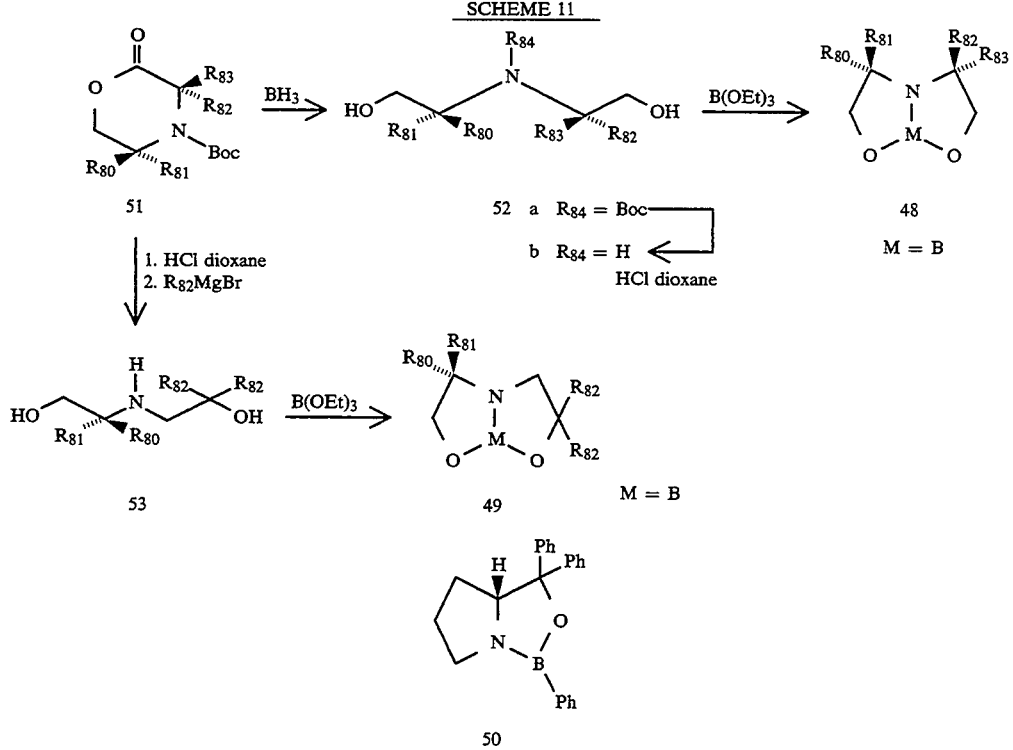

SCHEME 12

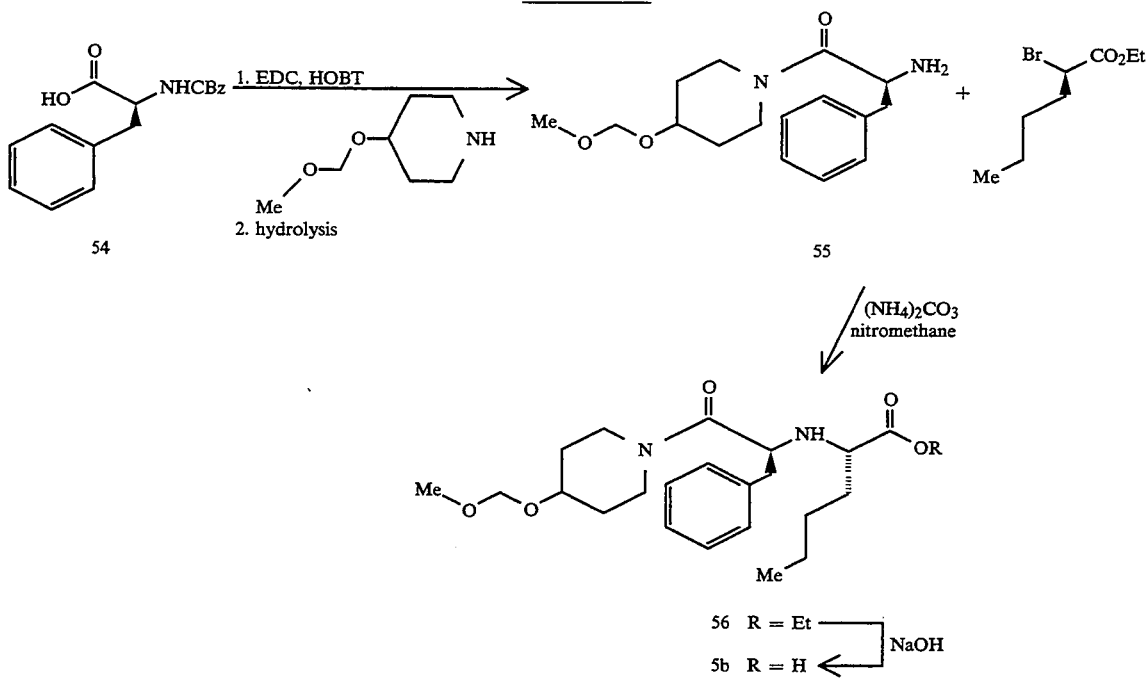

The following Examples will serve to further illustrate preparation of the novel compounds of the present invention.

EXAMPLE 1

2(S)-(1(S)-(4-(Methoxymethoxy)piperidin-1-yl-carbonyl)-phenylethoxy)hexanoic acid 1(S)-(4-(Methoxymethoxy)piperidin-1-yl-carbonyl)-2-phenylethanol (European Patent Application No. EP364804, published Apr. 25, 1991) (43.13 g, 147.2 mmol) in 200 mL dry THF was added dropwise to the suspension of sodium hydride (60% dispersion in oil, 12.36 g, 309.1 mmol) in 136 mL dry THF and 22.7 mL DMF at 45° C. oil bath temperature under $N_2$ atmosphere. The addition took approximately 1 h. The mixture was allowed to stir at 45° C. for additional 3 h. The gray suspension turned white after stirring for an hour and became very viscous. An additional 36 mL of dry THF was added to facilitate stirring. A solution of (R)-2-bromohexanoic acid (31.57 g, 161.9 mmol) in 180 mL THF was added dropwise to the thick, white suspension at 45° C. The addition took approximately 1.75 h. The suspension was removed from the oil bath 45 min after addition was completed and quenched immediately with careful addition of 120 mL of pH 7 phosphate buffer (0.3M). The solution was then concentrated under reduced pressure at 35° C. and the resulting liquid extracted with 3×100 mL of diethyl ether to remove the unreacted alcohol. The aqueous phase was mixed with 300 mL of $CH_2Cl_2$ and acidified to pH 2 with 200 mL of 1M sodium hydrogen sulfate. The layers were shaken and separated, then the aqueous phase was extracted with 2×300 mL of $CH_2Cl_2$. The combined organic phase was dried ($MgSO_4$), filtered and concentrated under reduced pressure. The crude product was purified by column chromatography (silica gel, 1.5% HOAc-5% iPrOH-35% THF-hexane) to obtain 36.35 g (88.32 mmol, 60%) of the desired compound as a low-melting solid: Rf 0.30 (EtOAc-hexane 5:2); $^1H$ NMR ($CDCl_3$) δ0.8 (d, 3H), 0.95 (m, 5H), 1.2–1.9 (m, 22H), 3.0 (q, 2H), 3.2 (m, 4H), 3.55 (m, 2H), 3.65 (m, 2H), 3.8 (t, 1H), 4.4 (q, 1H), 7.3 (m, 5H).

EXAMPLE 2

N-(3-(Benzyloxycarbonylamino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. 3-(Benzyloxycarbonylamino)propylamine.

1,3-Diaminopropane (35.5 g, 0.48 mol) was dissolved in 300 mL $CHCl_3$, and the solution was cooled to 0° C. A solution of N-(benzyloxycarbonyloxy) succinimide (4.5 g, 0.018 mol) in 150 mL $CHCl_3$ was added dropwise over 6 h, with the internal temperature maintained below 10° C. After addition was complete, the reaction solution was stirred at room temperature overnight. The solution was washed with water, dried ($Na_2SO_4$), filtered and concentrated in vacuo to provide 3.0 g (80%) of the title compound as a low melting solid: $^1H$ NMR ($CDCl_3$) δ1.25 (bs, 2H), 1.63 (quintet, 2H), 2.77 (t, 2H), 3.2–3.34 (bm, 2H), 5.09 (s, 2H), 5.37 (bm, 1H), 7.28–7.40 (m, 5H); MS, m/e 209 ((M+H)+).

B. N-(3-(Benzyloxycarbonylamino)propyl) 2(S)-((3-(tert-butyloxycarbonyl)-2,2-dimethyl-4(S)-cyclohexylmethyl-5(S)-oxazolidinyl)methyl)-3-methylbutanamide.

2(S)-((3-(tert-Butyloxycarbonyl-2,2-dimethyl-4(S)-cyclohexylmethyl-5(S)-oxazolidinyl)methyl)-3-methylbutanoic acid (European Patent Application No. EP364804, published Apr. 25, 1991) (1.50 g, 3.64 mmol), HOBT (837 mg, 5.47 mmol), 3-(benzyloxycarbonylamino)propylamine (949 mg, 4.56 mmol) and N-methylmorpholine (601 mg, 5.47 mmol) were dissolved in 36.5 mL dry DMF, and the solution was cooled to −20° C. under a nitrogen atmosphere. N-Ethyl-N'-(dimethylamino)propylcarbodiimide hydrochloride (978 mg, 5.10 mmol) was added as a solid, and the resulting mixture was stirred at −20° C. for 4 h, then the resulting solution was stirred 16 h at room temperature. The volatiles were removed by high vacuum distillation, the residue was dissolved in 150 mL $CH_2Cl_2$ and extracted with, 2×300 mL 80% saturated aq. $NaHCO_3$, water (300 mL), and brine (300 mL), then the organic phase was dried ($Na_2SO_4$) and concentrated to a foam. Purification by flash chromatography (silica gel, 10% EtOAc—$CH_2Cl_2$) provided 1.98 g (3.28 mmol, 90%) of the desired compound as a white foam: Rf 0.11 (25% EtOAc-hexane); $^1H$ NMR ($CDCl_3$) δ0.94 (m, 8H), 1.0–1.5 (vbm, 8H), 1.48 (s, 9H), 1.52–1.90 m, 14H), 2.05 (m, 1H), 3.25 (m, 2H), 3.34 (m, 2H), 3.65 (bm, 1H), 3.71 (m, 1H), 5.10 (s, 2H), 5.48 (bt, 1H), 6.00 (bt, 1H), 7.3–7.36 (m, 5H); MS m/e 602 ((M+H)+), 619 ((M+$NH_4$)+).

C. Part 1.

A solution of the resultant compound from Example 2B (119 mg, 0.198 mmol) in 1.5 mL $CH_2Cl_2$ was cooled to 0° C., and 1.5 mL trifluoroacetic acid was added dropwise over 2 min. The resulting solution was stirred at 0° C. for 4 h, then was concentrated in vacuo to give an oil. The crude aminal salt was dissolved in 3 mL THF and 1 mL $H_2O$ and the solution was stirred at 0° C. for 18 h. The mixture was concentrated in vacuo to give an aqueous suspension, which was then partitioned between 20 mL saturated aq. $NaHCO_3$ and 20 mL $CH_2Cl_2$. The aqueous phase was extracted with 2×20 mL $CH_2Cl_2$, then the combined organic phases were dried ($Na_2SO_4$), filtered and concentrated in vacuo to give 95 mg (104%) of the crude amino alcohol N-(3-(benzyloxycarbonylamino)propyl) 5(S)-amino-6-cyclohexyl-4(S)-hydroxy-2(S)-isopropylhexanamide; Rf 0.30 (10% MeOH—$CH_2Cl_2$); $^1H$ NMR ($CDCl_3$) δ0.92 (m, 6H), 0.7–1.9 (several bm, 18H approx.), 2.15 (m, 1H), 2.59 (m, 1H), 3.10 (m, 1 HP), 3.20–3.42 (bm, 5H), 5.09 (s, 2H), 5.43 (bm, 1H), 6.19 (bm, 1H), 7.28–7.40 (m, 5H).

Part 2.

The crude amino alcohol from Example 2C, Part 1 (90.5 mg, 0.196 mmol), the resultant compound from Example 1 (87.9 mg, 0.216 mmol), HOBT (34.5 mg, 0.225 mmol), and N-methylmorpholine (22 mg, 0.22 mmol) were dissolved in 2.0 mL DMF, and the resulting solution was cooled to −23° C. EDCI (52.6 mg, 0.275 mmol) was added, and the mixture was stirred at −23° C. for 4 h, and allowed to warm to room temperature was stir overnight (18 h). The solvent was removed by high vacuum distillation, and the residue was partitioned between 25 mL $CH_2Cl_2$ and 80% saturated aq. $NaHCO_3$. The organic phase was washed sequentially with $H_2O$ (25 mL) and brine (25 mL), then dried ($Na_2SO_4$), filtered and concentrated in vacuo to a foamy solid (174 mg). Flash chromatography (silica gel, 2.5% MeOH—$CH_2Cl_2$) provided 106 mg (0.125 mmol, 64%) of the title compound as a white foam; mp 64°–68° C.; $^1H$ NMR ($CDCl_3$) δ0.9 (m, 9H), 0.65–1.90 (several bm, 28H approximately), 2.05 (m, 1H), 2.9–3.1 (m, 2H), 3.1–3.4 (bm, 17H approximately), 3.37 (s, 3H), 3.5 (bm, 1H), 3.6–4.0 (vbm, 5H), 4.50 (bm, 1H), 4.67 (s, 2H), 5.10 (AB, 2H), 5.51 (bt, 1H), 5.77–5.9 (2 d, 1H), 6.09 (bt, 1H), 7.27–7.4 (m, 10H); MS m/e 851 ((M+H)+). Anal. Calcd for $C_{48}H_{74}N_4O_9$·0.5 $H_2O$: C, 67.03; H, 8.79; N, 6.51. Found: C, 66.91; H, 8.64; N, 6.48.

EXAMPLE 3

N-(3-Aminopropyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. The resultant compound from Example 2 (50 mg, 0.0587 mmol) was stirred with 10% palladium on carbon (13 mg) in 3 mL EtOAc under 1 atmosphere of hydrogen for 3 days. The mixture was filtered, and the filtrate was concentrated to a foam. Thin-layer chromatography (silica gel, 10% MeOH-1% concentrated aq. NH₄OH—CH₂Cl₂) gave 26.4 mg (0.0368 mmol, 63%) of the title compound as a white foamy solid: mp 58°-60° C.; Rf 0.26 (10% MeOH-1% concentrated aq. NH₄OH—CH₂Cl₂); ¹H NMR (CDCl₃) δ0.90–0.92 (m, 9H), 0.65–2.0 (vbm, 28H total approximately), 2.05 (m, 1H), 2.82 (dd, 2H), 2.9–3.1 (m, 2H), 3.13–3.28 (bm, 2H), 3.37 (s, 3H), 3.3–3.55 (bm, 5H), 3.6–4.0 (vbm, 5H), 4.50 (dd, 1H), 4.67 (s, 2H), 5.79 (d) and 5.87 (d, 1H total), 6.52 (bm, 1H), 7.30 (bs, 5H); MS m/e 717 ((M+H)+). HRMS. Calcd for ((M+H)+) of C₄₀H₆₉N₄O₇: 717.5166. Found: 717.5178.

B. An alternative procedure for the preparation of this compound follows. A mixture of the resultant compound of Example 9 (2.3 g, 3.58 mmol) and 20 equivalents of 1,3-diaminopropane was stirred at 55° C. for 4 h and at 65° C. for 6 h. The mixture was diluted with EtOAc and washed with water. The organic portion was dried, filtered and evaporated. The residue was column chromatographed (silica gel, 4% MeOH-1% concentrated aq. NH₄OH—CHCl₃) to produce 2.0 g (2.79 mmol, 78%) of the desired product as a hygroscopic foam. The compound obtained from this procedure was identical in all respects to the compound obtained from the previous procedure.

EXAMPLE 4

N-(3-Acetamidopropyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A solution of the resultant compound from Example 3 (23.4 mg, 0.0326 mmol) in 5.4 mL CH₂Cl₂ was cooled to 0° C., and N-acetoxy-norbornene-2,3-dicarboximide (21.7 mg, 0.122 mmol) was added. The solution was stirred for 3 days at ambient temperature, then was concentrated and purified by preparative thin-layer chromatography (silica gel, 10% MeOH-1% concentrated aq. NH₄OH—CH₂Cl₂) provided 19.6 mg (0.0258 mmol, 79%) of the title compound as a white foam: mp 62°-67° C.; Rf 0.29 (10% MeOH-1% concentrated aq. NH₄OH—CH₂Cl₂); ¹H NMR (CDCl₃) δ0.65–1.95 (several bm, 29H approximately), 0.90 (t) and 0.92 (d, 9H total), 2.00 (s, 3H), 2.0–2.11 (m, 1H), 2.97 (m, 1H), 3.06 (dd, 1H), 3.1–3.5 (bm, 6H), 3.37 (s, 3H), 3.5–4.0 vbm, 6H), 4.52 (dd, 1H), 4.68 (s, 2H), 5.85 (d) and 5.93 (d, 1H total), 6.30 (bt, 1H), 6.48 (bt, 1H), 7.33 (bm, 5H); MS m/e 759 ((M+H)+). Anal. Calcd for C₄₂H₇₀N₄O₈·1.25 H₂O: C, 64.54; H, 9.34; N, 7.17. Found: C, 64.59; H, 9.02; N, 7.09.

EXAMPLE 5

N-(3-(2-Hydroxyethyl)amino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(3-(2-hydroxyethyl)amino)propyl) 2(S)-((3-(tert-butyloxycarbonyl)-2,2-dimethyl-4(S)-cyclohexylmethyl-5(S)-oxazolidinyl)methyl)-3-methylbutanamide.

The procedure of Example 2B was followed, using the following quantities: 2(S)-((3-(tert-butyloxycarbonyl-2,2-dimethyl-4(S)-cyclohexylmethyl-5(S)-oxazolidinyl)methyl)-3-methylbutanoic acid (European Patent Application No. EP364804, published Apr. 25, 1991) (100 mg, 0.243 mmol), HOBT (55.8 mg, 0.364 mmol), N-methylmorpholine (37 mg, 0.364 mmol) and 3-(2-(hydroxyethyl)aminopropylamine (37.3 mg, 0.316 mmol, prepared according to the procedure of Surrey, H. J. Am. Chem. Soc. 1950, 72, 1814) and EDCI (65.2 mg, 0.340 mmol) in 2.4 mL DMF. Purification by flash chromatography (silica gel, 10% MeOH-0.5% concentrated aq. NH₄OH—CH₂Cl₂) gave 80.6 mg (0.158 mmol, 65%) of the title compound as a low-melting, hygroscopic solid; Rf 0.34 (10% MeOH-1% concentrated aq. NH₄OH—CH₂Cl₂); ¹H NMR (CDCl₃) δ0.94 (2d, 9H), 1.10–1.45 (vbm, 13H), 1.48 (s, 9H), 1.58 (bs, 3H), 1.6–1.9 (bm, 5H), 2.0–2.1 (bm, 1H), 2.28 (bs, 4H), 2.75 (t, 2H), 2.82 (m, 2H), 3.40 (dd, 2H), 3.57–3.8 (m, 4H), 6.35 (bt, 1H).

B. The procedure of Example 2C was followed, in which the resultant compound from Example 5A was deprotected and coupled to the resultant compound from Example 1. For Part 1, the following quantities were used: the resultant compound from Example 5A (33 mg, 0.0645 mmol) was deprotected in 1 mL CH₂Cl₂ and 1 mL trifluoroacetic acid, followed by removal of the acetonide in 1.5 mL THF and 0.75 mL H₂O, to give 19.6 mg of crude amino alcohol. For Part 2, the following quantities were used: crude amino alcohol (15.0 mg, 0.040 mmol), HOBT (7.1 mg, 0.045 mmol), the resultant compound from Example 1 (18.1 mg, 0.044 mmol), N-methylmorpholine (4.5 mg, 0.045 mmol) and EDCI (10.9 mg, 0.56 mmol) were reacted in 1 mL DMF. Purification by preparative thin-layer chromatography (silica gel, 15% MeOH-0.5% concentrated aq. NH₄OH—CH₂Cl₂) produced 7.5 mg (0.010 mmol, 25%) of a hygroscopic glass; Rf 0.0.34 (15% MeOH-0.5% concentrated aq. NH₄OH—CH₂Cl₂); ¹H NMR (CDCl₃) δ0.65–1.93 (several bm, 28H approximately), 0.87–0.965 (m, 9H), 2.05 (m, 1H), 2.5–2.9 (bm, 9H, includes H₂O), 2.9–3.1 (m, 4H), 3.1–3.35 (bm, 4H), 3.37 (2s, 3H), 3.41–3.58 (bm, 4H), 3.68–4.1 (bm, 7H), 4.61 (bm, 1H), 4.68 (d, 2H), 5.78 (d) and 5.86 (d, 1H total), 6.90–7.13 (bm, 1H), 7.3–7.4 (bm, 5H); MS m/e 761 ((M+H)+).

EXAMPLE 6

N-(3-(Aminocarbonylamino)propyl) 5(S)-2(S)-(1(S)-(4-(methoxymethoxy)piperidin-1-yl)carbonyl-2,phenyl)-ethoxyhexanamido)-6-cyclohexyl-4(S)-hydroxy-2(S)-isopropylhexanamide A. N-(3-Aminopropyl) 2(S)-((3-(tert-butyloxycarbonyl)-2,2-dimethyl-4(S)-cyclohexylmethyl-5(S)-oxazolidinyl)methyl)-3-methylbutanamide.

The title compound from Example 2B (1.02 g, 1.70 mmol) was dissolved in 100 mL EtOAc containing 10% palladium on carbon catalyst (0.10 g, 0.094 mmol). The mixture was shaken under a pressure of 4 atmospheres of hydrogen at ambient temperature for 24 hours. The catalyst was removed by filtration through Celite and the filtrate was concentrated to a sticky glass. Purification by flash chromatography (silica gel, 10% MeOH-0.5% concentrated aq. NH₄OH—CH₂Cl₂) provided 641 mg (1.37 mmol, 81%) of the title compound as a hygroscopic sticky white foam; Rf 0.26 (10% MeOH-1% concentrated aq. NH₄OH—CH₂Cl₂); ¹H NMR (CDCl3) δ0.94 (m, 8H), 1.1–1.5 (vbm, 4H), 1.48 (s, 9H), 1.54–1.90 (several m, 20H), 2.04 (m, 1H), 2.81 (m, 2H), 3.49 (m, 2H), 3.64 (bm, 1H), 3.74 (m, 1H), 6.18 (m, 1H).

B. N-(3-(Aminocarbonylamino)propyl) 2(S)-((3-(tert-butyloxycarbonyl)-2,2-dimethyl-4(S)-cyclohexylmethyl-5(S)-oxazolidinyl)methyl)-3-methylbutanamide.

The resultant compound from Example 6A (125 mg,0.267 mmol) was dissolved in 4 mL dry THF and trimethylsilyl isocyanate (46.2 mg, 0.401 mmol) was added dropwise. The resulting solution was stirred overnight (18 h) at ambient temperature under a nitrogen atmosphere and then concentrated to a white foam. Purification by flash chromatography (silica gel, 4% MeOH—CH$_2$Cl$_2$) provided 111 mg (0.218 mmol, 82%) of the title compound as a white foam; Rf 0.56 (10% MeOH-1% concentrated aq. NH$_4$OH—CH$_2$Cl$_2$); $^1$H NMR (CDCl$_3$) δ0.95 (m, 8H), 1.10–1.45 (m, 5H), 1.48 (s, 9H), 1.52–1.90 (several m, 17H), 2.10 (m, 1H), 3.23 (m, 2H), 3.37 (m, 2H), 3.67 (bm, 1H), 3.73 (m, 1H), 4.40 (bs, 2H), 5.53 (bs, 1H), 6.08 (m, 1H).

C. The procedure of Example 2C was followed, in which the resultant compound from Example 6B was deprotected and coupled to the resultant compound from Example 1. For Part 1, the following quantities were used: the resultant compound from Example 6B (83 mg, 0.162 mmol) was deprotected in 2 mL CH$_2$Cl$_2$ and 2 mL trifluoroacetic acid, followed by removal of the acetonide in 3 mL THF and 1.5 mL H$_2$O, to give 55.3 mg of crude amino alcohol as a sticky white solid; Rf 0.09 (20% MeOH-1% concentrated aq. NH$_4$OH—CH$_2$Cl$_2$); $^1$H NMR (CDCl$_3$) δ0.95 (m, 9H), 1.05–2.25 (several m, 18H), 2.63 (m, 1H), 3.01–3.36 (several m, 5H), 3.43 (m, 1H), 4.73 (bs, 2H), 5.65 (m, 1H), 6.47 (m, 1H). For Part 2, the following quantities were used: crude amino alcohol (48.0 mg, 0.130 mmol), HOBT (22.8 mg, 0.149 mmol), the resultant compound from Example 1 (58.1 mg, 0.142 mmol), N-methylmorpholine (14.4 mg, 0.192 mmol) and EDCI (34.8 mg, 0.181 mmol) were reacted in 1.3 mL DMF. Purification by flash chromatography (silica gel, 5% MeOH—CH$_2$Cl$_2$) provided 69.0 mg of the title compound as a white powder; mp 87°–92° C.; Rf 0.58 (15% MeOH—CH$_2$Cl$_2$); $^1$H NMR (CDCl$_3$) δ0.65–2.10 (several m, 33H), 0.93 (m, 9H), 2.92–3.35 (several m, 6H), 3.37 (s, 3H), 3.41–3.63 (m, 3H), 3.68–3.87 (m, 3H), 3.87–4.05 (bm, 1H), 4.60 (m, 1H), 4.69 (s, 2H), 5.75 (bm, 1H), 5.80 (m, 1H), 6.44 (m, 1H), 7.33 (m, 5H); MS m/e 760 ((M+H)$^+$). Anal. Calcd for C$_{41}$H$_{69}$N$_5$O$_8$·1.0 H$_2$O: C, 63.29; H, 9.20; N, 9.00. Found: C, 63.28; H, 9.02; N, 8.85.

EXAMPLE 7

N-(3-(Aminothionylamino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(3-(Aminothionylamino)propyl 2(S)-((3-(tert-butyloxycarbonyl)-2,2-dimethyl-4(S)-cyclohexylmethyl-5(S)-oxazolidinyl)methyl)-3-methylbutanamide.

To a solution of the resultant compound from Example 6A (127 mg, 0.271 mmol) in 3.4 mL THF at 0° C. was added N,N'-thiocarbonyldiimidazole (67 mg, 0.338 mmol). The solution was allowed to warm to room temperature and stir 18 h. TLC (4% MeOH—CH$_2$Cl$_2$) indicated complete conversion to a new product. The yellow solution was recooled to 0° C. and treated with concentrated aq. NH$_4$OH (0.5 mL, 4 mmol). The reaction was stirred at room temperature for 48 h. The solution was concentrated in vacuo to a solid (210 mg), which was purified by flash chromatography (silica gel, 4% MeOH—CH$_2$Cl$_2$) to produce 134 mg (0.254 mmol, 94%) of a white solid; Rf 0.31 (5% MeOH—CH$_2$Cl$_2$); $^1$H NMR (CDCl$_3$) δ0.93 (d, 3H), 0.96 (d, 3H), 0.8–1.0 (bm, 2H), 1.05–1.5 (bm, 7H), 1.48 (s, 9H), 1.57 (bs), 1.66 (bs) and 1.55–1.90 (several bm, 15H total), 2.1 (bm, 1H), 3.30–3.42 (bm, 2H), 3.5–3.75 (bm, 4H), 5.72 (bs, 1H), 6.08 (bs, 1H), 7.45 (bs, 1H); MS m/e 527 ((M+H)$^+$).

B. Using the procedure of Example 2C, the resultant compound of Example 7a was deprotected and coupled to the resultant compound from Example 1 to provide the desired compound as a white solid (59%): mp 83°–89° C.; Rf 0.38 (5% MeOH—CH$_2$Cl$_2$); $^1$H NMR (CDCl$_3$) δ0.0.73 (br m, 2H), 0.8–1.0 (m, 10H), 1.05–1.94 (several br m, approximately 25H total), 2.0 (br m, 1H), 2.9–3.13 (m, 3H), 3.2 (br m, 1H), 3.25–3.4 (br m, 1H), 3.38 (2 s, 3H), 3.4–3.67 (br m, 4H), 3.72 (m, 1H), 3.75–3.9 (br m, 2H), 4.0 (br m, 1H), 4.62 (br m, 1H), 4.70 (2 s, 2H), 5.72 (dd, 1H), 6.18 (br s, 1H), 6.45 (br s, 1H), 7.33 (br s, 5H); MS m/e 776 ((M+H)$^+$). Anal. Calcd for C$_{41}$H$_{69}$N$_5$O$_7$S·0.75 H$_2$O: C, 62.37; H, 9.00; N, 8.87. Found: C, 62.38; H, 8.88; N, 8.87.

EXAMPLE 8

N-(2-cyanomethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(Cyanomethyl) 2(S)-((3-(tert-butyloxycarbonyl)-2;2-dimethyl-4(S)-cyclohexylmethyl-5(S)-oxazolidinyl)methyl)-3-methylbutanamide.

The procedure of Example 2B was used, substituting aminoacetonitrile hydrochloride for 3-(benzyloxycarbonylamino)propylamine. Purification by flash chromatography (silica gel, EtOAc-hexane 1:3) provided 513 mg (1.14 mmol, 94%) of the title compound as a white foamy solid: Rf 0.20 (EtOAc-hexane 1:3); $^1$H NMR (CDCl$_3$) δ0.94 (d, 3H), 0.97 (d, 3H), 0.85–1.05 (bm, 2H), 1.05–1.53 (several bm, 5H), 1.48 (s, 9H), 1.49 (s, 3H), 1.59 (s, 3H), 1.55–1.85 (several bm, 8H), 1.85–1.98 (m, 1H), 2.1–2.2 (bm, 1H), 3.55–3.75 (bm, 2H), 4.21 (ABX, 2H), 6.06 (bt, 1H).

B. The procedure of Example 2C can be used, in which the resultant compound from Example 8A is deprotected and coupled to the resultant compound from Example 1 to provide the desired compound.

EXAMPLE 9

2-Cyclohexyl-1(S)-(((4-(methoxymethoxy)piperidin-1-yl)carbonyl-2-phenyl)ethoxyhexanamido)ethyl-3(S)-isopropyl-2,3,4,5-tetrahydrofuran-2-one The resultant compound from Example 1 was coupled to (2S, 4S, 5S)-5-amino-6-cyclohexyl-4-hydroxy-2-isopropylhexanoic acid lactone (Bradbury, R. H.; Revill, J. M.; Rivett, J. E.; Waterson, D. *Tetrahedron Lett.* 1989, 3845) according to the procedure of Example 2C, Part 2, to obtain the desired product in 80% yield: $^1$H NMR (CDCl$_3$) δ0.89 (m), 0.91 (d), and 1.0 (d, 9H total), 0.70–1.9 (several bm, 27H approximately), 2.1 (m, 1H), 2.45 (m, 2H), 2.85 (m, 1H), 3.05 (dd, 1H), 3.5–3.8 (m, 4H), 4.5 (m, 1H), 4.7 (d, 2H), 5.35 (d) and 5.45 (d, 1H total), 7.4 (bm, 5H); MS m/e 643 ((M+H)$^+$).

EXAMPLE 10

N-(2-amino-2-methylpropyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The resultant compound from Example 9 (50.3 mg, 0.0782 mmol) was combined with 1,2-diamino-2-methylpropane (138 mg, 1.56 mmol) and the mixture was warmed to 60° C. for 3 days. The reaction mixture was partitioned between 20 mL EtOAc and 10 mL water. The organic phase was washed sequentially with 5 mL water, 10 mL brine, then dried (Na$_2$SO$_4$), filtered, and concentrated in vacuo to yield 52.6 mg of white solid. The crude product was purified by preparative TLC (10% MeOH-0.5% concentrated aq. NH$_4$OH—CH$_2$Cl$_2$) to produce 41.6 mg (0.0569 mmol, 73% of a foamy solid: mp 48°–56° C.; Rf 0.44 (15% MeOH-1% concentrated aq. NH$_4$OH—CH$_2$Cl$_2$); $^1$H NMR (CDCl$_3$) δ0.88–0.97 (m, 9H), 1.14 (s), 1.16 (s) and 0.6–2.2 (several bm, 33H approximately), 2.93–3.2 (bm, 4H), 3.2–3.46 (bm, 4H), 3.36 (s, 3H), 3.46–3.6 (bm, 1H), 3.6–3.95 (several bm, 4H), 4.50 (dd, 1H), 4.67 (AB, 2H), 5.85 (d) and 5.94 (d, 1H total), 6.28 (bs, 1H), 7.32 (bm, 5H); MS m/e 731 ((M+H)$^+$)).

EXAMPLE 11

N-(3-(4-Morpholino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A mixture of the resultant product from Example 9 (60 mg, 0.093 mmol) and 3-(4-morpholino)propylamine (150 mg, 1.04 mmol) was stirred at 60°–65° C. for 32 h. The mixture was diluted with EtOAc and washed with water. The organic portion was dried, filtered and evaporated. The residue was column chromatographed (silica gel, 2 to 5% MeOH—CHCl$_3$), providing 73 mg (0.058 mmol, 62%) of the desired product. The product obtained from this procedure is spectroscopically identical to the compound prepared previously (PCT Patent Application WO 90/03971, 19-4-90).

EXAMPLE 12

N-(4-(4-Morpholino)butyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2-(S)-isopropylhexanamide A. 4-(4-Morpholino)butylamine.

A mixture of 4-chlorobutyronitrile (4.23 g, 40.86 mmol) and morpholine (10.68 g, 122.59 mmol) was stirred at room temperature until the mixture solidified. It was diluted with EtOAc, washed with water. The organic portion was dried, filtered and evaporated to obtain 4.0 g (25.3 mmol, 65%) of a yellowish liquid: $^1$H NMR (CDCl$_3$) δ1.85 (q, 2H), 2.45 (m, 8H), 3.7 (m, 4H); MS m/e 155 (((M+H)$^+$). 2.0 g (13 mmol) of the above resultant liquid was hydrogenated under 4 atmospheres hydrogen with ethanolic ammonia and Raney nickel for 16 h. The mixture was filtered and the filtrate was evaporated to obtain 1.5 g (9.5 mmol, 73%) of the desired product: $^1$H NMR (CDCl$_3$) δ1.55–1.8 (m, 4H), 2.5 (m, 8H), 3.75 (m, 4H); MS m/e 159 (((M+H)$^+$). For literature procedure, see J. Amer. Chem. Soc. 1941, 63, 156.

B. The title compound was prepared according to the procedure of Example 10 by replacing 3-(4-morpholino)propylamine with the resultant compound from Example 12A, to produce the desired amide (55% yield): $^1$H NMR (CDCl$_3$) δ0.90 (m, 9H), 0.70–1.90 (several br m, 30H total), 2.02 (m, 1H), 2.35 (br m, 6H), 2.95 (m, 1H), 3.05 (dd, 1H), 3.20 (br m, 2H), 3.40 (s, 3H), 3.60–4.0 (several br m, 10H total), 4.50 (dd, 1H), 5.78(d) and 5.85 (d, 1H total), 6.20 (bt, 1H), 7.30 (br m, 5H); MS m/e 802 ((M+H)$^+$).

EXAMPLE 13

N-(5-(4-Morpholino)pentyl) 5(S)-(2(S)-(1-(S)-(4-(methoxymethoxy)piperidin-1-yl)carbonyl-2-phenyl)ethoxyhexanamido)-6-cyclohexyl-4(S)-hydroxy-2-(S)-isopropylhexanamide A. 5-(4-morpholino)pentylamine.

The title compound may be prepared according to the procedure of Example 12A, by substituting 5-chloropentanonitrile for 4-chlorobutyronitrile.

The title compound may be prepared according to the procedure of Example 10 by replacing 3-(4-morpholino)propylamine with the resultant product of Example 13A.

EXAMPLE 14

N-(3-(3-Oxa-9-azabicyclo[3.3.1]nonan-9-yl)propyl) 5(S)-(2(S)(1-(S)-(4-(methoxymethoxy)piperidin-1-yl)carbonyl-2-phenyl)ethoxyheanamido)-6-cyclohexyl-4(S)-hydroxy-2-(S)-isopropylhexanamide A. 3-(3-Oxa-9-azabicyclo [3.3.1]nonan-9-yl)propylamine.

This compound can be prepared according to the procedure of Example 12A, but replacing morpholine with 3-oxa-9-azabicyclo [3.3.1 ]nonane.

B. The title compound can be prepared according to the procedure of Example 10 by replacing 3-(4-morpholino)propylamine with the resultant amine from Example 14A.

EXAMPLE 15

N-(3-(3-Oxa-8-azabicyclo[3.2.1]octan-8-yl)propyl) 5(S)-(2(S)-(1-(S)-4-(methoxymethoxy)piperidin-1-yl)carbonyl-2-phenyl)ethoxyhexanamido)-6-cyclohexyl-4(S)-hydroxy-2-(S)-isopropylhexanamide A. 3-(3-Oxa-8-azabicyclo [3.2.1]octan-8-yl)propylamine.

This compound can be prepared according to the procedure of Example 12A, by replacing morpholine with 3-oxa-8-aza bicyclo [3.2.1]octane.

B. The title compound can be prepared according to the procedure of Example 10 by replacing 4-(3-aminopropyl)morpholine with the resultant amine from Example 15A.

EXAMPLE 16

N-(2-Aminoethyl) 5(S)-(2(S)-(1-(S)-(4-(methoxymethoxy)piperidin-1-yl)carbonyl-2-phenyl)ethoxyhexanamido)-6-cyclohexyl-4(S)-hydroxy-2-(S)-isopropylhexanamide The title compound was prepared according to the procedure of Example 10 by replacing 4-(3-aminopropyl)morpholine with 1,2-diaminoethane: as a white foam (87% yield): mp 62°–67° C.; Rf 0.28 (10% MeOH-1% conc aq. NH$_4$OH—CH$_2$Cl$_2$ ); $^1$H NMR (CDCl$_3$) δ0.67–1.92 (several br m, approx. 35 H ), 2.08 (m, 1H), 2.37–4.00 (several br m, approx. 17 H ), 3.37 (s, 3H), 4.54 (m, 1H), 4.68 (s, 2H), 5.83 (dd, 1H), 6.3 6 (m, 1H), 7.28–7.38 (m, 5H); MS m/e 703 ((M+H)$^+$). Anal. Calcd for C$_{39}$H$_{66}$N$_4$O$_7$.0.5 H$_2$O: C, 65.79; H, 9.48; N, 7.86. Found: C, 65.68; H, 9.27; N, 7.85.

EXAMPLE 17

N-(4-Aminobutyl)
5(S)-(2(S)-(1-(S)-(4-(methoxymethoxy)piperidin-1-yl)carbonyl-2-phenyl)ethoxyhexanamido)-6-cyclohexyl-4(S)-hydroxy-2-(S)-isopropylhexanamide The title compound was prepared according to the procedure of Example 10 by replacing 4-(3-aminopropyl)morpholine with 1,4-diaminobutane: mp 88°–90° C.; $^1$H NMR (CDCl$_3$) δ0.80–0.90 (m, 9H), 1.05–1.80 (br m, 30H), 2.13 (dd, 1H), 2.58 (br t, 2H), 3.00 (m, 4H), 3.20–3.65 (m, approx. 7H), 3.75 (m, 2H), 3.85 (m, 1H), 4.50 (m, 2H), 4.60 (br s, 2H), 6.72 (d, 1H), 6.76 (d, 1H), 7.25 (br s, 5H), 7.80 (m, 2H); MS m/e 732 ((M+H)+).

EXAMPLE 18

N-(5-Aminopentyl)
5(S)-(2(S)-(1-(S)-(4-(methoxymethoxy)piperidin-1-yl)carbonyl-2-phenyl)ethoxyhexanamido)-6-cyclohexyl-4(S)-hydroxy-2-(S)-isopropylhexanamide The title compound can be prepared according to the procedure of Example 10 by replacing 4-(3-aminopropyl)morpholine with 1,5-diaminopentane.

EXAMPLE 19

N-(3-Amino-3-methylbutyl)
5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. 1-Azido-2-(benyloxycarbonylamino)-2-methylbutane.

2-(Benyloxycarbonylamino)-2-methyl-1-butanol (1.358 g, 5.722 mmol) and triphenylphosphine (1.800 g, 6.86 retool) were dissolved in 10 mL CH$_2$Cl$_2$, and the resulting solution was cooled to 0° C. A solution of hydrazoic acid (prepared from sodium azide (1.30 g, 20.0 mmol), 0.533 mL concentrated sulfuric acid and 1.3 mL water) in 20 mL CH$_2$Cl$_2$ was passed through a plug of MgSO$_4$, the filtrate was added to the above alcohol solution, then diisopropyl azodicarboxylate (1.35 mL, 1.40 g, 6.91 mmol) was added dropwise over 3 min. The reaction mixture was stirred at 0° C. for 1 h, then at room temperature for 5 h. The mixture was concentrated in vacuo, and the residue was applied to 300 g of silica gel in a fritted disc funnel and eluted with 3×500 mL of 10% EtOAc-hexane. The second fraction contained pure desired azide (0.822 g, 3.13 mmol, 55%) as a colorless oil: Rf 0.17 (10% EtOAc-hexane); $^1$H NMR (CDCl$_3$) δ1.33 (s, 6H), 2.02 (bt, J=7.5 Hz, 2H), 3.32 (bt, J=7.5 Hz, 2H), 4.74 (br s, 1H), 5.05 (s, 2H), 7.3–7.4 (m, 5H); MS m/e 263 ((M+H)+), 280 (M+NH$_4$)+).

B. N-(3-Amino-3-methylbutyl) 2(S)-((3-(tert-butyloxycarbonyl)-2,2-dimethyl-4(S)-cyclohexylmethyl-5(S)-oxazolidinyl)methyl)-3-methylbutanamide.

The resultant compound from Example 19A (102 mg, 0.389 mmol) was stirred with 10% palladium on carbon (20 mg) in 1 mL EtOAc under 1 atm H$_2$ for 17 h. The solvent was removed with a stream of N$_2$, the residue was suspended in 3 mL MeOH, and then a solution of HCl in dioxane (0.16 mL, 4.8M, 0.768 mmol) was added. After stirring for 1 h, the mixture was filtered through celite, and the filtrate was rotoevaporated and the residue placed under high vacuum to produce the corresponding diamine dihydrochloride (72 mg, 0.40 mmol, 103%) as a white foamy solid: $^1$H NMR (CD$_3$OD) δ1.40 (s, 6H), 2.04 (m, 2H), 3.06 (m, 2H). The above crude diamine dihydrochloride (60.2 mg, 0.344 mmol) was coupled according to the procedure of Example 2B to provide (after flash chromatography, eluting with 12.5% MeOH-1% concentrated aq. NH$_4$OH—CH$_2$Cl$_2$) the title compound (85.5 mg, 0.186 mmol, 67%) as a glass: Rf 0.34 (10% MeOH-1% concentrated aq. NH$_4$OH—CH$_2$Cl$_2$); $^1$H NMR (CDCl$_3$) δ0.93 (2 d, 6H), 1.17 (2s, 6H), 1.48 (s, 9H), 0.8–1.8 (several br m, approximately 23H total), 1.85 (m, 1H), 2.02 (m, 1H), 3.36 (m, 1H), 3.44 (m, 1H), 3.64 (br m, 1H), 3.76 (m, 1H), 6.96 (bt, 1H); MS m/e 496 ((M+H)+).

C. The procedure of Example 2C was used. The resultant compound from Example 19B (73.5 mg, 0.148 mmol) was deprotected to give 55.5 mg (01156 mmol, 105%) of the corresponding crude diamino alcohol as a yellow viscous oil: $^1$H NMR (CDCl$_3$) δ0.93 (2 d) and 0.75–1.05 (br m, 9H total), 1.15 (s, 6H), 1.05–1.9 (several br m, approximately 24H), 2.09 (m, 1H), 2.60 (br m, 1H), 3.39 (m, 2H), 7.09 (br m, 1H) ; MS m/e 356 ((M+H)+). The crude amino alcohol was then coupled using the following quantities: crude diamino alcohol (52.4 mg, 0.127 mmol), the resultant compound from Example 1 (55.0 mg, 0.134 mmol), HOBT (31.2 mg, 0.204 mmol), N-methylmorpholine (28 mL, 26 mg, 0.255 mmol) and EDCI (32 mg, 0.167 mmol) in 0.6 mL DMF. Purification by flash chromatography (10% MeOH-0.5% concentrated aq. NH$_4$OH—CH$_2$Cl$_2$) produced 59.0 mg (0.079 mmol, 62%) of the title compound as a white foam: mp 44°–49° C.; $^1$H NMR (CDCl$_3$) δ0.86–0.95 (m, 10H), 1. 195–1.21 (2 s, 6H), 0.65–2.5 (several br m, approximately 33H), 2.96 (m, 1H), 3.04 (dd, 1H), 3.36 (s, 3H), 3.72 (t, 2H), 3.1–4.0 (several br m, approximately 8H total), 4.57 (m, 1H), 4.68 (s, 2H), 5.85 and 5.91 (2 d, 1H total), 7.32 (br s, 5H), 7.41 (br m, 1H) ; MS m/e 745 ((M+H)+). Anal. Calcd for C$_{42}$H$_{72}$N$_4$O$_7$.1.5 H$_2$O: C, 65.34; H, 9.79; N, 7.26. Found: C, 65.57; H, 9.41; N, 7.24.

EXAMPLE 20

N-(2-Ureido)ethyl
5(S)-(2(S)-(1(S)-(4-(methoxymethoxy)piperidin-1-yl) carbonyl-2-phenyl)ethoxyhexanamido)-6-cyclohexyl-4(S)-hydroxy-2(S)-isopropylhexanamide The procedure of Example 6B was used, substituting the resultant product from Example 16 for the resultant product from Example 6A, to provide the title compound as a white powder (39% yield): mp 85°–92° C.; Rf 0.43 (10 % MeOH—CH$_2$Cl$_2$); $^1$H NMR (CDCl$_3$) δ0.55–1.98 (several br m, 36H approximately), 2.84–3.88 (several br m, 14H), 3.38 (d, 3H), 3.95–4.18 (br m, 1H), 4.68 (s, 2H), 4.71 (br m, 1H), 5.09 (br m, 2H), 5.50 (br m, 1H), 5.66 (dd, 1H), 6.22 (br m, 1H), 7.27–7.38 (br m, 5H); MS m/e 746 ((M+H)+). Anal. Calcd for C$_{40}$H$_{67}$N$_5$O$_8$.1.25 H$_2$O: C, 62.51; H, 9.11; N, 9.11. Found: C, 62.38; H, 8.72; N, 8.95.

EXAMPLE 21

N-(2-(Thioureido)ethyl
5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 7A was used, substituting the resultant product from Example 16 for the resultant product from Example 6A, to provide the title compound as a white powder (52% yield): mp 98°–112° C.; Rf 0.40 (5% MeOH—CH$_2$Cl$_2$); $^1$H NMR (CDCl$_3$) δ0.51–1.96 (several br m, 37H approximately), 2.81–4.26 (several br m, 15H), 3.48 (d, 3 H), 4.69 (s, 2H), 4.74 (m, 1H), 5.64 (dd, 1H), 6.19 (m, 1H), 6.52 (m, 1H), 6.92 (m, 1H), 7.29–7.40 (m, 5H); MS m/e 7 62 ((M+H)+). Anal. Calcd for C40H67N5 O7S: C, 63.04; H, 8.86; N, 9.19. Found: C, 62.95; H, 8.63; N, 9.03.

EXAMPLE 22

N-(2-(Benzyloxycarbonylamino)ethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(2-Aminoethyl) benzylcarbamate.

A solution of ethylenediamine (33.4 mL, 30.0 g, 0.500 mmol) in 300 mL CHCl3 was cooled to 0° C. and a solution of N-(benzyloxycarbonyloxy)succinimide (5.0 g, 20.1 mmol) in 150 mL CHCl3 was added dropwise over 5 h. The resulting solution was stirred at room temperature overnight. The reaction was extracted with water (5×500 mL) and brine (500 mL), dried (Na2SO4), filtered and concentrated in vacuo to provide the title compound (2.58 g, 13.3 mmol, 66%) as a colorless oil (which solidified upon standing): 1H NMR (CDCl3) δ2.81 (m, 2H), 3.24 (m, 2H), 5.10 (s, 2H), 5.25 (br s, 1H), 7.25–7.40 (m, 5H).

B. N-(2-Benzyloxycarbonylamino)ethyl 2(S)-((3-(tert-butyloxycarbonyl)-2,2-dimethyl-4(S)-cyclohexylmethyl-5(S)-oxazolidinyl)methyl)-3-methylbutanamide.

The resultant compound from Example 1 (1.50 g, 3.64 mmol), HOBT (0.837 g, 5.45 mmol), and N-methylmorpholine (0.600 mL, 0.55 g, 5.45 mmol) were dissolved in 36.5 mL DMF, and the resulting solution was cooled to −15° C. EDCI (978 mg, 5.10 mmol) was added as a solid. The mixture was stirred at −15° C. for 6 h, after which the vessel was sealed and allowed to stand at 0° C. for 24 h. The resultant compound from Example 22A (885 mg, 4.56 mmol) was added to the solution of active ester, and the resulting solution was stirred at −23° C. for 5 h and an additional 24 h at room temperature. The reaction mixture was concentrated by distillation under high vacuum, and the residue was partitioned between 250 mL 80% saturated NaHCO3 and 250 mL CH2Cl2. The organic phase was washed sequentially with 250 mL 80% sat. aq. NaHCO3, 250 mL water and 250 mL brine, dried (Na2SO4), filtered and concentrated in vacuo. Purification by flash chromatography (35% EtOAc-hexane) produced 2.017 g (3.43 mmol, 94%) of the title compound as a white powder: 1H NMR (CDCl3) δ0.8–1.0 (br m, 8H), 1.48 (s), 1.57 (bs), 1.63 (bs) and 1.0–1.95 (several br m, approximately 31H total), 2.02 (br m, 1H), 3.34 (br m, 3H), 3.46 (br m, 1H), 3.56–3.7 (br m, 1H), 3.72 (br m, 1H), 5.09 (s, 2H), 5.47 (br m, 1H), 5.99 (br m, 1H), 7.3 (br m, 5H); MS m/e 588 ((M+H)+).

C. The procedure of Example 2C was employed, with the substitution of the resultant compound from Example 22B for the resultant compound from Example 2B, to provide the title compound: mp 65°–72° C.; Rf 0.51 (5% MeOH—CH2Cl2); 1H NMR (CDCl3) δ0.64–2.10 (several br m, approx. 36H), 2.95–3.00 (m, 1H), 3.04 (dd, 1H), 3.10–3.59 (br m), 3.35 (s) and 3.37 (s, 13H total), 3.60–4.00 (br m, 4H), 4.46–4.57 (br m, 1H), 4.67 (s, 2H), 5.10 (s, 2H), 5.72–5.90 (br m, 2H), 6.10–6.20 (br m, 1H), 7.2–7.45 (m, 10H); MS m/e 837 ((M+H)+). Anal. Calcd for C47H72N4O9: C, 67.44; H, 8.67; N, 6.69. Found: C, 67.33; H, 8.79; N,.

EXAMPLE 23

N-(2-Acetamidoethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 4 was employed, with the substitution of the resultant compound from Example 16 for the resultant compound from Example 3, to provide the title compound as a white powder (26% yield): mp 95°–99° C.; Rf 0.18 (5% MeOH—CH2Cl2); 1H NMR (CDCl3) δ0.87–0.96 (overlapping t and 2 d) and 0.65–1.07 (br m, 8H total), 1.07–1.90 (several br m, approx. 26H), 1.99 (s) and 1.95–2.06 (br m, 4H total), 2.94 (dd, 1H), 3.05 (dd, 1H), 3.13–3.35 (br m, 4H), 3.38 (s, 3H), 3.40–3.58 (br m, 5H), 3.65–3.92 (br m, 3H), 3.92–4.02 (br m, 1H), 4.49–4.57 (br m, 1H), 4.68 (s, 2H), 5.77 (2 br d, 1H), 6.18–6.27 (br m, 1H), 6.78–6.84 (br m, 1H), 7.32 (br s, 5H); MS m/e 745 ((M+H)+). Anal. Calcd for C41H68N4O8.0.75 H2O: C, 64.92; H, 9.23; N, 7.38. Found: C, 64.97; H, 9.16; N, 7.39.

EXAMPLE 24

N-(2-(S-Methyl-N'-cyanoisothioureido)ethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The compound resulting from Example 16 (255.4 mg, 0.3633 mmol) and dimethyl N-cyanodithioiminocarbonate (69.1 mg, 0.4732 mmol, 30% excess) were combined in acetonitrile (8 mL) and heated at reflux (90° C. oil bath) for 36 hours under nitrogen. The reaction mixture was concentrated under reduced pressure, and the residue obtained was chromatographed on a silica gel column eluting with 3.5% methanol in methylene chloride to afford the title compound as a white amorphous solid (180 mg, 62%): mp 72°–82° C.; Rf 0.29 (5% MeOH—CH2Cl2); 1H NMR (CDCl3) δ0.82–0.98 (m) and 0.65–1.95 (several br m, approx. 38H total), 1.99–2.09 (m, 1H), 2.55 (br s, 3H), 2.94 (dd, 1H), 3.03 (dd, 1H), 3.11–3.65 (br m) and 3.39 (2 s, 12H total), 3.72 (t) and 3.7–3.98 (br m, 4H total), 3.98–4.10 (br m, 1H), 4.52–4.66 (br m, 1H), 4.69 (s, 2H), 5.74–5.87 (m, 1H), 6.50–6.65 (br m, 1H), 7.33 (br s, 5H), 7.85–8.00 (br s, 1H); MS m/e 801 ((M+H)+). Anal. Calcd for C42H68N6O7S: C, 62.97; H, 8.55; N, 10.49. Found: C, 62.68; H, 8.66; N, 10.33.

EXAMPLE 25

N-(2-N'-Cyanoureido)ethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide To the compound resulting from Example 24 (75 mg, 0.0936 mmol) dissolved in ethanol (2 mL) was added ammonium hydroxide (732 μL, 18.724 mmol, 200 equivalents). The reaction vessel was sealed and heated at 90° C. for 72 hours. The reaction mixture was concentrated under reduced pressure to afford crude material (67.1 mg). Chromatography on silica gel eluting with 4% methanol in methylene chloride afforded the title compound as a white powder (35.7 mg, 50%): mp 92°–99° C.; Rf 0.53 (10% MeOH—CH2Cl2); 1H NMR (CDCl3) δ0.50–1.94 (several br m, 36H approximately), 2.82–4.15 (several br m, 15 H approximately), 3.48 (d, 3H), 4.65 (m, 1H), 4.71 (d, 2H), 5.60 (dd, 1H), 5.83 (m, 0.5H), 6.04

(m, 1H), 6.22 (m, 2H), 6.31 (m, 0.5H), 7.29–7.40 (m, 5H); MS m/e 770 ((M+H)+). Anal. Calcd for $C_{41}H_{67}N_7O_7$: C, 63.95; H, 8.77; N, 12.73. Found: C, 62.05; H, 8.38; N 13.03.

EXAMPLE 26

N-(2-(N-Methyl-N'-cyanoureido)ethyl) 5(S)-(2(S)-(1(S)-(4-(methoxymethoxy)piperidin-1-yl) carbonyl-2-phenyl)ethoxyhexanamido)-6-cyclohexyl-4(S)-hydroxy-2(S)-isopropylhexanamide The procedure of Example 25 can be employed, with the substitution of 40% aq. methyl amine for 30% aq. NH₄OH, to provide the title compound.

EXAMPLE 27

N-(2-((3-Amino-1H-1,2,4-triazol-5-yl)amino)ethyl) 2(S)-((3-(tert-butyloxycarbonyl)-2,2-dimethyl-4(S)-cyclohexylmethyl-5(S)-oxazolidinyl)methyl)-3-methylbutanamide The procedure of Example 25 was employed, with the substitution of hydrazine hydrate for 30% aq. NH₄OH, to provide the title compound as a white powder (69% yield): mp 99°–112° C.; Rf 0.42 (10% MeOH—CH₂Cl₂ w/1% conc NH₄OH added); ¹H NMR (CDCl₃) δ0.53–1.90 (several br m, 35H approximately), 1.99 (m, 1H), 2.50–5.00 (vbr m, 3H approximately), 2.88–4.10 (several br m, 15H), 3.38 (d, 3H), 4.68 (d, 2H), 4.71 (m, 1H), 5.11 (br s, 1H), 5.73 (dd, 1H), 6.78 (br s, 1H), 7.29–7.39 (m, 5H); MS m/e 785 ((M+H)+). Anal. Calcd for $C_{41}H_{68}N_8O_7 \cdot 1.0\ H_2O$: C, 61.32; H, 8.78; N, 13.95. Found: C, 61.47; H, 8.76; N 13.58.

EXAMPLE 28

N-(2-((5-Amino-1,2,4-oxadiazol-3-yl)amino)ethyl) 2(S)-((3-(tert-butyloxycarbonyl)-2,2-dimethyl-4(S)-cyclohexylmethyl-5(S)-oxazolidinyl)methyl)-3-methylbutanamide The procedure of Example 25 can be employed, with the substitution of hydroxylamine hydrochloride and a molar equivalent quantity of triethylamine for 30% aq. NH₄OH, to provide the title compound.

EXAMPLE 29

N-(5-(Tetrazolyl)methyl 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(5-(Tetrazolyl)methyl 2(S)-((3-(tert-butyloxycarbonyl)-2,2-dimethyl-4(S)-cyclohexylmethyl-5(S)-oxazolidinyl)methyl)-3-methylbutanamide A solution of the resultant compound from Example 8A (150 mg, 0.334 mmol), triethylamine hydrochloride (68.9 mg, 0.500 mmol) and sodium azide (65.1 mg, 1.00 mmol) in 3.3 mL DMF was warmed to 125° C. for 24 h. The dark solution was concentrated under high vacuum, and the resulting oil was poured into a mixture of 10 mL water and 10 mL CH₂Cl₂. The mixture was acidified to pH 1 with 1N HCl. The layers were stirred, then separated, and the aqueous phase was extracted with 2×20 mL CH₂Cl₂. The combined organic phases were washed with brine, dried (Na₂SO₄), filtered and concentrated in vacuo to produce 168 mg (0.341 mmol, 102%) of crude tetrazole: Rf 0.32 (5% MeOH-0.5% HOAc—CH₂Cl₂); ¹H NMR (CDCl₃) δ0.91 (d), 0.96 (d), and 0.8–1.0 (br m, 8H total), 1.49 (s, 9H), 1.55 (br s, 3H), 1.60 (br s, 3H), 1.0–1.98 (several br m, approximately 14H total), 2.16 (br m, 1H), 3.65–3.77 (m, 2H), 4.62 (dd, 1H), 5.03 (dd, 1H), 6.55 (bt, 1H); MS m/e 515 ((M+Na)+); HRMS Calcd for (M+Na)+ for $C_{25}H_{45}N_6O_4Na$: 516.3400. Found: 516.3333.

B. The procedure of Example 2C was followed, with the substitution of the resultant product from Example 29A for the resultant product from Example 2B, to provide the title compound as a white powder: mp 95°–123° C.; Rf 0.33 (15% MeOH-1% conc NH₄OH—CH₂Cl₂); ¹H NMR (CDCl₃) δ0.50–1.98 (several br m, 36H approximately), 2.24 (m, 1H), 2.20–3.00 (vbr m, 1H), 2.83–4.62 (several br m, 11H), 3.39 (d, 3H), 4.70 (d, 2H), 5.19 (br m, 1H), 5.49 (br m, 1H), 7.02 (br m, 2H), 9.19–7.36 (m, 5H); MS m/e 742 ((M+H)+). Anal. Calcd for $C_{39}H_{67}N_7O_7 \cdot 1.5\ H_2O$: C, 60.91; H, 8.65; N, 12.74. Found: C, 60.80; H, 8.21; N 12.01.

EXAMPLE 30

N-(2-Methyl-2-(4-morpholino)propyl) 5(S)-(2(S)-(1(S)-(4-(methoxymethoxy)piperidin-1-yl) carbonyl-2-phenyl)ethoxyhexanamido)-6-cyclohexyl-4(S)-hydroxy-2(S)-isopropylhexanamide Through a solution of dihydrofuran (15 μL, 14 mg, 0.198 mmol) dissolved in methanol (0.1 mL) and methylene chloride (0.4 mL) and cooled to −65° C. under argon was passed a stream of ozone/oxygen for approximately 30 seconds to give a pale blue solution. Oxygen was then bubbled through the solution to drive off the excess ozone and then sodium cyanoborohydride (6.9 mg, 0,110 mmol) was added. The reaction mixture was stirred at −65° C. to −60° C. for 25 minutes and then a solution of the compound resulting from Example 10 (33.4 mg, 0.0457 mmol) dissolved in methanol (0.6 mL) was added. The reaction mixture was stirred at −60° C. for 30 minutes, allowed to warm to 0° C., and then stirred at 0° C. for 6 hours. It was then allowed to warm to ambient temperature and stirred for 24 hours. The reaction mixture was partitioned between 1M sodium carbonate (10 mL) and methylene chloride (20 mL). The aqueous phase was extracted with methylene chloride (2×10 mL). The combined organic extracts were washed with brine (15 mL), dried over sodium sulfate, and concentrated in vacuo to afford crude product (36.1 mg). Preparative tlc on silica gel eluting with 4% methanol in methylene chloride afforded pure title compound as a white amorphous solid (26.3 mg, 58%): mp 46°–52° C.; Rf 0.24 (5% MeOH—CH₂Cl₂); ¹H NMR (CDCl₃) δ0.66–1.48 (br m), 0.91 (t), 0.92–0.97 (2 d) and 1.04 (s, 31H total), 1.49–1.90 (br m, 17H), 2.11–2.17 (m, 1H), 2.47–2.54 (m, 4H), 2.93–3.00 (m, 2H), 3.06 (dd, 1H), 3.11 (dd, 1H), 3.17–3.29 (br m, 3H), 3.37 (s) and 3.30–3.49 (br m, 5H), 3.64–3.84 (br m, 6H), 3.84–3.97 (br m, 1H), 4.49 (dd, 1H), 4.69 (s, 2H), 5.83 (d) and 5.90 (d, 1H total), 6.28 (br t, 1H), 7.38–7.48 (m, 5H); MS m/e 801 ((M+H)+). Anal. Calcd for $C_{45}H_{76}N_4O_8 \cdot H_2O$: C, 65.98; H, 9.60; N, 6.84. Found: C, 65.57; H, 9.18; N, 6.82.

EXAMPLE 31

N-(3-(S-Methyl-N'-cyanoisothioureido)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 24 was employed, with the substitution of the resultant compound from Example 3 for the resultant compound from Example 16, to provide the title compound as a white powder (84% yield): mp 88°–94° C.; Rf 0.49 (10% MeOH—CH₂Cl₂);

¹H NMR (CDCl₃) δ0.65–1.90 (several br m, approx. 37H), 2.08 (m, 1H), 2.59 (s, 3H), 2.90–4.04 several br m, 15H), 3.38 (s, 3H), 4.50 (m, 1H), 4.68 (s, 2H), 5.82 (dd, 1H), 6.21 (m, 1H), 7.27–7.39 (m, 5H), 7.89 (m, 1H); MS m/e 815 ((M+H)+). Anal. Calcd for $C_{43}H_{70}N_6O_7S.0.5-H_2O$: C, 62.67; H, 8.68; N, 10.20. Found: C, 62.83; H, 8.57; N, 10.20.

EXAMPLE 32

N-(3-(N-Methyl-N'-cyanoureido)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 25 was employed, with the substitution of 40% aq. methyl amine and the resultant compound from Example 31 for 30% aq. NH₄OH and the resultant compound from Example 24, to provide the title compound as a white powder (80% yield): mp 101°–107° C.; Rf 0.34 (7.5% MeOH—CH₂Cl₂); ¹H NMR (CDCl₃) δ0.64–1.93 (several br m, 37H approximately), 2.13 (m, 1H), 2.88 (d, 3H), 2.93–4.10 (several br m, 15H), 3.38 (d, 3H), 4.61 (m, 1H), 4.69 (s, 2H), 5.75 (dd, 1H), 5.90 br s, 1H), 6.31 (br s, 2H), 7.28–7.40 (br m, 5H); MS m/e 798 ((M+H)+), 815 ((M+NH₄)+). Anal. Calcd for $C_{43}H_{71}N_7O_7$: C, 64.71; H, 8.97; N, 12.28. Found: C, 64.35; H, 8.00; N, 12.15.

EXAMPLE 33

N-(3-(N'-cyanoureido)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 25 was employed, with the substitution of the resultant compound from Example 31 for the resultant compound from Example 24, to provide the title compound as a white foam (54% yield): mp 116°–126° C.; Rf 0.37 (7.5% MeOH—CH₂Cl₂); ¹H NMR (CDCl₃) δ0.51–1.93 (several br m, 38H), 2.00 (m, 1H), 2.90–3.91 (several br m, 13H), 3.39 (d, 3H), 4.00 (m, 1H), 4.61 (m, 1H), 4.70 (d, 2H), 5.71 (dd, 1H), 5.96 (m, 2H), 6.27 (m, 1H), 6.39 (m, 1H), 7.28–7.39 (m, 5H); MS m/e 784 ((M+H)+), 801 ((M+NH₄)+).

EXAMPLE 34

N-(3-((3-Amino-1H-2,4-triazol-5-yl)amino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 25 was employed, with the substitution of hydrazine hydrate and the resultant compound from Example 31 for 30% aq. NH₄OH and the resultant compound from Example 24, to provide the title compound as a white powder (91% yield): mp 110°–120° C; Rf 0.24 (10% MeOH-1% conc NH₄OH—CH₂Cl₂); ¹H NMR (CDCl₃) δ0.58–1.90 (several br m, 37H approximately), 2.11 (br m, 1H), 2.90–4.04 (several br m, 15H), 3.47 (d, 3H), 4.60 (m, 1H), 4.68 (d, 2H), 4.50–5.50 (v br m, 3H), 5.70 (dd, 1H), 7.13–7.43 (br m, 2H), 7.29 (m, 5H); MS m/e 799 ((M+H)+). Anal. Calcd for $C_{42}H_{70}N_8O_7.1.0 H_2O$: C, 61.74; H, 8.88; N, 13.71. Found: C, 61.76; H, 7.86; N, 13.56.

EXAMPLE 35

N-(3-((5-Amino-1,2,4-oxadiazol-3-yl)amino)propyl) 2(S)-(3-(tert-butyloxycarbonyl)-2,2-dimethyl-4(S)-cyclohexylmethyl-5(S)-oxazolidinyl)methyl)-3-methylbutanamide The procedure of Example 25 can be employed, with the substitution of the resultant compound from Example 31 and hydroxylamine hydrochloride and a molar equivalent quantity of triethylamine for the resultant compound from Example 24 and 30% aq. NH₄OH, to provide the title compound.

EXAMPLE 36

N-(3-(4-Oxido-4-morpholino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A solution of the resultant compound from Example 11 (44.1 mg, 0.056 mmol) in 0.22 mL MeOH was treated with 30% aq. H₂O₂ (17 mL, 5.7 mg H₂O₂, 0.16 mmol). The solution was stirred at ambient temperature for 4 d, then an additional 18 h at 50° C. The solution was concentrated and partitioned between 20 mL CHCl₃ and 10 mL of 1:1 water:brine. The aqueous phase was extracted (3×10 mL CHCl₃), the combined organic phases were washed with brine, dried (Na₂SO₄), filtered and concentrated to a foam. Preparative TLC (silica gel, 15% MeOH—CHCl₃) provided 24.8 mg (30.9 μmol, 55%) of the title compound as a white foam: mp 71°–83° C.; ¹H NMR (CDCl₃) δ0.60–2.20 (several br m) and 0.83–0.97 (m, approx. 38H total), 2.88–3.08 (br m, 3H), 3.08–3.25 (m, 3H), 3.25–3.55 (br m), 3.35 (s) and 3.37 (s, 11H total), 3.55–3.3.67 (br m, 2H), 3.67–3.95 (br m, 4H), 4.00–4.22 (br m, 1H), 4.26–4.40 (m, 2H), 4.53–4.63 (m, 1H), 4.67 (s) and 4.68 (s, 2H total), 5.70 (br t, 1H), 7.27–7.43 (m, 5H), 8.12–8.21 (br m, 1H); MS m/e 803 ((M+H)+). Anal. Calcd for $C_{44}H_{74}N_4O_9.1.5 H_2O$: C, 63.66; H, 9.35; N, 6.75. Found: C, 63.41; H, 9.03; N, 6.55.

EXAMPLE 37

N-(2-Carboxyethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-((2-(O-Ethyl)carboxy)ethyl) 2(S)-((3-(tert-butyloxycarbonyl)-2,2-dimethyl-4(S)-cyclohexylmethyl-5(S)-oxazolidinyl)methyl)-3-methylbutanamide.

The procedure of Example 2B was employed, with the substitution of β-alanine ethyl ester hydrochloride for the resultant compound from Example 2A, to provide the title compound oil (quantitative yield): Rf 0.55 (2.5% MeOH—CH₂Cl₂); ¹H NMR (CDCl₃) δ0.80–1.90 (several br m, 16H approximately), 0.92 (dd, 6H), 1.28 (t, 3H), 1.49 (s, 9H), 1.58 (br s, 3H), 1.64 (br s, 3H), 2.03 (m, 1H), 2.55 (m, 2H), 3.41–3.76 (several m, 4H), 4.16 (m, 2H), 6.12 (m, 1H); MS m/e 511 ((M+H)+), 528 ((M+NH₄)+).

B. N-(2-Carboxyethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S) isopropylhexanamide.

The procedure of Example 2C was employed, with the substitution of the resultant compound from Example 37A for the resultant compound from Example 2B, to provide the title compoundsemi-solid mass (61% yield): Rf 0.28 (5% MeOH—CH$_2$Cl$_2$); $^1$H NMR (CDCl$_3$) δ0.64–1.90 (several br m, 27H approximately), 0.91 (m, 9H), 1.29 (t, 3H), 2.06 (m, 1H), 2.55 (m, 2H), 2.91–3.96 (several br m, 12H), 3.37 (s, 3H), 4.18 (dq, 2H), 4.50 (m, 1H), 4.68 (s, 2H), 5.81 (dd, 1H), 6.20 (m, 1H), 7.28–7.38 (m, 5H); MS m/e 760 ((M+H)$^+$), 777 ((M+NH$_4$)$^+$). Anal. Calcd for C$_{42}$H$_{69}$N$_3$O$_9$.0.5 H$_2$O: C, 65.59; H, 9.17; N, 5.46. Found: C, 65.66; H, 8.91; N, 5.54.

C. To the compound resulting from Example 37B (125.7 mg, 0.1654 mmol) dissolved in tetrahydrofuran (2.5 mL) and cooled to 0° C. was added a solution of lithium hydroxide (13.9 mg, 0.3308 mmol) in water (0.3 mL). After stirring at 0° C. under nitrogen for 2 hours, the cooling bath was removed and stirring was continued for 2 hours at ambient temperature. The reaction mixture was diluted with water (10 mL) and concentrated under reduced pressure to remove the tetrahydrofuran. The aqueous solution was acidified to pH 2 with 1N sodium hydrogen sulfate (3 mL) and extracted with methylene chloride (4×20 mL). The combined organic extracts were washed with brine, dried over sodium sulfate, and concentrated under reduced pressure to afford crude product as an amorphous solid (112.7 mg). Chromatography on silica gel eluting with 3% methanol in methylene chloride containing 0.5% acetic acid afforded 80 mg of material. This material was further purified by preparative thin layer chromatography on silica gel eluting with 5% methanol in methylene chloride containing 0.5% acetic acid to afford the title compound as a white amorphous solid (53.1 mg, 44%): mp 115°–124° C.; Rf 0.45 (5% MeOH—CH$_2$Cl$_2$ w/1.0% HOAc added); $^1$H NMR (CDCl$_3$) δ0.33–2.05 (several br m, 37H approximately), 2.86–4.28 (several br m, 15H), 3.38 (d, 3H), 4.69 (d, 2H), 4.78 (m, 1H), 5.55 (br m, 1H), 7.05–7.80 vbr m, 1H), 7.27–7.48 (m, 5H); MS m/e 754 ((M+Na)$^+$); (FAB$^-$) m/e 730 ((M−H)$^-$).

EXAMPLE 38

N-(2-Cyanoethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(2-Cyanoethyl) 2(S)-((3-(tert-butyloxycarbonyl)-2,2-dimethyl-4(S)-cyclohexylmethyl-5(S)-oxazolidinyl)methyl)-3-methylbutanamide.

The procedure of Example 2B can be followed, with the substitution of 2-aminopropionitrile hydrochloride plus an additional equivalent of N-methylmorpholine for (benzyloxycarbonylamino)propylamine, to provide the title compound.

B. The procedure of Example 2C can be followed, with the substitution of the resultant product from Example 38A for the resultant product from Example 2B, to provide the title compound.

EXAMPLE 39

N-(2-(5-(Tetrazolyl)ethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-(2-(5-(Tetrazolyl)ethyl) 2(S)-((3-(tert-butyloxycarbonyl)-2,2-dimethyl-4(S)-cyclohexylmethyl-5(S)-oxazolidinyl)methyl)-3-methylbutanamide.

The procedure of Example 29A can be followed, with the substitution of the resultant product from Example 38A for the resultant product from Example 8A, to provide the title compound.

B. The procedure of Example 2C may be followed, with the substitution of the resultant product from Example 39A for the resultant product from Example 2B, to provide the title compound.

EXAMPLE 40

N-(N'-cyanoureido) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. N-Amino 5(S)-( 2(S)-(1(S)-(4-(methoxymethoxy)piperidin-1-yl)carbonyl-2-phenyl)ethoxyhexanamido)-6-cyclohexyl-4(S)-hydroxy-2(S) isopropylhexanamide.

The procedure of Example 10 may be followed, with the substitution of hydrazine hydrate for 1,2-diamino-2-methylpropane, to give the desired compound.

B. N-(S-Methyl-N'-cyanoisothioureido) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide.

The procedure of Example 24 can be employed, with the substitution of the resultant compound from Example 40A for the resultant compound from Example 16, to provide the title compound.

C. The procedure of Example 25 can be employed, with the substitution of the resultant compound from Example 40B for the resultant compound from Example 24, to provide the title compound.

EXAMPLE 41

N-13-Amino-1H-1,2,4-triazol-5-yl)amino) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide The procedure of Example 25 can be employed, with the substitution of the resultant compound from Example 40B and hydrazine hydrate for the resultant compound from Example 24 and 30% aq. NH$_4$OH, to provide the title compound.

EXAMPLE 42

N-(6-Cyclohexyl-2,2-difluoro-1-dimethylamino-3(R); 4(R)-dihydroxyhexan-5(S)-yl) 2(S)-(1(S)-(4-(methoxymethoxy)piperidin-1-yl-carbonyl)phenylethoxy)hexanamide A. (4S,5R,1'R)-3-(tert-Butyloxycarbonyl)-4-(cyclohexylmethyl)-5-(2',2'-difluoro-2'-ethoxycarbonyl-1'-(hydroxy)ethyl)-2,2-(dimethyl)oxazolidine.

To (4S,5R)-3-(tert-butyloxycarbonyl)-4-(cyclohexylmethyl)-2,2-(dimethyl)oxazolidine-5-carboxaldehyde (1.20 g, 3.70 mmol, Rosenberg, S. H., et al, *J. Med. Chem.*, 1990, 33, 1582) in tetrahydrofuran (15 mL) was added bromodifluoroethyl acetate (1.50 g, 7.39 mmol) and zinc (0.60 g, 9.2 mmol). The reaction flask was placed in an ultrasonic cleaning bath for 1 h. The mixture was poured into saturated NaHCO$_3$ solution and extracted into ethyl acetate which was dried over Na$_2$SO$_4$ and evaporated. Chromatography of the residue on silica gel with 10% ethyl acetate in hexane afforded 1.30 g (78%) of the desired product as an oil: Rf 0.26 (20% ethyl acetate/80% hexane); $^1$H NMR (CDCl$_3$) δ4.35 (q, 2H), 4.20–3.97 (m, 3H), 1.54 (s, 3H), 1.50 (s, 3H), 1.48 (s, 9H), 1.37 (t, 3H).

B. (4S,5R,1'R)-3-(tert-Butyloxycarbonyl)-4-(cyclohexylmethyl)-5-[1',3'-dihydroxy-(2',2'difluoro)propyl]-2,2-(dimethyl)oxazolidine.

The resultant compound from Example 42A (1.28 g, 2.85 mmol) in methanol (10 mL) was treated with NaBH4 (0.22 g, 5.82 mmol). After 8 h, NaBH4 (0.11 g, 2.91 mmol) was added and the mixture was stirred for 14 h. After solvent evaporation, the mixture was partitioned between ether and saturated NaHCO3 solution and the organic layer was dried over Na2SO4 and evaporated. Chromatography of the residue on silica gel with 20% ethyl acetate in hexane afforded 0.79 g (68%) of the desired product as a solid: mp 148°–149° C.; Rf 0.45 (50% ethyl acetate/50% hexane); $^1$H NMR (CDCl3) δ4.31–4.23 (m, 1H), 4.07–3.83 (m, 4H), 1.62 (s, 3H), 1.54 (s, 3H), 1.48 (s, 9H).

C. (4S,5R,1'R)-3-(tert-Butyloxycarbonyl)-4-(cyclohexylmethyl)-5-[2',2'-difluoro-1'-hydroxy-3'-(p-toluenesulfonyloxy)propyl]-2,2-(dimethyl)oxazolidine.

The resultant compound from Example 42B (0.374 g, 0.918 mmol) in pyridine (5 mL) at 0° C. was treated with p-toluenesulfonyl chloride (0.195 g, 1.02 mmol). After 260 h at 0° C. the mixture was evaporated, dissolved in ether, washed sequentially with 0.5M H3PO4, saturated NaHCO3 solution and brine, and then was dried over Na2SO4 and evaporated to afford 0.510 g (99%) of a foam: Rf 0.70 (50% ethyl acetate/50% hexane); $^1$H NMR (CDCl3) δ4.56–4.42 (m, 1H), 4.32–4.12 (m, 2H), 4.05–3.80 (m, 2H), 2.47 (s, 3H), 1.53 (s, 3H), 1.50 (s, 3H), 1.48 (s, 9H).

D. (4S,5R,1'R)-3-(tert-Butyloxycarbonyl)-4-(cyclohexylmethyl)-5-[3'-azido-2',2'-difluoro-1'-(hydroxy)-propyl]-2,2-(dimethyl)oxazolidine.

The resultant compound from Example 42C (0.300 g, 0.534 mmol) and LiN3 (0.130 g, 2.66 mmol) in dimethylformamide (2 mL) were heated at 90° C. for 48 h. The mixture was diluted with ethyl acetate, washed with water and brine, and then was dried over Na2SO4 and evaporated. Chromatography of the residue on silica gel with 8–12% ethyl acetate in hexane afforded 0.165 g (72%) of the desired product as an oil: Rf 0.35 (20% ethyl acetate/80% hexane); $^1$H NMR (CDCl3) δ4.27–4.18 (m, 1H), 4.00–3.60 (m, 4H), 1.60 (s, 3H), 1.52 (s, 3H), 1.48 (s, 9H).

E. (4S,5R,1'R)-3-(tert-Butyloxycarbonyl)-4-(cyclohexylmethyl)-5-[2',2'-difluoro-3'-dimethylamino-1'-(hydroxy)propyl]-2,2-(dimethyl)oxazolidine.

The resultant compound from Example 42D (0.165 g, 0.381 mmol), 35% aqueous formaldehyde (0.3 mL) and 10% Pd/C (0.15 g) in methanol (5 mL) were stirred under a hydrogen atmosphere for 16 h. The reaction was filtered and evaporated to afford 0.157 g (95%) of the desired product as a solid: mp 120°–121° C.; Rf 0.39 (50% ethyl acetate/50% hexane); $^1$H NMR (CDCl3) δ4.28–4.15 (br, 1H), 4.02 (d, 1H), 3.96–3.83 (m, 1H), 3.08–2.76 (m, 2H), 2.39 (s, 6H), 1.59 (s, 3H), 1.53 (s, 3H), 1.49 (s, 9H). Anal. Calcd for C22H40N2O4F2: C, 60.81; H, 9.28; N, 6.45. Found: C, 60.70; H, 9.22; N, 6.25.

F. The resultant compound from Example 42E (0.028 g, 0.064 mmol) was stirred for 1 h in 4M HCl/ethanol and evaporated with ether chasers. To this residue was added the resultant acid from Example 1 (0.027 g, 0.066 mmol), 1-hydroxybenzotriazole (0.028 g, 0.207 mmol), dimethylformamide (0.5 mL) and N-methylmorpholine (0.021 mL, 0.191 mmol). The mixture was cooled to −23° C. and treated with 1-ethyl-3-(dimethylaminopropyl)carbodiimide hydrochloride (0.018 g, 0.094 mmol). After 2 h at −23° C. and 14 h at ambient temperature the mixture was poured into saturated NaHCO3 solution and extracted into ethyl acetate. The organic phase was washed with water and brine, and then was dried over Na2SO4 and evaporated. Chromatography of the residue on silica gel with ethyl acetate afforded 0.0134 g (30%) of the desired product as a glass: Rf 0.15 (ethyl acetate). Anal. Calcd for C36H59N3O7F2: C, 63.23; H, 8.70; N, 6.14. Found: C, 63.13; H, 8.69; N, 5.92.

EXAMPLE 43

N-(6-Cyclohexyl-2,2-difluoro-1-dimethylamino-3R-hydroxy-4-oxohexan-5(S)-yl) 2(S)-(1(S)-4-methoxymethoxy)piperidin-1-yl-carbonyl)-phenylethoxy)hexanamide A. (4S,5R,)-3-(tert-Butyloxycarbonyl)-4-(cyclohexylmethyl)-5-(2',2'-difluoro-3'-dimethylamino-1'-oxopropyl)-2,2-(dimethyl)oxazolidine.

To oxalyl chloride (0.030 mL, 0.35 mmol) in CH2Cl2 (1 mL) at −60° C. was added dimethylsulfoxide (0.040 mL, 0.56 mmol) in CH2Cl2 (1 mL). After 15 min, The resultant compound from Example 64 (0.0509 g, 0.117 mmol) in CH2Cl2 (3 mL) was added and the mixture was stirred for 30 min at which point triethylamine (0.125 mL, 0.892 mmol) was added. After 30 min, the reaction was quenched with saturated NaHCO3 solution (2 mL), diluted with ether, washed with saturated NaHCO3 solution and brine, and then was dried over MgSO4 and evaporated to afford 0.046 g, (91%) of the desired product as an oil: Rf 0.58 (50% ethyl acetate/50% hexane); $^1$H NMR (CDCl3) δ4.73 (d, 1H), 2.32 (s, 6H), 1.48 (s, 9H).

B. Using the procedure of Example 42F with the resultant compound from Example 43A gave the desired product as a glass: Rf 0.29 (ethyl acetate). HRMS: calcd for ((M+H)+) of C36H58N3O7F2: 682.4243. Found: 682.4218.

EXAMPLE 44

N-(5-cyclohexyl-2,2-difluoro-1-dimethylamino-3(R)-hydroxypentan-4(S)-yl) 2(S)-(1(S)-(4-(methoxymethoxy)piperidin-1-yl-carbonyl)phenylethoxy)hexanamide A. (5R,4S)-4-Cyclohexylmethyl-5-[1',1'-difluoro-2'-(dimethylamino)ethyl]-2-oxazolidinone.

(5R,4S)-4-Cyclohexylmethyl-5-[2'-azido-(1',1'-difluoro)ethyl]-2oxazolidinone (Rosenberg, S. H., et al, U.S. Pat. No. 4,857,507) was converted in 73% yield to the desired product using the procedure of Example 42E: Rf 0.26 (50% ethyl acetate/50% hexane); $^1$H NMR (CDCl3) δ2.94 (ddd, 1H), 2.71 (ddd, 1H), 2.36 (s, 6H).

B. (3R,4S)-4-Amino-5-cyclohexyl-2,2-difluoro-1-dimethylamino-3-(hydroxy)pentane.

The resultant compound from Example 44A (0.243 g, 0.840 mmol) and barium hydroxide octahydrate (0.530 g, 1.68 mmol) in dioxane (9 mL), and water (6 mL) were heated at reflux for 17 h. The mixture was filtered, diluted with water and extracted into ether which was dried over Na2SO4 and evaporated to afford 0.185 g (83%) of the desired product as a solid: mp 47°–49° C.; $^1$H NMR (CDCl3) δ3.57 (dd, 1H), 3.34 (dd, 1H), 2.98 (ddd, 1H), 2.72 (ddd, 1H), 2.37 (s, 6H). Anal. Calcd for C13H26N2OF2: C, 59.06; H, 9.91; N, 10.60. Found: C, 59.41; H, 9.90; N, 10.43.

C. Using the procedure of Example 42F with the resultant compound from Example 44B gave the desired product as a glass: Rf 0.34 (5% methanol/95% chloroform). Anal. Calcd for $C_{37}H_{57}N_3O_6F_2$: C, 64.29; H, 8.79; N, 6.43. Found: C, 64.41; H, 8.42; N, 6.43.

EXAMPLE 45

N-(5-cyclohexyl-2,2-difluoro-1-dimethylamino-3-oxopentan-4(S)-yl) 2(S)-(1(S)-(4-(methoxymethoxy)piperidin-1-yl-carbonyl)phenylethoxy)hexanamide Using the procedure of Example 43A with the resultant compound from Example 44C gave the desired product as a glass: $R_f$ 0.49 (5% methanol/95% chloroform); MS m/e 652 ((M+H)+).

EXAMPLE 46

N-(Bis(dimethylamino)methylene) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide A. (4S,5S,2'S)-3-(tert-Butyloxycarbonyl)-4-(cyclohexylmethyl)-5-[3'-methyl-2'-[(tetramethylguanidinyl)carbonyl]butane.

To 2(S)-((3-(tert-Butyloxycarbonyl-2,2-dimethyl-4(S)-cyclohexylmethyl-5(S)-oxazolidinyl) methyl)-3-methylbutanoic acid (Fung, et al. PCT Patent WO 9003971)(50.0 mg, 0.121 mmol) and 1-hydroxybenzotriazole (25.0 mg, 0.185 mmol) in dimethylformamide (2 mL) at 0° C. was added N-methylmorpholine (0.013 mL, 0.12 mmol) and N-ethyl-N'-(dimethylamino)-propylcarbodiimide hydrochloride (33.0 mg, 0.170 mmol). The mixture was stirred at 0°–10° C. for 24 h, cooled to −23° C. and treated with 1,1,3,3-tetramethylguanidine (0.060 mL, 0.478 mmol). After 2 h at −23° C. and 40 h at ambient temperature the mixture was poured into saturated NaHCO₃ solution and extracted into ethyl acetate. The organic phase was washed with water and brine, and then was dried over $Na_2SO_4$ and evaporated to afford 64.4 mg (100%) of an oil: Rf 0.22 (10% methanol/90% chloroform); ¹H NMR (CDCl₃) δ2.90 (s, 12H), 1.48 (s, 9H), 1.01 (d, 3H), 0.95 (d, 3H).

B. The resultant compound from Example 46A was deprotected and coupled according to the procedure of Example 2C to give the desired product as a glass: $R_f$ 0.12 (10% methanol/90% chloroform); ¹H NMR (CDCl₃) δ6.14, 6.05 (2d, total 1H), 3.34 (s, 3H), 2.91 (s, 12H).

EXAMPLE 47

2(S)-(1(S)-(4-(Methoxymethoxy)piperidin-1-yl-carbonyl)-phenylethoxy)hexanoic Acid Amide of (2S,4S,1'R,2'S)-2-(2-Amino-3-cyclohexyl-1-hydroxypropyl)-4-(benzylsulfonylmethyl)tetrahydrofuran A. (3S,5S,4'S,5'R)-5-[3'-(tert-Butyloxycarbonyl)-4'-(cyclohexylmethyl)-2',2'-(dimethyl)oxazolidin-5'-yl]-3-(benzylthiomethyl)dihydrofuran-2-(3H)-one.

To (5S,4'S,5'R)-5-[3'-(tert-Butyloxycarbonyl)-4'-(cyclohexylmethyl)-2',2'-(dimethyl)oxazolidin-5'-yl)-3(methylene)dihydrofuran-2(4H)-one (905 mg, 2.30 mmol, Rosenberg, S. H., et al., *J. Med. Chem.* 1990, 33, 1582) in dimethylformamide (10 mL) was added triethylamine (0.42 mL, 3.0 mmol) and benzyl mercaptan (0.31 mL, 2.6 mmol). The mixture was heated at 50° C. for 48 h, cooled, and diluted with ether, which was washed with water and brine, and then was dried over MgSO₄ and evaporated. Chromatography of the residue on silica gel with 10% ethyl acetate in hexane afforded 315 mg (26%) of the 5R-isomer: mp 144°–146° C.; $R_f$ 0.36 (20% ethyl acetate/80% hexane). Anal. Calcd for $C_{29}H_{43}NO_5S$: C, 67.28; H, 8.37; N, 2.71. Found: C, 66.89; H, 8.36; N, 2.62. The 5S-isomer (483 mg, 41%) was also isolated: mp 114°–115° C.; $R_f$ 0.26 (20% ethyl acetate/80% hexane). Anal. Calcd for $C_{29}H_{43}NO_5S$: C, 67.28; H, 8.37; N, 2.71. Found: C, 67.36; H, 8.45; N, 2.64.

B. (4S,5R,1'S,3'S)-3-(tert-Butyloxycarbonyl)-4-(cyclohexylmethyl)-5-[1',4'-dihydroxy-3'-(benzylthiomethyl)butyl]-2,2-(dimethyl)oxazolidine.

The resultant 5S-isomer from Example 47A (399.6 mg, 0.772 mmol) in ethanol (2 mL) was treated with CaCl₂ (156 mg, 1.55 mmol). After a homogeneous solution was obtained, tetrahydrofuran (1.2 mL) was added followed by NaBH₄ (117 mg, 3.09 mmol). After 20 h at ambient temperature the mixture was diluted with ether, washed with 0.5M H₃PO₄, saturated aqueous NaHCO₃ solution, and brine, and then was dried over MgSO₄ and evaporated. Chromatography of the residue on silica gel with 25% ethyl acetate in hexane afforded 379.1 mg (94%) of the desired product as a solid: mp 99°–101° C.; $R_f$ 0.47 (50% ethyl acetate/50% hexane). Anal. Calcd for $C_{29}H_{47}NO_5S$: C, 66.76; H, 9.08; N, 2.68. Found: C, 66.76; H, 9.03; N, 2.76.

C. (4S,5R,2'S,4'S)-3-(tert-Butyloxycarbonyl)-4-cyclohexylmethyl)-2,2-dimethyl-5-[4'-(benzylthiomethyl)tetrahydrofuran-2'-yl]oxazolidine.

The resultant compound from Example 47B (341.1 mg, 0.654 mmol) and triphenylphosphine (393 mg, 1.50 mmol) in tetrahydrofuran (6 mL) at −10° C. were treated with diethyl azodicarboxylate (0.20 mL, 1.3 mmol). After 90 min at −10° C. and 18 h at ambient temperature the solvent was evaporated and the residue was chromatographed on silica gel with 4% ethyl acetate in hexane to afford 274 mg (83%) of a white solid: mp 67°–69° C.; $R_f$ 0.52 (20% ethyl acetate/80% hexane). Anal. Calcd for $C_{29}H_{45}NO_4S$: C, 69.15; H, 9.00; N, 2.78. Found: C, 69.03; H, 8.95; N, 2.73.

D. (4S,5R,2'S,4'S)-3-(tert-Butyloxycarbonyl)-4-(cyclohexylmethyl)-2,2-dimethyl-5-[4'-benzylsulfonylmethyl)tetrahydrofuran-2'-yl]oxazolidine The resultant compound from Example 47C (145.0 mg, 0.288 mmol) in CH₂Cl₂ (8 mL) was treated with meta-chloroperbenzoic acid (300 mg, 0.9 mmol, 50% pure). After 30 min at ambient temperature, the mixture was evaporated and dissolved in ethyl acetate which was washed with 1:1 10% aqueous Na₂SO₃ solution/saturated aqueous NaHCO₃ solution, saturated aqueous NaHCO₃ solution, and brine, and then was dried over Na₂SO₄ and evaporated to afford 152 mg (99%) of a white solid: mp 178°–179° C.; $R_f$ 0.52 (50% ethyl acetate/50% hexane). Anal. Calcd for $C_{29}H_{45}NO_6S \cdot 0.5\ H_2O$: C, 64.21; H, 8.50; N, 2.64. Found: C, 63.94; H, 8.51; N, 2.57.

E. The resultant compound from Example 47D was deprotected and coupled according to the procedure of Example 2C to give the desired product as a foam: Rf 0.22 (ethyl acetate). Anal. Calcd for $C_{43}H_{64}N_2O_9S \cdot 0.75\ H_2O$: C, 64.68; H, 8.27; N, 3.51. Found: C, 64.47; H, 8.06; N, 3.55.

EXAMPLE 48

5(S)-(2(S)-(1(S)-(4-(Methoxymethoxy)piperidin-1-yl)carbonyl-2-phenyl)ethoxyhexanamido)-6-cyclohexyl-4(S)-hydroxy-2(S)-isopropyl-1-hexanol A. (2S,4S,5S) 5-(Benzyloxycarbonyl)amino-6-cyclohexyl-2-isopropyl-1,4-hexanediol.

A solution of (2S,4S,5S)-5-amino-6-cyclohexyl-4-hydroxy-2-isopropylhexanoic acid lactone (1.0 g, 2.6 mmol, Bradbury et. al, *J. Med. Chem.* 1990, 33, 2335–42), calcium chloride (0.573 g, 5.2 mmol) and sodium borohydride (0.39 g, 10.5 mmol) in 40 mL of THF were stirred at 0°–5° C. for 2 h, then at room temperature for 2 h. The reaction was recooled to 0°–5° C., ether was added, and 1M potassium hydrogen sulfate was added until gas evolution ceased. The separated organic layer was washed sequentially with saturated sodium bicarbonate and sodium chloride, then dried (MgSO$_4$). Evaporation of the solvent gave 0.910 g of a crude white solid which was purified by column chromatography using 1:3 ethyl acetate-hexane, to give 0.754 g (74%) of diol: mp 111°–112° C.; $^1$H NMR (CDCl$_3$) δ7.41–7.27 (m, 5 H, Ph), 5.11 (s, 2H, O—CH$_2$), 4.91 (br d, 1H, J=9 Hz, N H), 3.77–3.56 (br m, 3H, HOCH$_2$ and HOC H), 3.05 (br s, 1 H, OH), 2.25 (br s, 1H, OH), 0.87 (dd, 6H, J=3 and 7 Hz, isopropyl); IR (CDCl$_3$) 3617, 3428, 2957–2835, 1707, 1505, 1442, 1223, and 1038 cm$^{-1}$. Anal. Calcd for C$_{23}$H$_{37}$NO$_4$: C, 70.55; H, 9.52, N; 3.58. Found: C, 70.98; H, 9.63; N, 3.55.

B. (2S,4S,5S)-5-Amino-6-cyclohexyl-2-isopropyl-1,4-hexanediol.

A sample of diol from Example 48A (0.350 g, 0.89 mmol) and 40 mg of 10% Pd/C in 100 mL methanol was hydrogenated at 4 atm. Filtration of the catalyst and evaporation of the solvent gave 230 mg of amino diol which was used without further purification.

C. The procedure of Example 2C, part 2, was adapted: 191 mg (0.4 mmol) of acid from Example 1, amino diol from Example 48B (110 mg, 0.427 mmol), and HOBT (95 mg, 0.7 mmol), in 1.5 mL DMF cooled at −23° C. was added EDCI (90 mg, 0.44 mmol). The reaction mixture was stirred and allowed to warm slowly to room temperature over 18 h. The DMF was evaporated and the residue was purified by flash chromatography (3% methanol/methylene chloride). The desired product was isolated in 40% yield (108 mg): mp 47°–54° C.; $^1$H NMR (CDCl$_3$) δ7.38–7.26 (m, 5 H, Ph), 5.87–5.7 (br dd, two rotomers, 1H, amide N H), 4.65 (s, 2H, OCH$_2$O), 4.59–4.51 (4 line m, 1H, COCHO), 3.35 (s, 3H, CH$_3$O), 0.96–0.83 (6 line m, 6H, isopropyl); IR (CDCl$_3$) 3380, 2940–2840, 1644, 1520, 1444, 1142, 1090, 1038, 870–950, and 795–600 cm$^{-1}$. Anal. Calcd for C$_{37}$H$_{62}$N$_2$O$_7$: C, 68.70; H, 9.66; N; 4.33. Found: C, 67.99; H, 9.53; N, 4.41.

EXAMPLE 49

N-(3-(4-Morpholino)propyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(3-(4-Morpholino)propyl) (2S,4S,5S)-5-(tert-butyloxycarbonyl)amino-4-hydroxy-2-isopropylhaxanamide.

2-Isopropyl-4-[1-(tert-butyloxycarbonylamino)-2-cyclohexyl]ethyl-γ-butyrolactone (4.0018 g, 11.32 mmol, Bradbury, R. H., et al., *Tetrahedron Lett.* 1989, 30, 3845) and 4-(3-aminopropyl)morpholine (16.5 mL, 0.1124 mmol) were warmed at 60° C. for 96 hours. The reaction mixture was partitioned between water (150 mL) and methylene chloride (120 mL). The organic phase was washed with water (3×100 mL) and brine (100 mL), dried over sodium sulfate, and concentrated under reduced pressure to afford a solid which was recrystallized from hot ethyl acetate to afford the title compound (4.719 g, 84%): mp 161°–2° C.; Rf 0.18 (7.5% MeOH—CHCl$_3$); $^1$H NMR (CDCl$_3$) δ0.73–1.04 (br m) and 0.93 (2 overlapping d, 8H total), 1.05–1.50 (br m) and 1.45 (s, 17H total), 1.58–1.77 (br m, 10H), 1.79–2.03 (m, 4H), 2.41–2.52 (m, 6H), 3.25–3.45 (m, 2H), 3.43–3.59 (br m, 2H), 3.68–03.74 (m, 4H), 3.90–4.10 (br m, 1H), 4.65 (br d, 1H), 7.04 (br m, 1H); MS m/e 4 98 ((M+H)+). Anal. Calcd for C$_{27}$H$_{51}$N$_3$O$_5$.H$_2$O: C,; H,; N,. Found: C,; H,; N,.

B. Part 1. To the compound resulting from Example 49a (3.1765 g, 6.38 mmol) suspended in methylene chloride (16 mL) and cooled to 0° C. was added trifluoroacetic acid (16 mL) over 30 minutes. The resulting solution was stirred at 0° C. for 4 hours and then additional TFA (6 mL) was added. After 2 hours, the flask was sealed and allowed to stand in the refrigerator for 12 hours. The mixture was concentrated under reduced pressure and the residue obtained basified with 4M sodium hydroxide solution. The solution was saturated with sodium chloride and extracted with 5% isopropanol in chloroform (4×25 mL). The combined organic extracts were washed with brine (30 mL), dried over sodium sulfate, and concentrated in vacuo to give N-[(4-morpholino)propyl)-5(S)-amino-6-cyclohexyl-4(S)-hydroxy-2-(S)-isopropylhexanamide (2.8851 g, 100%) as a waxy solid: $^1$H NMR (CDCl$_3$) δ0.70–1.00 (br m), 0.92 (d) and 0.95 (d, 8H total), 1.00–1.93 (several br m, approx. 19H), 2.03–2.14 (m, 1H), 2.40–2.51 (m, 6H), 2.52–2.62 (m, 1H), 3.02–3.14 (m, 1H), 3.25–3.45 (m, 2H), 3.65–3.80 (m, 4H), 6.77–6.85 (br m, 1H); MS m/e 398 ((M+H)+). Anal. Calcd for C$_{22}$H$_{43}$N$_3$O$_3$.1.5H$_2$O: C, 62.23; H, 10.92; N, 9.90. Found: C, 62.63; H, 10.57; N, 9.76.

Part 2. To the above amino alcohol (2.7942 g, 6.38 mmol), the compound resulting from Example 74 (2.7217 g, 6.695 mmol), 1-hydroxybenzotriazole hydrate (HOBT) (1.4626 g, 9.55 mmol), and N-methylmorpholine (NMM) (1.05 mL, 0.966 g, 9.55 mmol) dissolved in dimethylformamide (DMF) (24 mL) and cooled to −10° C. was added 1-ethyl-3-(3′-dimethylamino)-propylcarbodiimide (EDC) (1.5910 g, 8.30 mmol) The reaction mixture was stirred at −10° C., allowed to gradually warm to ambient temperature, and stirred at ambient temperature for 3 days. The reaction mixture was concentrated under reduced pressure and then partitioned between methylene chloride (75 mL) and 4:1 saturated sodium bicarbonate/water (2×25 mL). The organic phase was washed with brine (25 mL), dried over sodium sulfate, and concentrated under reduced pressure to afford an amorphous solid (2.0314 g, 2.5325 mmol, 94%). Flash chromatography on silica gel eluting with a gradient (10%,15%) of methanol in methylene chloride afforded the title compound as an amorphous solid (1.74 g, 65%): mp 85°–95° C.; Rf 0.19 (6% MeOH—CH$_2$Cl$_2$); $^1$H NMR (CDCl$_3$) δ0.67–1.00 (br m), 0.89 (t) and 0.94 (d, 11H total), 1.00–2.00 (several br m, 29H), 2.0–2.14 (.m, 1H), 2.20–2.40 br m) and 2.40–2.60 (br m, 6H total), 2.67–2.87 (m, 3H), 2.95–3.07 (br m) and 3.3.16–3.34 (br m, 3H total), 33.36 (2 s) and 3.34–3.95 (several br m, 14H total), 4.65 (2 s, 2H), 6.73–6.91 (br m, 2H), 7.20–7.35 (m, 5H); MS m/e 786 ((M+H)+). Anal. Calcd for C$_{44}$H$_{75}$N$_5$O$_7$.H$_2$O: C,; H,; N,. Found: C,; H,; N,.

EXAMPLE 50

N-(2-Pyridylmethyl) 5(S)-(N-(1(S)-(4-(methoxymethoxy)piperidin-1-yl)carbonyl-2-phenyl-)ethyl-L-norleucinamido)-6-cyclohexyl-4(S)-hydroxy-2(S)-isopropylhexanamide A. N-(2-Pyridylmethyl) (2S,4S,5S)-5-(tert-butyloxycarbonyl)amino-4-hydroxy-2-isopropylhaxanamide.

The procedure of Example 49A was employed, with the substitution of 2-(aminomethyl)pyridine, to provide the title compound: mp 128°-9° C.; $^1$H NMR (CDCl$_3$) δ0.95 (d, 6H), 1.06–1.25 (br m, 6H), 1.45 (s, 9H), 1.63 (m, 7H), 1.75–1.96 (br m, 4H), 2.17 (ddd, 1H), 3.44 (d, 1H), 3.54 (br s, 1H), 4.28 (dd, 1H), 4.72 (d, 1H), 5.02 (dd, 1H), 7.50 (br s, 1H), 7.22 (dd, 1H), 7.28 (d, 1H), 7.69 (ddd, 1H), 8.43 (d, 1H); MS m/e 462 ((M+H)$^+$). Anal. Calcd for C$_{26}$H$_{43}$N$_3$O$_4$: C, 67.65; H, 9.39; N, 9.10. Found: C, 67.60; H, 9.29; N, 9.12.

B. The procedure of Example 49B was employed, with the substitution of the resultant compound from Example 50A for the resultant compound from Example 49A, to provide the title compound: mp °C.; Rf 0.32 (5% MeOH—CH$_2$Cl$_2$); $^1$H NMR (CDCl$_3$) δ; MS m/e (M+NH$_4$)$^+$. Anal. Calcd for C$_n$H$_m$N$_o$O$_p$. H$_2$O: C,; H,; N,. Found: C,; H,; N,.

EXAMPLE 51

N-(3-Pyridylmethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-3-Pyridylmethyl) (2S,4S,5S)-5-tert-butyloxycarbonyl)amino-4-hydroxy-2-isopropylhexanamide.

The procedure of Example 49A was employed, with the substitution of 3-(aminomethyl)pyridine for 4-(3-aminopropyl)morpholine, to provide the title compound as white needles (50% yield): mp 147°-49° C.; [α]$^{25}$$_D$= −36.4° (c 1.12, CHCl$_3$); $^1$H NMR (CDCl$_3$) δ0.91 (d, J=6 Hz, 3H), 0.93 (d, J=6 Hz, 3H), 1.43 (s, 9H), 3.35–3.56 (br m, 2H), 4.37–4.55 (8 line m, 2H), 4.62 (br d, 1H), 6.35–6.45 (br s, 1H), 7.24–7.34 (br s, 1H), 7.69 (br d, 1H), 8.47–8.63 (br d, 2H ); MS m/e 462 ((M+H)$^+$). Anal. Calcd for C$_{26}$H$_{43}$N$_3$O$_4$: C, 67.67; H, 9.32; N, 9.11. Found: C, 67.97; H,9.20; N, 9.15.

B. The procedure of Example 49B was employed, with the substitution of the resultant compound from Example 51A for the resultant compound from Example 49A, to provide the title compound as a pale yellow foam (75% yield): mp 60°-68° C.; Rf 0.45 (10% MeOH—CH$_2$Cl$_2$); $^1$H NMR (CDCl$_3$) δ0.64–2.0 (several br m, approx. 36H), 2.13–2.25 (br m, 1H), 2.63–2.77 (br m, 1H), 2.77–2.90 (br m, 2H), 3.00–3.31 (br m, 2H), 3.34 (s), 3.35 (s) and 3.31–3.81 (several br m, 8H), 3.81–3.94 (br m, 1H), 4.35 (dd, 1H), 4.55–5.70 (m, 3H), 6.20–6.30 (m, 1H), 6.79 (d) and 6.85 (d, 1H total), 7.19–7.37 (br m, approx. 5H), 7.66 (br d, 1H), 8.52 (br d, 2H); MS m/e 750 ((M+H)$^+$).

EXAMPLE 52

N-(4-Pyridylmethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(4-Pyridylmethyl) (2S,4S,5S)-5-(tert-butyloxycarbonyl)amino-4-hydroxy-2-isopropylhaxanamide.

The procedure of Example 49A was employed, with the substitution of 4-(aminomethyl)pyridine for 4-(3-aminopropyl)morpholine, to provide the title compound: mp 145°-6° C.; Rf 0.32 (10% MeOH—CH$_2$Cl$_2$); $^1$H NMR (CDCl$_3$) δ0.95 (d, 6H), 1.14–1.36 (br m, 6H), 1.43 (s, 9H), 1.58–1.82 (m, 10H), 1.94 (m, 1H), 2.18 (br s, 1H), 3.47 (m, 2H), 4.47 (dd, 2H), 4.56 (br s, 1H), 6.19 (br s, 1H), 7.22 (d, 2H), 8.57 (d, 2H); MS m/e 461 ((M+H)$^+$). Anal. Calcd for C$_{26}$H$_{43}$N$_3$O$_4$: C, 67.65; H, 9.39;N, 9.10. Found: C, 67.28; H, 9.30; N, 9.07.

B. The procedure of Example 49B was employed, with the substitution of the resultant compound from Example 52A for the resultant compound from Example 49A, to provide the title compound as an off-white foam (67% yield): mp 71°-6° C.; Rf 0.50 (5% MeOH—CH$_2$Cl$_2$); $^1$H NMR (CDCl$_3$) δ0.65–1.95 (several br m, approx. 35H), 2.17–2.30 (br m, 1H), 2.65-2.91 (br m, 3H), 2.97–3.13 (br m, 1H), 3.14–3.29 (br m, 2H), 3.35 (2 s) and 3.30–3.80 (br m, 9H total), 3.80–3.91 (br m, 1H), 4.28–4.40 (m, 1H), 4.55–4.60 (m, 3H), 6.27–6.40 (m, 1H), 6.82–6.98 (m, 1H), 7.18–7.35 (m, approx. 8H), 8.55 (d, 2H); MS m/e 750 ((M+H)$^+$). Anal. Calcd for C$_{43}$H$_{67}$N$_5$O$_6$: C, 68.86; H, 9.00; N, 9.34. Found: C, 68.79; H, 8.99; N, 9.30.

EXAMPLE 53

N-(2-(4-Morpholino)ethyl) 5(S)-(N-(1(S)-(4(methoxymethoxy)piperidin-1-yl)carbonyl-2-phenyl)ethyl-L-norleucinamido)-6-cyclohexyl-4(S)-hydroxy-2(S)-isopropylhexanamide A. N-(2-(4-Morpholino)ethyl) (2S,4S,5S)-5-(tert-butyloxycarbonyl)amino-4-hydroxy-2-isopropylhaxanamide.

The procedure of Example 49A was employed, with the substitution of 4-(2-aminoethyl)morpholine for 4-(3-aminopropyl)morpholine, to provide the title compound as a white needles from EtOAc-hexane (1:1) (58% yield): mp 151°-2° C.; $^1$H NMR (CDCl$_3$) δ0.68–0.98 (br m, 8H), 1.05–1.35 (m, 7H), 1.43 (s, 9H), 1.54–1.75 (m, 6H), 1.77–1.95 (m, 2H), 1.97–2.08 (br m, 1H), 2.30–2.69 (m, 6H), 3.17–3.30 (m, 1H), 3.40–3.61 (m, 3H), 3.64–3.77 (m, 4H), 4.73 (br d, 1H), 6.04 (br s, 1H); MS m/e 484 ((M+H)$^+$). Anal. Calcd for C$_{26}$H$_{49}$N$_3$O$_5$.0.25H$_2$O: C, 63.97; H, 10.22; N, 8.61. Found: C, 64.07; H, 10.05; N, 8.68.

B. The procedure of Example 49B was employed, with the substitution of the resultant compound from Example 52A for the resultant compound from Example 49A, to provide the title compound as an off-white solid (77% yield): mp 59°-64° C.; Rf 0.38 (5% MeOH—CH$_2$Cl$_2$); $^1$H NMR (CDCl$_3$) δ0.66–1.00 (br m), 0.89 (t) and 0.94 (d, 11H total), 1.00–1.95 (several br m, approx. 26H), 2.05–2.16 (m, 1H), 2.302.51 (m, 6H), 2.52–2.64 (m, 1H), 2.75–2.86 (m, 2H), 2.90–3.01 (m) and 3.16–3.33 (br m, 2H total), 3.35 (s) and 3.37–3.60 (m, 8H total), 3.60–3.93 (br m, 7H), 4.65 (d, 2H), 6.01–6.10 (br m, 1H), 6.84 (d) and 6.94 (d, 1H total), 7.20–7.36 (m, 5H); MS m/e 772 ((M+H)$^+$). Anal. Calcd for C$_{43}$H$_{73}$N$_5$O$_7$.0.5H$_2$O: C, 66.12; H, 9.55; N, 8.97. Found: C, 66.12; H, 9.54; N, 8.97.

EXAMPLE 54

N-(2-Amino-2-methylpropyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(2-Amino-2-methylpropyl) (2S,4S,5S)-5-(tert-butyloxycarbonyl)amino-4-hydroxy-2-isopropylhaxanamide.

The procedure of Example 49A was employed, with the substitution of 1,2-diamino-2-methylpropane for 4-(3-aminopropyl)morpholine, to provide the title compound as white needles (EtOAc-hexane) (71% yield): mp 133°-6° C.; $^1$H NMR (CDCl$_3$) δ0.70–1.03 (br m) and 0.94 (d, 8H total), 1.03–1.50 (br m), 1.12 (s), 1.17 ( s) and 1.44 (s, 21H total), 1.52–2.00 (br m, 9H), 2.0 1–2.12 (m, 1H), 2.96 (br dd, 1H), 3.40 (br dd, 1H), 3.47–3.59 (br m, 2H), 4.66 (br d, 1H), 6.04–6.13 (br m, 1H); MS m/e 442 ((M+H)$^+$). Anal. Calcd for C$_{24}$H$_{47}$N$_3$O$_4$.0.25 H$_2$O: C, 64.61; H, 10.71; N, 9.42. Found: C, 64.64; H, 10.75; N, 9.28.

B. The procedure of Example 49B may be employed, with the substitution of the resultant compound from Example 54A for the resultant compound from Example 49A, to provide the title compound.

EXAMPLE 55

N-(2-Methyl-2-(4-morpholino)propyl) 5(S)-(N-(1(S)-(4-(methoxymethoxy)piperidin-1-yl)carbonyl-2-phenyl-)ethyl-L-norleucinamido)-6-cyclohexyl-4(S)-hydroxy-2(S)-isopropylhexanamide A. N-(2-Methyl-2-(4-morpholino)propyl) (2S,4S,5S)-5-(tert-butyloxycarbonyl)amino-4-hydroxy-2 isopropyl-haxanamide.

The crude was purified by flash chromatography (0.5% MeOH-EtOAc) to afford the desired compound as a white solid: mp 132°-6° C.; Rf 0.26 (5% MeOH—CH$_2$Cl$_2$); $^1$H NMR (CDCl$_3$) δ0.76–1.01 (br m), 0.94 (d) and 0.97 (d, 8H total), 1.04 (2 s, 6H), 1.09–1.50 (br m) and 1.46 (s, 16H total), 1.52–2.00 (br m, approx. 8H), 2.04–2.15 (br m, 1H), 2.49–2.56 (m, 4H), 3.19 (d, 2H), 3.45–3.60 (br m, 2H), 3.67–3.77 (m, 4H), 4.65 (br d, 1H), 6.31 (br t, 1H) ; MS m/e 512 ((M+H)$^+$). Anal. Calcd for C$_{28}$H$_{53}$N$_3$O$_5$: C, 65.72; H, 10.44; N, 8.21. Found: C, 65.67; H, 10.25; N, 8.11.

B. The procedure of Example 49B was employed, with the substitution of the resultant compound from Example 55A for the resultant compound from Example 49A, to provide the title compound as a foam (71% yield): mp 55°-60° C.; Rf 0.13 (4% Me-CH$_2$Cl$_2$); $^1$H NMR (CDCl$_3$) δ0.67–1.00 (br m), 0.89 (t) and 0.94 (d, 11H total), 1.00–1.20 (br m), 1.05 (s) and 1.06 (s, 11H total), 1.22–1.92 (several br m, approx. 20H), 2.13–2.26 (m, 1H), 2.26–2.50 (vbr m, 1H), 2.51 (m, 4H), 2.65–2.86 (br m, 3H), 2.95–3.08 (br m, 1H), 3.08–3.34 (br m, 4H), 3.36 (s) and 3.35–53.60 (br m, 6H total), 3.60–3.92 (br m, 6H), 4.65 (d, 2H), 6.24–6.31 (br m, 1H), 6.79 (d) and 6.88 (d, 1H total), 7.20–7.36 (m, 5H). Anal. Calcd for C$_{45}$H$_{77}$N$_5$O$_7$.H$_2$O: C, 66.06; H, 9.73; N, 8.56. Found: C, 66.03; H, 9.43; N, 8.48.

EXAMPLE 56

N-(2-(2-Pyridyl)ethyl) 5(S)-(N-(1(S)-(4-(methoxymethoxy)piperidin-1-yl)carbonyl-2-phenyl-)ethyl-L-norleucinamido)-6-cyclohexyl-4(S)-hydroxy-2(S)-isopropylhexanamide A. N-(2-(2-Pyridyl)ethyl) (2S,4S,5S)-5-(tert-butyloxycarbonyl)amino-4-hydroxy-2-isopropylhaxanamide.

The procedure of Example 49A was employed, with the substitution of 2-(2-aminoethyl)pyridine for 4-(3-aminopropyl)morpholine, to provide the title compound as needles (58% yield): mp 124°–26° C.; [α]$^{25}_D$= +17.7° (c 1.9, CHCl$_3$); $^1$H NMR (CDCl$_3$) δ0.86 (d, J=6 Hz, 3H), 0.91 (d, J=6 Hz, 3H), 1.44 (s, 9H), 2.95 (t, J=6 Hz, 2H), 3.18–3.31 (br m, 1H), 3.50–3.63 (br m, 2H), 4.00–4.13 (br m, 1H), 4.71 (br d, J=9 Hz, 1H), 6.30–6.38 (br s, 1H), 7.18–7.25 (br d, 2H), 7.69 (t d, J=9, 1 Hz, 1H), 8.45–8.52 (br d, 1H); MS m/e 476 ((M+H)$^+$). Anal. Calcd for C$_{27}$H$_{45}$N$_3$O$_4$: C, 68.21; H, 9.47; N, 8.84. Found: C, 68.33; H, 9.55; N, 8.85.

B. The procedure of Example 49B was employed, with the substitution of the resultant compound from Example 56A for the resultant compound from Example 49A, to provide the title compound as a white foam (79% yield): mp 52°-6° C.; Rf 0.11 (5% MeOH—CH$_2$Cl$_2$); $^1$H NMR (CDCl$_3$) δ0.62–1.00 (br m) and 0.84–0.92 (overlapping t and d, 11H total), 1.00–1.96 (several br m, approx. 27H), 2.04–2.14 (m, 1H), 2.20–2.57 (vbr m, 1H), 2.80–2.90 (m, 3H), 2.98 (t, 2H), 3.07–3.20 (m), 3.33 (s) and 3.27–3.57 (br m, 7H total), 3.57–3.98 (br m, 5H), 4.20–4.55 (vbr m, 1H), 4.62 (2 s, 2H), 6.40 (br t, 1H), 7.00 (d) and 7.07 (d, 1H total), 7.15–7.34 (m, approx. 6H), 7.66 (td, 1H), 8.51 (dd, 1H) and; MS m/e 764 ((M+H)$^+$). Anal. Calcd for C$_{44}$H$_{69}$N$_5$O$_6$.0.5H$_2$O: C, 68.36; H, 9.13; N, 9.05. Found: C, 68.55; H, 8.96; N, 9.04.

EXAMPLE 57

N-3-(4-Oxido-4-morpholino)propyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(3-(4-Oxido-4-morpholino)propyl) (2S,4S,5S)-5-(tert-butyloxycarbonyl)amino-4-hydroxy-2 -isopropyl-haxanamide.

The procedure of Example 36 was employed, with the substitution of the resultant compound from Example 49A for the resultant compound from Example 11, to provide the title compound as a white powder (92% yield): mp 154°–7° C.; $^1$H NMR (CDCl$_3$) δ0.69–1.03 (br m), 0.91 (d) and 0.93 (d, 8H total), 1.03–1.40 (br m, 6H), 1.43 (s, 9H), 1.50–1.75 (br m, 6H), 1.80–1.95 (br m, 3H), 1.97–2.30 (br m, 6H), 3.05–3.38 (br m, 6H), 3.36–3.50 (m, 2H), 3.50–3.71 (br m, 2H), 3.75–3.86 (br d, 2H), 4.30–4.44 (m, 2H), 4.81 (br d, 1H), 7.96–8.05 (br s, 1H); MS m/e 514 ((M+H)$^+$), 498 (M−16+H)$^+$. Anal. Calcd for C$_{27}$H$_{51}$N$_3$O$_6$.H$_2$O: C, 60.99; H, 10.05; N, 7.90. Found: C, 61.05; H, 9.98; N, 7.93.

B. The procedure of Example 49B was employed, with the substitution of the resultant compound from Example 57A for the resultant compound from Example 49A, to provide the title compound as a tan foam (65% yield): mp 85°–95° C.; Rf 0.15 (10% MeOH—CH$_2$Cl$_2$); $^1$H NMR (CDCl$_3$) δ068–1.00 (m, 11H), 1.00–1.41 (br m, 12H), 1.41–2.20 (br m, approx. 18H), 2.20–2.40 (br m, 2H), 2.70–2.88 (m, 3H), 2.94–3.06 (br m, 2H), 3.06–3.27 (br m, 2H), 3.27–3.55 (br m), 3.35 (s) and 3.36 (s, 9H total), 3.35–4.16 (several br m, 7H), 4.24–4.40 (m, 2H), 4.65 (2 s, 2H), 6.87–6.96 (dd, 1H), 7.25–7.39 (m, 5H), 8.10–8.19 (br m, 1H) and; MS m/e (M+NH$_4$)$^+$. Anal. Calcd for C$_{44}$H$_{75}$N$_5$O$_8$.3H$_2$O: C, 61.73; H, 9.54; N, 8.18. Found: C, 61.74; H, 9.15; N, 8.05.

EXAMPLE 58

N-(3-(2-Hydroxyethyl)amino)propyl) 5(S)-(N-(1(S)-(4-methoxymethoxy)piperidin-1-yl)carbonyl-2-phenyl)ethyl-L-norleucinamido)-6-cyclohexyl-4(S)-hydroxy-2(S)-isopropylhexanamide The procedure of Example 5B can be employed, with the substitution of the resultant compound from Example 74 for the resultant compound from Example 1, to provide the title compound.

EXAMPLE 59

N-(3-Benzyloxycarbonylamino)propyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide The procedure of Example 2C may be employed, with the substitution of the resultant compound from Example 74 for the resultant compound from Example 1, to provide the title compound.

EXAMPLE 60

N-(3-Aminopropyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide The procedure of Example 3 can be employed, with the substitution of the resultant compound from Example 59 for the resultant compound from Example 2, to provide the title compound.

EXAMPLE 61

N-(3-(4-Ethyl-4-morpholinium)propyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide iodide The resultant product from Example 49 (49.9 mg, 63.5 mol) was dissolved in 0 4 mL THF, cooled to 0° C. and iodoethane (5.2 mL, 10.1 mg, 65.0 mmol) was added. The solution was stirred at 0° C. for 6 h, then at room temperature for an additional 12 h.

EXAMPLE 62

N-(3-(1-Imidazolyl)propyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(3-(1-Imidazolyl)propyl) (2S,4S,5S)-5-(tert-butyloxycarbonyl)amino-4-hydroxy-2-isopropylhexanamide.

The procedure of Example 49A was employed, with the substitution of 1-(3-aminopropyl)imidazole for 4-(3-aminopropyl)morpholine, to provide the title compound as white needles (27% yield): mp 148°–150 C; IR 1620–1740 cm$^{-1}$; $^1$H NMR (CDCl$_3$) δ7.56 (s, 1H), 7.07 (s, 1H), 6.96 (s, 1H), 5.87 (br d, 1H), 4.64 (br d, J=9 Hz, 1H), 4.02 (t, J=6 Hz, 2H), 3.57–3.38 (br m, 2H), 3.27 (AB, J=6, 12 Hz, 2H), 2.08–1.57 (several br m, 14H), 1.45 (s, 9H), 1.40–1.10 (several br m, 5H), 0.93 (d, J=6 Hz), 0.91 (d, J=6 Hz,) and 0.82–1.10 (br m, 8H total); MS m/e 479 ((M+H)$^+$). Anal. Calcd for C$_{26}$H$_{46}$N$_4$O$_4$: C, 65.24; H, 9.69; N, 11.70. Found: C, 65.24; H, 9.75; N, 11.75.

B. The procedure of Example 49B was employed, with the substitution of the resultant compound from Example 62A for the resultant compound from Example 49A, to provide the title compound as a white foam (65% yield): mp 59°–65° C.; Rf 0.34 (10% MeOH-1% conc. aq. NH$_4$OH—CH$_2$Cl$_2$); $^1$H NMR (CDCl$_3$) δ0.67–1.00 (m, 11H), 1.00–2.10 (several br m, approx. 29H), 2.10–2.60 (vbr m, 2H), 2.65–2.76 (m, 1H), 2.76–2.86 (m, 2H), 3.00–3.82 (several br m) and 3.36 (2 s, 10H total), 3.82–3.95 (br m, 1H), 3.95–4.10 (m, 2H), 4.67 (d, 2H), 5.83–5.90 (m, 1H), 6.84 (d) and 6.90 (d, 1H total), 6.97 (s, 1H), 7.07 (s, 1H), 7.20–7.34 (m, 5H), 7.59 (d, 1H) ; MS m/e 767 (M+NH$_4$)$^+$. Anal. Calcd for C$_{43}$H$_{70}$N$_6$O$_6$.0.5H$_2$O: C, 66.55; H, 9.22; N, 10.83. Found: C, 66.37; H, 9.11; N, 10.62.

EXAMPLE 63

N-(2-(S-Methyl-N'-cyanoisothioureido)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(2-Aminoethyl) (2S,4S,5S)-5-(tert-butyloxycarbonyl)amino-4-hydroxy-2-isopropylhexanamide.

The procedure of Example 49A was employed, with the substitution of ethylene diamine for 4-(3-aminopropyl)morpholine, to provide the title compound as a white foam (98% yield): mp 55°–62° C.; Rf 0.21 (10% MeOH-1% conc NH$_4$OH—CH$_2$Cl$_2$); $^1$H NMR (CDCl$_3$) δ0.69–1.06 (br m) and 0.93 (d, 8H total), 1.06–1.33 (br m, 5H), 1.33–1.50 (br m) and 1.45 (s, 10H total), 1.50–1.98 (br m, 10H), 1.99–2.09 (m, 1H), 2.74–2.89 (m, 1H) 2.90–3.03 (br m, 1H), 3.03–3.19 (br m, 1H), 3.40–3.75 (br m, 3H), 4.68 (br d, 1H), 6.00–6.09 (br m) and 6.21–6.33 (br m, 1H total); MS m/e 414 ((M+H)$^+$).

B. N-(2-(S-Methyl-N'-cyanoisothioureido)ethyl) (2S,4S,5S)-5-(tert-butyloxycarbonyl)amino-4-hydroxy-2-isopropylhexanamide.

The procedure of Example 24 was employed, with the substitution of the resultant compound from Example 63A for the resultant compound from Example 16 to provide the title compound (100% yield): mp 96°–102° C.; Rf 0.34 (5% MeOH—CH$_2$Cl$_2$); $^1$H NMR (CDCl$_3$) δ0.70–1.06 (br m), 0.91 (d) and 0.94 (d, 8H total), 1.06–1.50 (br m) and 1.44 (s, 15H total), 1.55–1.93 (br m, 10H), 2.11–2.22 (m, 1H), 2.55 (br s) and 2.64 (br s, 3H total), 3.33–3.75 (br m, 6H), 4.58–4.85 (br m, 1H), 6.80–6.95 (br m, 1H), 7.82–8.01 (br m, 1H); MS m/e 529 (M+NH$_4$)$^+$, 512 (M+NH$_4$)$^+$. Anal. Calcd for C$_{25}$H$_{45}$N$_5$O$_4$S: C, 58.68; H, 8.86; N, 13.68. Found: C, 58.33; H, 8.98; N, 12.95.

C. The procedure of Example 49B may be employed, with the substitution of the resultant compound from Example 63B for the resultant compound from Example 49A, to provide the title compound.

EXAMPLE 64

N-(2-(N'-Cyanoureido)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide The procedure of Example 25 may be employed, with the substitution of the resultant compound from Example 63 for the resultant compound from Example 24, to provide the title compound.

EXAMPLE 65

N-(2-((3-Amino-1H-1,2,4-triazol-5-yl)amino)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide The procedure of Example 25 can be employed, with the substitution of the resultant compound from Example 63 and hydrazine hydrate for the resultant compound from Example 24 and 30% aq. NH$_4$OH, to provide the title compound.

EXAMPLE 66

N-(2-((5-Amino-1,2,4-oxadiazol-5-yl)amino)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide The procedure of Example 25 can be employed, with the substitution of the resultant compound from Example 63, hydroxylamine hydrochloride and a molar equivalent quantity of triethylamine for the resultant compound from Example 24 and 30% aq. NH4OH, to provide the title compound.

EXAMPLE 67

N-(2-(Methylsulfamoylamino)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(2-(Methylsulfamoylamino)ethyl) (2S,4S,5S)-5-(tert-butyloxycarbonyl)amino-4-hydroxy-2-isopropylhexanamide.

A solution of the resultant compound from Example 63A (500 mg, 1.21 mmol) and triethylamine (0 50 mL, 3 62 mmol) in 3 mL $CH_2Cl_2$ was cooled to 0° C. and a solution of methyl sulfamoyl chloride (173 mg, 1.33 mmol) in 1.5 mL $CH_2Cl_2$ was added dropwise. The resulting solution was stirred 6 h at 0° C. and a further 48 h at ambient temperature. The mixture was partitioned between 25 mL $CH_2Cl_2$ and 25 mL sat. aq. NaHCO3. The aqueous phase was extracted (3×25 mL $CH_2Cl_2$), then the combined organic phases were dried ($Na_2SO_4$), filtered and concentrated to a white solid (582 mg). Flash chromatography (silica gel, 3.5% MeOH—$CH_2Cl_2$) afforded 327 mg (0.645 mmol, 53 %) of the title compound as a white foam: mp 75°–95° C.; Rf 0.22 (5% MeOH—$CH_2Cl_2$); $^1$H NMR (CDCl3) δ0.77–1.06 (br m), 0.92 (d) and 0.95 (d, 8H total), 1.05–1.40 (br m, 6H), 1.45 (s, 9H), 1.56–2.03 (br m, 9H), 2.04–2.18 (m, 1H), 2.73 (d, 3H), 3.10–3.30 (br m, 3H), 3.45–3.58 (br m, 2H), 3.7–3.84 (br m, 1H), 4.6–4.82 (br m, 1H), 4..82–4.95 (br m, 1H), 5.32–5.51 (br m, 1H), 6.35–6.45 (br m) and 6.61–6.75 (br m, 1H total); MS m/e 524 $(M+NH_4)^+$, 507 $(M+NH_4)^+$. Anal. Calcd for $C_{23}H_{46}N_4O_6S$: C, 54.52; H, 9.15; N, 11.06. Found: C, 54.41; H, 9.38; N, 10.59.

B. The procedure of Example 49B can be employed, with the substitution of the resultant compound from Example 67A for the resultant compound from Example 49A, to provide the title compound.

EXAMPLE 68

N-(2-(1,1-Dioxo-4-thiomorpholino)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(2-(1,1-Dioxo-4-thiomorpholino)ethyl) 2(S)-((3(tert-butyloxycarbonyl)-2,2-dimethyl-4(S)-cyclohexylmethyl-5(S)-oxazolidinyl) methyl)-3-methylbutanamide.

The procedure of Example 2B was employed, with the substitution of 4-(2-aminoethyl) thiomorpholine-1,1-dioxide for 4-(3-aminopropyl)morpholine, to provide the title compound as a white foam (100%): $^1$H NMR (CDCl3) δ0.83–1.04 (m, 8H), 1.04–1.44 (br m, 6H), 1.48 (s, 9H), 1.53–1.95 (several br m, 18H), 2.03–2.14 (br m, 1H), 2.66 (t, 2H), 2.98–3.15 (br m, 8H), 3.20–3.53 (br m, 2H), 3.56–3.85 (br m, 2H), 5.83–5.94 (br m, 1H); MS m/e 572 $((M+H)^+)$.

B. The procedure of Example 2C can be employed, with the substitution of the resultant compound from Example 68A for the resultant compound from Example 2B, to provide the title compound.

EXAMPLE 69

N-Ureido 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-Amino (2S,4S,5S)-5-(tert-butyloxycarbonyl)amino-4-hydroxy-2-isopropylhexanamide.

The procedure of Example 49A was employed, with the substitution of hydrazine hydrate for 4-(3-aminopropyl)morpholine, to provide the title compound as a white foam (73% yield): mp 55°–62° C.; Rf 0.45 (5% MeOH—$CH_2Cl_2$); $^1$H NMR (CDCl3) δ0.55–1.94 (several br m, 16H approximately), 0.94 (dd, 6H), 1.49 (s, 9H), 1.58 (s, 3H), 1.64 (s, 3H), 2.05 (m, 1H), 2.50–3.50 (vbr m, 2H), 3.69 (m, 2H), 6.92 (m, 1H); MS m/e 426 $((M+H)^+)$ 443 $((M+NH_4)^+)$ Anal Calcd for $C_{23}H_{43}N_3O_4$: C, 64.91; H, 10.18; N, 9.87. Found: C, 65.00; H, 10.04; N, 9.64.

B. N-Amino (2S,4S,5S)-5-(tert-butyloxycarbonyl)amino-4-hydroxy-2-isopropylhexanamide.

The procedure of Example 6B was employed, with the substitution of the resultant compound from Example 69A for the resultant compound from Example 6A, to provide the title compound as a white powder (100% yield): mp 95°–102° C.; Rf 0.22 (5% MeOH—$CH_2Cl_2$); $^1$H NMR (CDCl3) δ0.85–2.03 (several br m, 16H approximately), 0.97 (dd, 6H), 1.49 (s, 9H), 1.59 (s. 3H), 1.65 (s, 3H), 2.11 (m, 1H), 3.69 (m, 1H), 3.89 (m, 1H), 5.31 (m, 2H), 7.07 (m, 1H), 7.49 (br s, 1H); MS m/e 469 $((M+H)^+)$, 486 $((M+NH_4)^+)$. Anal. Calcd for $C_{24}H_{44}N_4O_5$: C, 61.51; H, 9.46; N, 11.96. Found: C, 61.32; H, 9.43; N, 11.33.

C. The procedure of Example 49B was employed, with the substitution of the resultant compound from Example 69B for the resultant compound from Example 49A, to provide the title compound as a white powder (34% yield): mp 115°–121° C.; Rf 0.33 (10% MeOH—$CH_2Cl_2$); $^1$H NMR (CDCl3) δ0.74–2.00 (several br m, approx. 17H), 0.96 (d, 6H), 1.50 (s, 9H), 2.58 (m, 1H), 2.90 (m, 1H), 3.36 (m, 1H), 3.70 (m, 1H), 6.00–7.70 (vbr m, approx. 2H), 6.78 (m, 1H), 11.33 (m, 1H); MS m/e 429 $((M+H)^+)$, 446 $((M+NH_4)^+)$. Anal. Calcd for $C_{21}H_{40}N_4O_5 \cdot 0.25 H_2O$: C, 58.24; H, 9.42; N, 12.93. Found: C, 58.17; H, 9.22; N, 12.93

EXAMPLE 70

N-(Methylsulfamoylamino) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(Methylsulfamoylamino) (2S,4S,5S)-5-(tert-butyloxycarbonyl)amino-4-hydroxy-2-isopropylhexanamide.

The procedure of Example 67A can be employed, with the substitution of the resultant compound from Example 69A for the resultant compound from Example 63A, to provide the title compound.

B. The procedure of Example 49B can be employed, with the substitution of the resultant compound from Example 70A for the resultant compound from Example 49A, to provide the title compound.

EXAMPLE 71

N-(Methylsulfonylamino) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(Methylsulfonylamino) (2S,4S,5S)-5-(tert-butyloxycarbonyl)amino-4-hydroxy-2-isopropylhexanamide.

The procedure of Example 67A can be employed, with the substitution of methanesulfonyl chloride for methylsulfamoyl chloride, to provide the title compound.

B. The procedure of Example 49B can be employed, with the substitution of the resultant compound from Example 71A for the resultant compound from Example 49A, to provide the title compound.

EXAMPLE 72

N-(Carboxyethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(Ethyl carboxyethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide.

The procedure of Example 37B can be employed, with the substitution of the resultant compound from Example 74 for the resultant compound from Example 1, to provide the title compound.

B. The procedure of Example 37C can be employed, with the substitution of the resultant compound from Example 72A for the resultant compound from Example 37B, to provide the title compound.

EXAMPLE 73

N-(2-(1-Piperidinyl)ethyl) 5(S)-(N-(1(S)-(4-(methoxymethoxy)piperidin-1-yl)carbonyl-2-phenyl)ethyl-L-norleucinamido)-6-cyclohexyl-4(S)-hydroxy-2(S)-isopropylhexanamide A. N-(2-(1-Piperidinyl)ethyl) (2S,4S,5S)-5-(tert-butyloxycarbonyl)amino-4-hydroxy-2-isopropylhexanamide.

The procedure of Example 49A can be employed, with the substitution of 1-(2-aminoethyl)piperidine for 4-(3-aminopropyl)morpholine, to provide the title compound as a white crystalline solid (90% yield): mp 149°–50° C.; $[\alpha]^{25}_D +1.5°$ (c 2.4, CHCl$_3$).

B. The procedure of Example 49B can be employed, with the substitution of the resultant compound from Example 74A for the resultant compound from Example 49A, to provide the title compound.

EXAMPLE 74

N-(1(S)-(4-(Methoxymethoxy)piperidin-1-yl)carbonyl-2-phenyl)ethyl-L-norleucine

A. 1(S)-(4-(Methoxymethoxy)-piperidine-1-yl)carbonyl)-2-phenylethylamine.

Part 1. 4-(Methoxymethoxy)-piperidine (50.0 g, 0.344 mol), (L)-N-(carbobenzyloxy)phenylalanine (113 g, 0.379 mol), and 1-hydroxybenzotriazole hydrate (106 g, 0.690 mol) were dissolved in 300 mL DMF and cooled to −20° C. under dry nitrogen. A solution of 1-(3-dimethylaminopropyl)-3-ethylcarbodiimide hydrochloride (86 g, 0.448 mol) in 300 mL DMF was added. After warming to room temperature overnight, the DMF was removed under reduced pressure at 35° C. The crude product was partitioned between EtOAc and 10% citric acid. The organic phase was washed sequentially with 10% citric acid, 5% NaHCO$_3$, and brine, dried (MgSO$_4$), and evaporated to give 132 g (90%) of the desired amide: $^1$H NMR (CDCl$_3$) δ1.01 (m, 1H), 1.18 (m, 1H), 1.42 (m, 1H), 1.65 (m, 1H), 2.99 (m, 2H), 3.13 (m, 1H), 3.31 (m, 2H), 3.33 (s, 3H), 3.64 (m, 1H), 3.81 (m, 1H), 4.62 (s, 2H), 4.91 (m, 1H), 5.09 (s, 2H), 5.71 (t, J=9 Hz, 1H), 7.29 (m, 10H); MS m/e 427 ((M+H)$^+$).

Part 2. The above benzyl carbamate (122 g, 0.286 mol) was hydrogenated under 4 atm. H$_2$ in 2 L MeOH using 24.5 g 20% Pd/C. After 16 h, an additional portion of catalyst (25 g) was added. The mixture was shaken for a total of 48 h, then filtered and evaporated in vacuo to provide 75.4 g (90%) of the title compound as a waxy solid: $^1$H NMR (CDCl$_3$) δ1.08 (m, 1H), 1.27 (m, 1H), 1.45 (m, 1H), 1.70 (m, 1H), 3.07 (dd, 2H), 3.2 (m, 2H), 3.35 (m, 2H), 3.35(s, 3H), 4.67 (s, 2H), 7.29 (m, 5H); MS m/e 293 ((M+H)$^+$).

B. Ethyl N-(1(S)-(4-(Methoxymethoxy)piperidin-1-yl)carbonyl-2-phenyl)ethyl-L-norleucinate.

The resultant compound from Example 74A (75.0 g, 0.257 mol) was added to a solution of ammonium carbonate (27.26 g, 0.29 mol) in 200 mL water. The mixture was stirred at 35 C, and (R)-ethyl 2-bromohexanote (53.52 g, 0.24 mol) in 100 mL of nitromethane was added. The reaction mixture was stirred at 42° C. for 48 h, and at 48 C for an additional 12 h. The mixture was cooled and extracted with ethyl acetate, the organic extract was dried (MgSO$_4$), filtered, and the filtrate evaporated under reduced pressure to an oil. The crude product was purified by short-path silica gel column chromatography, eluting with a gradient of 2–5% MeOH—CHCl$_3$, to give 81.4 g (78% based on 5 g of recovered starting amine) of the title compound: $^1$H NMR (DMSO-d$_6$) δ0.82 (t, 3H), 1.15 (dd, 3H), 1.2 (m, 4H) 1.3 (m, 2H), 1.4 (m, 2H), 1.6 (m, 2H ), 2.7 (br d, 2H), 2.6–3.15 (several br m, 4H), 3.22 (2 s,3 H, rotamers), 3.85 (m, 1H), 4.03 (m, 2H), 4.57 (2 s, 2H, rotamers), 7.2 (m, 5H).

C. The resultant compound from Example 74B (35 g, 0.081 mol) was stirred in 112.5 mL 2N NaOH (0.227 mol) at room temperature for 24 h, by which time the cloudy mixture turned clear. The mixture was acidified with aqueous citric acid to pH 5.5, causing a white solid to precipitate. After standing at room temperature for 2 h, the solid was filtered, then washed sequentially with cold water and 20% ether/hexane, and dried under high vacuum to afford 28.4 g of crude product. The crude material was recrystallized from hot ethyl acetate to give the desired compound (27 g, 82%) as a white powder: mp 155°–7° C.; $[\alpha]_D^{25}$ +26.3° (c 0.28, CH$_3$OH); $^1$H NMR (DMSO-d$_6$) δ0.85 (t, 3H), 1.25 (br m, 6H), 1.5 (br m, 4H), 2.75 (dd, 2H), 2.82 (m, 2H), 3.02 (m, 2H), 3.22 (2 s, 3 H, rotamers), 3.45 (m, 1H), 3.58 (m, 1H), 4.0 (m, 1H), 4.55 (2 s, 2H, rotamers), 7.25 (m, 5H); MS m/e 407 ((M+H)$^+$).

EXAMPLE 75

N-((4-Pyridyl)methyl) 5(S)-(N-(1(S)-(4-(methoxymethoxy)piperidin-1-yl)carbonyl-2-phenyl)ethyl-L-norleucinamido)-7-methyl-4(S)-hydroxy-2(R, S)-(2-hydroxyethyl)octanamide The procedure of Example 49B can be employed, with the substitution of the resultant compound from Example 27 (a), U.S. Pat. No. 4,851,387, for the resultant compound from Example 49A, to provide the title compound.

EXAMPLE 76

N-15-Amino-1-cyclohexyl-3(R); 4(S)-dihydroxy-5-methyl-2(S)-hexyl) 5(S)-(N-(1(S)-(4-(methoxymethoxy)piperidin-1-yl)carbonyl-2-phenyl)ethyl-L-norleucinamide A. N-15-Benzyloxycarbonylamino-1-cyclohexyl-3(R), 4(S)-dihydroxy-5-methyl-2(S)-hexyl) 5(S)-(N-(1(S)-(4-(methoxymethoxy)piperidin-1-yl)carbonyl-2-phenyl)ethyl-L-norleucinamide.

The procedure of Example 49B, part 2 can be employed, with the substitution of the resultant compound from Example 5, PCT Patent WO 91/01327, for the resultant compound from Example 49B, part 2, to provide the title compound.

B. The procedure of Example 3 can be employed, with the substitution of the resultant compound from Example 76A for the resultant compound from Example 2, to provide the title compound.

EXAMPLE 77

(2S,4S)-2-[(N-(1(S)-(4-(methoxymethoxy)piperidin-1-yl)carbonyl-2-phenyl)ethyl-L-norleucinamido)]-1-cyclohexyl-4-hydroxy-5-methoxymethoxymethyl-6-methylheptane A. 5(S)-(tert-Butyloxycarbonyl)-6-cyclohexyl-4(S)-hydroxy-2-(S)-isopropylhexanol.

The title compound was prepared using the procedure described in the literature (Karlsson, J. O; Lundblad, A.; Malm, I.; Nilsson, I.; Nitenberg, T.; Starke, I.; Sörensen, H.; Westerlund, C. *Tetrahedron Lett.* 1989, 2653) for the 6-methyl compound, however the analogous isopropyl precursor was used instead. $^1$H NMR (CDCl$_3$, 300 MHz) $\delta$0.90 (dd, J=6 Hz, 6H), 1.13–1.40 (bm, 6H), 1.45 (s, 9H), 1.57–1.90 (bm, 12H), 3.58–3.72 (m, 5H), 4.68 (bd, J=9 Hz, 1H). Anal calcd for C$_{20}$H$_{39}$NO$_4$.0.25H$_2$O: C, 66.30; H, 10.62; N, 3.76. Found: C, 66.14; H, 10.67; N, 3.77. MS (DCI/NH$_3$) m/e 358 (M+H)+.

B. 4-Cyclohexylmethyl-5-(3-methyl-2-hydroxymethyl)-butyl-2-oxazolinone.

The compound resulting from Example 77A was converted to the title compound using the method described in the literature (Karlsson, J. O.; Lundblad, A.; Malm, I.; Nilsson, I.; Nitenberg, T.; Starke, I.; Sörensen, H.; Westerlund, C. *Tetrahedron Lett.* 1989, 2653) for the 4-methyl compound. m.p. 85°–86° C. $^1$H NMR (CDCl$_3$, 300 MHz) $\delta$0.92 (t, J=6 Hz, 6H), 1.15–1.84 (several bm, 17H), 3.52 (m, 1H), 3.68 (dd, J=4.5 Hz, 2H), 4.35 (m, 1H), 5.62 (bs, 1H). Anal calcd for C$_{16}$H$_{29}$NO$_3$: C, 67.89; H, 10.25; N, 4.95. Found: C, 67.72; H, 10.14; N, 4.92. MS (DCI/NH$_3$) m/e 301 (M+H+NH$_3$)+.

C. 4-Cyclohexylmethyl-5-(3-methyl-2-methoxymethoxymethyl)butyl-2-oxazolinone.

To the compound resulting from Example 77B (650 mg, 2.30 mmol) dissolved in anhydrous methylene chloride (20 mL) at ambient temperature was added technical grade chloromethyl methyl ether (0.26 mL, 1.5 equivalents) followed by diisopropylethylamine (0.8 mL, 2 equivalents). The resulting mixture was stirred for 2.0 hours at ambient temperature, at which time additional chloromethyl methyl ether (1.0 mL) and diisoproylethylamine (0.5 mL) were added. After stirring for an additional hour, the solvent was removed under reduced pressure. The residue obtained was flash chromatographed on silica gel eluting with a gradient (25%,30%) of ethyl acetate in hexane to afford the title compound as a white solid (640 mg, 85%). $^1$H NMR (CDCl$_3$, 300 MHz) $\delta$0.88–0.98 (m, dd, J=3.6 Hz, 7H), 1.12–1.85 (several bm, 16H), 3.37 (s, 3H), 3.47–3.58 (m, 3H), 4.28 (m, 1H), 4.60 (s, 2H), 5.74 (bs, 1H).
MS (DCI/NH$_3$) m/e 328 (M+H)+, 345 (M+H+NH$_3$)+.

D. The compound resulting from Example 77C and 3 equivalents of barium hydroxide octahydrate 0.1M in 3:2 dioxane/water was heated at reflux overnight. The cloudy solution was then cooled, filtered through Celite and concentrated under reduced pressure to dryness. The residue obtained was dissolved in ethyl acetate and filtered through Celite again. After removing the solvent under reduced pressure, the amine obtained (>90%) was used without isolation or further purification.

The above amine (260 mg, 0.86 mmol) was coupled with the compound resulting from Example 1 (350 mg, 0.86 mmol) by the procedure described in Example 49B, part 2 to afford, after column chromatography on silica gel eluting with 3:1 hexane/ethyl acetate, the title compound (505 mg, 84%) as an oil. $^1$H NMR (CDCl$_3$, 300 MHz) $\delta$0.74–0.96 (m, t, J=6.6 Hz, 10H), 1.07–1.80 (several bm, 33H), 2.67–2.89 (m, 5H), 3.33 (s, 3H), 3.40 (s, 3H), 3.52–3.78 (bm, 4H), 4.65 (dd, J=1.5 Hz, 4H), 7.27 (m, 5H). MS (FAB) m/e 690 (M+H)+.

EXAMPLE 78

(2S,4S)-2-[(N-(1(S)-(4-(methoxymethoxy)piperidin-1-yl)carbonyl-2-phenyl)ethyl-L-norleucinamido))-1-cyclohexyl-3-hydroxy-5-isopropylthiomethyl-6-methylheptane A. Isopropyl [5(S)-(tert-butyloxycarbonylamino)-6-cyclohexyl-4(S)-hydroxy-2-(S)-isopropylhexyl] thioether.

The title compound was prepared using the procedure described in the literature (Karlsson, J. O.; Lundblad, A.; Malm, I.; Nilsson, I.; Nitenberg, T.; Starke, I.; Sörensen, H.; Westerlund, C. *Tetrahedron Lett.* 1989, 2653) for the 6-methyl compound, however the analogous isopropyl precursor was used instead. m.p. 107°–108° C. $^1$H NMR (CDCl$_3$, 300 MHz) $\delta$0.85–1.00 (m, dd, J=6 Hz, 7H), 1.15–1.38 (m, d, J=6 Hz, 9H), 1.45 (p, J=6 Hz, 1H), 1.58–1.92 (m, 12H), 2.52 (dd, J=6 Hz, 1H), 2.63 (dd, J=4.5 Hz, 1H), 2.87 (p, J=6 Hz, 1H), 3.64 (q, J=7.5 Hz, 1H), 4.29 (m, 1H), 5.20 (bs, 1H). MS (DCI/NH$_3$) m/e 342 (M+H)+, 359 (M+H+NH$_3$)+.

B. The compound resulting from Example 78A was treated with barium hydroxide octahydrate by the procedure described in Example 77D. This compound was coupled with the compound resulting from Example 1 (250 mg, 0.62 mmol) by the procedure described in Example 49B, part 2 to afford the title compound (357 mg, 82%) as an oil. Rf=0.28 (50% hexane-ethyl acetate) $^1$H NMR (CDCl$_3$, 300 MHz) $\delta$0.75–0.95 (m, 10H), 1.08–1.39 (m, d, J=6.9 Hz, 20H), 1.48–1.86 (bm, 18H), 2.40–2.59 (m, 3H), 2.81 (bm, 3H), 2.92 (p, 1H), 3.26–3.48 (m, s, 4H), 3.68 (bm, 3H), 4.64 (d, J=3 Hz, 2H), 7.26 (m, 5H).

EXAMPLE 79

(2S,4S)-2-[(N-(1(S)-(4-(methoxymethoxy)piperidin-1-yl)carbonyl-2-phenyl)ethyl-L-norleucinamido))-1-cyclohexyl-3-hydroxy-5-isopropylsulfonylmethyl-6-methylheptane A. Isopropyl [5(S)-(tert-butyloxycarbonylamino)-6-cyclohexyl-4(S)-hydroxy-2-(S)-isopropylhexyl] thiosulfonate.

The compound resulting from Example 78a was oxidized using the procedure described in the literature (Karlsson, J. O.; Lundblad, A.; Malm, I.; Nilsson, I.; Nitenberg, T.; Starke, I.; Sörensen, H.; Westerlund, C. *Tetrahedron Lett.* 1989, 2653) for the 6-methyl compound to afford the title compound. m.p. 135°–136° C. $^1$H NMR (CDCl$_3$, 300 MHz) δ0.98–1.03 (m, dd, J=6 Hz, 7H), 1.10–1.35 (m, 4H), 1.37–1.48 (m, d, J=6 Hz, 7H), 1.57–2.30 (several bm, 11H), 2.77–2.97 (m, 2H), 3.11 (p, J=6 Hz, 1H), 3.58 (q, J=7.5 Hz, 1H), 4.33 (m, 1H), 5.15 (bs, 1H).

B. The compound resulting from Example 79A was treated with barium hydroxide octahydrate by the procedure described in Example 77D. This compound is then coupled with the compound resulting from Example 1 by the procedure described in Example 49B, part 2 to afford the title compound.

EXAMPLE 80

(2S,4S,5S) 5-Amino-6-cyclohexyl-2-isopropyl-4-hexanolide

EXAMPLE 80a

2(S)-Cyclohexylalanine methyl ester, hydrochloride salt

L-Phenylalanine (215 g, 1.3 mole) was hydrogenated over Pd/C in HOAc, filtered and concentrated. The resulting cyclohexylalanine was taken up in MeOH (1200 mL). Thionyl chloride (427 g, 3.59 mole) was slowly added to the slurry, which eventually became homogeneous. The reaction was cooled in an ice/water bath and addition of thionyl chloride was continued. The reaction mixture was heated to reflux for 2 h, cooled and concentrated to afford a solid, which was taken up in ether and filtered. The white solid was washed with ether in the filter funnel and dried in vacuo to give 271 g of product, 94% yield over two steps. mp 150°–152° C.; [α]$_D$=+21.8° (c=1.09, MeOH); IR (KBr, cm$^{-1}$) 2930(br), 2860, 1748; $^1$H NMR (300 MHz, CDCl$_3$) δ3.99 (t, J=6.3 Hz, 1H), 3.9 (bs, 2H), 3.83 (s, 3H), 1.82–1.65 (m, 7H), 1.5 (m, 1H), 1.35–1.10 (m, 3H) 1.05–0.9 (m, 2H); $^{13}$C NMR (75.5 Hz, CDCl$_3$) ppm 170.5, 53.3, 50.8, 38.3, 33.6, 33.0, 32.8, 26.3, 26.1, 25.9.

EXAMPLE 80b

2(S)-N-(Triphenylmethyl)cyclohexylalanine methyl ester

The product of Example 80a (88 g, 398 mmol) was taken up in chloroform (400 mL). Triethylamine (84.6 g, 836 mmol) was then added in one portion to the slurry and stirred five minutes. Triphenylmethylchloride (111 g, 398 mmol) was then added, and the reaction was stirred for 5 h at ambient temperature. The internal temperature of the reaction reached 50° C., however, external cooling was not employed. The reaction mixture was washed with 1M KHSO$_4$ solution (2×200 mL), saturated NaHCO$_3$ (200 mL), brine (100 mL), then dried over MgSO$_4$. The solution was then concentrated to give 200 g of residue which was filtered through 900–1000 g of silica gel (elution gradient hexane-10:1 hexane: ethyl acetate) affording 157 g of product (93%), which could be crystallized from hexanes: ethyl acetate to afford large white crystals.

mp 86°–87° C.; [α]$_D$=+73.6° (c=1.38, CHCl$_3$); IR (KBr, cm$^{-1}$) 3450(br), 2930, 1722; $^1$H NMR (300 MHz, CDCl$_3$) δ7.52–7.47 (m, 6H), 7.28–7.12 (m, 9H), 3.32–3.41 (m, 1H), 3.12 (s, 3H), 2.60 (d, J=10.5 Hz, 1H), 1.56–1.46 (m, 7H), 1.35–1.1 (m, 4H), 0.77–0.97 (m, 2H); $^{13}$C NMR (75.5 Hz, CDCl$_3$) ppm 176.1, 146.0, 128.8, 127.7, 126.3, 71.0, 54.2, 51.2, 44.4, 34.1, 33.9, 32.9, 26.5, 26.1.

EXAMPLE 80c

Dimethyl 3(S)-4-Cyclohexyl-3-(N-triphenylmethyl)amino-2-oxobutylphosphonate

To a −78° C. solution of dimethyl methylphosphonate (272.5 g, 2.2 mol) in 1.6 L THF was added n-BuLi (2.5M, 800 mL, 2.0 mmol) and stirred 45 minutes. The product of Example 80b (156 g, 366 mmol) in 40 mL THF was then added dropwise. The reaction mixture was stirred at −50° C. for 3 h, then at −40° C. for 6 h, then finally warmed to ambient temperature overnight. The reaction mixture was concentrated, taken up in ether, washed with 1M KHSO$_4$, saturated NaHCO$_3$ (twice) and brine, dried and concentrated. The residue (200 g) was filtered through 1000 g silica gel, (1:1 hexanes:ethyl acetate) to give 135 g of β-keto phosphonate (72%) as an oil.

[α]$_D$=+39.7° (c=2.0, CH$_3$OH); IR (CDCl$_3$, cm$^{-1}$) 2920, 1717, 1425, 1226, 1019; $^1$H NMR (300 MHz, CDCl$_3$) δ7.45–7.38 (m, 6H), 7.30–7.18 (m, 9H), 3.67 (dd, J=11.1, 2.7 Hz, 6H), 3.47 (m, 1H), 2.83 (d, J=6.6 Hz, 1H), 2.67 (dd, J=21.0, 15.3 Hz, 1H), 2.32 (dd, J=21.0, 15.3 Hz, 1H), 1.65 (bs, 5H), 1.49 (m, 2H), 1.10–1–53 (m, 4H), 0.81 (m, 2H); $^{13}$C NMR (75.5 Hz, CDCl$_3$) ppm 205.8, 145.9, 129.1, 127.9, 127.7, 126.7, 71.2, 61.4, 61.3, 52.8, 52.7, 52.6, 41.4, 37.1, 35.2, 33.8, 33.5, 33.4, 26.4, 26.2, 26.1.

EXAMPLE 80d (6S)-7-Cyclohexyl-2-methyl-6-(N-triphenylmethyl)-amino-5-oxohept-2-ene-3-oic acid The product of Example 80c (117.2 g, 229 mmol) was dissolved in 600 ml THF and cooled to 0° C. To this solution was added hexanes washed NaH (60%, 9.6 g (wet), 240 mmol) and stirred 30 min. Next was added methyl 3-methyl-2-oxobutyrate (29.8 g, 229 mmol) in 100 ml THF and stirred at 0° C. for 4 h. Volatiles were removed at reduced pressure, the residue was dissolved in 1:1 hexanes: ether (500 ml) and washed with water (200 ml), NaHCO$_3$ (200 ml), brine (200 ml), dried (MgSO$_4$) and concentrated to afford 129 g of the desired ester as an oil. This material (123 g) was taken up in 460 ml THF, 229 ml MeOH, cooled to 0° C. then 18.86 g of LiOH—H$_2$O in 229 ml of distilled water was added. This solution was allowed to warm to room temperature and stirred for 3 days. Volatiles were removed at reduced pressure and the resulting aqueous solution was washed with ether (100 ml×2) then acidified to pH 3 with 6N HCl. The aqueous solution was then extracted with EtOAc (300 ml×2), washed with brine, dried (MgSO4) and concentrated to give 116 g of a yellow foam. This material was recrystallized from 525 ml of hot hexanes/EtOAc (12/1) to give 72.4 g of a white solid (62% for three steps).

mp 97°–98° C.; $[\alpha]_D = +6.0°$ (c=1.0, CH3OH); IR (KBr, cm$^{-1}$) 3450(br), 2930, 1715, 1682, 1442; $^1$H NMR (300 MHz, CDCl3) δ7.48–7.36 (m, 6H), 7.31–7.12 (m, 9H), 3.5 (bs, 1H), 3.25 (d, J=18 Hz, 1H), 2.99 (d, J=18H, 1H), 2.1 (bs, 4H), 1.6 (bs, 8H), 1.2–1.05 (m, 6H), 0.8–0.6 (m, 2H).

EXAMPLE 80e (5S,6S)-6-Cyclohexylmethyl-3-isopropylidene-5-hydroxypiperidine-2-one A solution of 3.06 g (6.0 mmol) of the product of Example 80d in 50 ml THF was added to 6.8 g (60 mmol) N-hydroxysuccinimide. This homogeneous solution was cooled to 0° C. then DCC (1. 25 g, 12 mmol) in 5 ml THF was added. The cooling bath was removed and the reaction was stirred for 2 h. Then an additional 1.25 g of DCC was added. After 5 h of total reaction time, the mixture was filtered, concentrated and dissolved in ether. The organics were washed with NaHCO3 (aq, 50 ml×2), brine, dried (MgSO4) and concentrated at reduced pressure to give 5.2 g of product as an oil, which was dissolved in 20 ml ether. A 1N solution of HCl/Ether (30 ml) was added. A gummy solid immediately precipitated out of solution; CH2Cl2 (25 ml) was added and the clear reaction mixture was stirred overnight. After 12 h, the product, which precipitated from the mixture was collected by filtration and washed with ether to give, after drying, 2.1 g of a white solid in 87% for two steps, which was taken on in the following step.

To a 0° C. slurry of the above-mentioned white solid from the first step of Example 80e (1.2 g, 3.0 mmol) in 20 ml CH2Cl2 was added imidazole (204 mg, 3.0 mmol). The resulting reaction mixture was stirred for 1 h, then washed with 20 ml of KHSO4, water, saturated NaHCO3, and brine. The organic portion was dried over MgSO4, filtered and cooled to −78° C. To the cold solution was added L-Selectride ® (Aldrich, 1.0M, 5.0 ml, 5.0 mmol) and stirred for 10 min. The reaction mixture was then warmed to −40° C. and quenched with 20% citric acid solution. The organics were washed with 20 ml of water, saturated NaHCO3 solution, brine, dried over MgSO4, and concentrated to afford a clear oil. The oil was purified on silica gel (50% hexanes/ethyl acetate) to give an oil which was triturated with ether to afford a white solid, 545 mg, 72% yield.

mp 128°–130° C.; $[\alpha]_D = -66.3°$ (c=1.0, CH3OH); IR (KBr, cm$^{-1}$) 3350(br), 2930, 1640, 1603; $^1$H NMR (300 MHz, CDCl3) δ5.82 (bs, 1H), 3.95 (bs, 1H), 3.42 (m, 1H), 2.88 (bs, 1H), 2.72 (m, 1H), 2.55 (m, 1H), 2.25 (s, 3H), 1.8 (s, 3H), 1.77–1.6 (m, 5H), 1.52–1.34 (m, 3H), 1.28–1.12 (m, 3H), 1.0–0.83 (m, 2H); $^{13}$C NMR (75.5 Hz, CDCl3) ppm 168.1, 148.0, 119.4, 66.3, 53.1, 38.4, 35.3, 33.7, 33.6, 32.9, 26.4, 26.1, 26.0, 23.2, 23.0.

EXAMPLE 80f (3S,5S,6S)-6-Cyclohexyl-5-hydroxy-3-isopropyl-piperidin-2-one

A solution of the product of Example 80e (24.7 g, 98.4 mmol) in 500 ml of ethyl acetate was treated with 2.5 g of dry Pd/C and hydrogenated at 4 atm for 4 h at ambient temperature. The reaction mixture was filtered and concentrated to a white foamy solid which was taken on without further purification.

mp 97°–99° C.; $[\alpha]_D = -95.1°$ (c=1.075, CHCl3); IR (KBr, cm$^{-1}$) 3605, 3400, 2925, 1642; $^1$H NMR (300 MHz, CDCl3) δ6.3 (bs, 1H), 4.11 (m, J=4.5, 1H), 3.47 (m, 1H), 2.72 (bs, 1H), 2.5 (m, 1H), 2.3 (m, 1H), 1.9 (m, 1H), 1.8–1.5 (m, 8H), 1.43–1.12 (m, 6H), 0.97 (d, 3H), 0.87 (m, 3H); $^{13}$C NMR (75.5 Hz, CDCl3) ppm 174.2, 67.1, 52.6, 44.3, 37.7, 34.5, 33.8, 32.4, 27.6, 26.4, 26.3, 26.2, 26.0, 20.2, 17.4.

EXAMPLE 80g (2S,4S,5S) 5-Amino-6-cyclohexyl-2-isopropyl-4-hexanolide

The product of Example 80f was dissolved in 200 ml of 6N HCl and 50 ml of ethanol then heated to reflux for 14 h. The reaction mixture was concentrated at reduced pressure and azeotropically dried with toluene to afford a pale oil. This material was taken up in water and extracted with hexane, then made basic by addition of a solution of NaHCO3. Extraction with ethyl acetate followed by drying (MgSO4) and removal of volatiles afforded a yellowish oil which solidified to a white solid upon standing. Recrystallization from hexane gave 20.7 g (90%) of product as white needles.

mp 49°–50° C. (lit. mp 48°–49° C.); (KBr, cm$^{-1}$) 2925, 1760; $^1$H NMR (300 MHz, CDCl3) δ4.2 (q, J=6.1 Hz, 1H), 2.82 (q, J=6.2 Hz, 1H), 2.64 (ddd, J=9.1, 6.0, 5.4 Hz, 1H), 2.15 (m, 1H), 2.08 (m, 2H), 1.8–1.61 (m, 6H), 1.46 (m, 1H), 1.37–1.13 (m, 8H), 1.02 (d, J=6.0 Hz, 3H), 0.96 (d, J=6.0 Hz, 3H); $^{13}$C NMR (75.5 Hz, CDCl3) ppm 178.9, 83.1, 52.6, 46.0, 41.3, 34.4, 33.7, 32.3, 29.2, 26.8, 26.5, 26.3, 26.0, 20.3, 18.5. $[\alpha]_D = +6.5°$ (c=1.0, EtOH).

EXAMPLE 81

(S)-1-(2-Furyl)-1-pentanol

EXAMPLE 81A

Racemic 1-(2-furyl)-1-pentanol

Freshly distilled furfural (233.5 g, 2.43 mol) was dissolved in 200 mL freshly distilled THF and added dropwise to a solution of butylmagnesium bromide (2.0M in THF, 1460 mL, 2.92 mol) at 0° C. under dry nitrogen. After the addition was complete, the mixture was allowed to warm to room temperature overnight. The reaction was recooled to 0° C. and carefully poured into 2 L of cold sat. NH4Cl. The layers were separated, and the aqueous phase was extracted with ether. The combined organic layers were washed with saturated NaCl, dried over MgSO4, evaporated, and vacuum distilled to give 325.6 g (87%): bp 72°–73° C. (0.6 mmHg); $^1$H NMR (300 MHz, CDCl3) d 7.38 (1H, dd J=1 Hz), 6.33 (1H, m), 6.22 (1H, dd, J=3 Hz), 4.67 (1H, t, J=6 Hz), 2.9 (3H, m), 1.35 (4H, m), 0.90 (3H, t, J=7 Hz); mass spectrum (FAB): 170 (M+NH4).

EXAMPLE 81B (S)-1-(2-Furyl)-1-pentanol

To a room temperature solution of the racemic 1-(2-furyl)pentanol (20 g, 0.1298 mol) and diisopropyl D-tartrate (4.45 g, 0.019 mol) in methylene chloride (80 mL) were added activated powdered molecular sieves 4 A (6 g). The stirred mixture was cooled to −35° C. treated with titanium tetraisopropoxide (3.7 g, 0.1298 mol), and stirred for 30 m at the same temperature. The reaction mixture was treated with a solution of t-butylhydroperoxide in 2,2,4-trimethylpentane (30 mL, 0.0908 mol) and was stirred at −35° C. for 3 h and allowed to warm up to −10° C. in 2 h. A freshly prepared solution of iron II sulfate.7H$_2$O (7.2 g, 20 mmol) and dl-tartrate (23 g) in 120 mL water was added to the reaction mixture at −20° to −30° C. and the resulting mixture was stirred vigorously without cooling for 30 m until two clear phases appeared. The organic layer was separated and the aqueous phase was extracted with methylene chloride. The combined organic layer was washed with brine and dried over sodium sulfate. Evaporation of the solvent gave the crude product, which was distilled to give 6 g of the desired product, bp 70°–75° C. (0.7 mmHg) and 12 g of the pyranol, bp 115° C. (0.7 mmHg). Redistillation of the mixed fractions gave additional 0.4 g. A total of 6.4 g of the desired product was obtained (75% theoretical yield based on 60% conversion to the pyranol): $[\alpha]^{25}_D = -18°$ (c 1.0, CHCl$_3$), 99% ee by chiral column chromatography analysis (Lit. reported −9°, 94% ee).

EXAMPLE 82

Alternative Preparation of (S)-1-(2-Furyl)-1-pentanol

To a solution of optically active (−) 3-exo-(dimethylamino) isoborneol (DAIB, see Noyori et. al. *J. Am. Chem. Soc.* 1986, 108, 6071-2 and Noyori et al. *J. Organomet. Chem.* 1990, 382, 19-37, 371 mg, 1.88 mmol) in 200 mL of dry toluene under an argon atmosphere is added a 4.2M solution of di-butylzinc (25 mL, 105 mmol) at room temperature. The reaction mixture is stirred for 15 m and then cooled to −78° C. To the cooled solution is added freshly distilled furfural (9.0 g, 94 mmol) in one portion. The reaction mixture is stirred at 0° C. for 6 h. Saturated ammonium chloride solution (100 mL) is added. The mixture is extracted three times with diethyl ether. The combined organic layers are dried (MgSO$_4$) and concentrated under reduced pressure. Bulb-to-bulb distillation of the residue (100° C. 20 mmHg) gives the alcohol which is identical to the sample prepared in example 81B.

EXAMPLE 83

Alternative Preparation of (S)-1-(2-Furyl)-1-pentanol

EXAMPLE 83A

2-Valeryl furan

Furan (12 g, 0.177 mol) and valeryl anhydride (37.2 g, 0.2 mol) were placed in the flask. The reaction mixture was cooled at 0° C. in an ice-bath. To the rapidly stirring reaction mixture, 3 g of freshly distilled boron trifluoride-etherate was added all at once. The ice-bath was removed and the temperature of the reaction mixture rose to 65° C. Stirring was continued for 2 h at 60° C., and about 200 mL water was added and stirred for additional 2 h. The phases were separated and the aqueous phase was extracted with chloroform. The chloroform portion was added with 200 mL of saturated sodium bicarbonate and stirred for ½ h. The organic layer was separated, washed with water, dried and filtered. The filtrate was evaporated to a liquid which was distilled at 65°–70° C. (2 mmHg) to yield 20 g (75%) of the desired product: $^1$H NMR δ0.95 (t, 3H), 1.4 (m, 2H), 1.7 (m, 2H), 2.82 (t, 2H), 6.52 (dd, 1H), 7.2 (d, 1H), 7.6 (d, 1H).

EXAMPLE 83B (S)-1-(2-Furyl)-1-pentanol 10.4 mmol (10.4 mL) of diborane (1M solution in THF) was added dropwise in a period of 10 m at room temperature to a solution of 2-valeryl furan (2.62 g, 17.2 mmol) and 1.68 mmol (4.2 mL) of (3aR)-1,3,3-triphenyl pyrrolidino [1,2-c] [1,3,2] oxazaborole (see E. J. Corey et al. *J. Am. Chem. Soc.* 1987, 109, 7925-26, 0.4M solution in THF) in 25 mL THF. The reaction mixture was stirred for 20 m and was cooled to 10° C. 6 mL methanol was cautiously added and followed by adding 62 mg HCl (by weight) in ether. Stirred for 0.5 h, white solid was precipitated out. The cloudy mixture was poured into 100 mL ether and 100 mL water. The organic layer was separated, washed with saturated sodium bicarbonate, water, brine, dried and filtered. The filtrate was evaporated to an yellowish oil which was chromatographed eluting with 10% ethyl acetate in hexane to obtain 70% of the product. $[\alpha]^{25}_D = -13°$, 60% ee by Mosher' ester analysis.

EXAMPLE 84

(4S) 4-(2-furyl)-3-oxaoctanoic acid

NaH (16.3 g, 680.9 mmol) and freshly distilled THF (170 mL) were stirred at room temperature as (S)-1-(2-furyl)-1-pentanol ($[\alpha]^{25}_D - 17.2°$, 30.0 g, 46.0 mmol) in THF (170 mL) was added dropwise. After the addition was complete, the mixture was stirred for 15 m before cautiously heating to reflux for 1 h. The mixture was cooled to 0° C. before adding dropwise a solution of bromoacetic acid (27.3 g, 196.5 mmol) in THF (40 mL). The mixture was refluxed 2 days before cooling and carefully pouring into 600 mL ice water. The aqueous was washed with ether and acidified with HCl to pH 4, and extracted with ether. The combined organic extracts were washed with brine, dried over MgSO$_4$, and evaporated to give a quantitative yield of crude product which was used in the next step without further purification.

EXAMPLE 85

(4S) Methyl 4-(2-furyl)-3-oxaoctanoate

Crude acid from example 84 (25 g, 118 mmol) was dissolved in ether and treated with excess diazomethane (generated by adding 1-methyl-3-nitro-1-nitrosoguanidine (MNNG) to a mixture of 40% KOH (aq) and ether at 0° C.). Excess diazomethane was quenched with acetic acid after 30 m. Vacuum distillation gave 18.8 g (70%): $[\alpha]^{25}_D - 100°$; bp 100°–109° C. (0.5 mmHg); $^1$H NMR (300 MHz, CDCl$_3$) δ7.40 (1H, dd, J=1 Hz), 6.34 (1H, dd, J=1 Hz), 6.29 (1H, dd, J=1 Hz), 4.43 (1H, t, J=7 Hz), 4.00 (2H, q, J=16 Hz), 3.72 (3H, s), 1.92 (2H, m), 1.33 (4H, m), 0.89 (3H, t, J=7 Hz); mass spectrum (FAB): 244 (M+NH$_4$).

EXAMPLE 86

(4S) t-Butyl 4-(2-furyl)-3-oxaoctanoate

A solution of (S)-1-(2-furyl)-1-pentanol $[\alpha]^{25}_D - 15°$ (c 1, CHCl$_3$), 30.0 g, 194.5 mmol] in 250 mL dry DMF was stirred at 0° C. under dry nitrogen as KN(TMS)$_2$ (0.5M in toluene, 390 mL, 195 mmol) was added dropwise. After stirring 15 m, t-butyl bromoacetate was added. The mixture was stirred at 0° C. for 2 h before slowly warming to rt and stirring overnight. The reaction mixture was cooled to 0° C. diluted with an equal volume of ether, and treated with 1 L saturated NH$_4$Cl. The combined ether extracts were washed with saturated NH$_4$Cl, 5% NaHCO$_3$, and brine, dried over MgSO$_4$, and evaporated to give 54 g crude product. Vacuum distillation gave 21.0 g (40%) pure product and a side fraction of 8.0 g (15%): [α]$^{25}_D$−73° (c 1.19, CHCl$_3$); bp 110° C. (0.5 mmHg); $^1$H NMR (300 MHz, CDCl3) δ7.40 (1H, dd, J=1 Hz), 6.34 (1H, dd, J=3 Hz), 6.28 (1H, dd, J=5 Hz), 4.44 (1H, t, J=7 Hz), 4.37 (2H, q, J=21 Hz), 1.9 (2H, m), 1.47 (9H, s), 1.4 (6H, m), 0.89 (3H, t, J=7 Hz); mass spectrum (FAB): 286 (M+NH$_4$).

EXAMPLE 87

(4S) Benzhydryl 4-(2-furyl)-3-oxaoctanoate

To a suspension of 4.08 g (165 mmol) of 97% sodium hydride in 50 mL of dry THF at rt was added 10.5. g (68 mmol) of (S) 1-(furyl)-1-pentanol. After addition, the reaction was heated at reflux temperature for 2 h, cooled to 0°-5° C. in an ice-water bath, and 9.5 g (102 mmol) of bromoacetic acid in 50 mL of THF was added. After addition was complete, the reaction mixture was heated at reflux temperature for 2 d, cooled to 0°-5° C. and water slowly added. The reacture mixture was extracted with ether. The aqueous layer was acidified with 1N HCl to pH 5-6 and the crude acid was extracted with ether, dried (MgSO$_4$) and concentrated to a crude oil.

Benzophenone hydrazone (13.3 g, 68 mmol) and 14.7 g (68 mmol) of HgO in 150 mL of hexane were stirred for 24 h. The resulting purple solution was filtered and concentrated to ⅓ the volume. The crude acid in ether was added to the purple hexane solution of diphenyldiazomethane and was stirred for 24 h. Excess acetic acid (5 mL) was added and the reaction stirred an additional 30 m, poured into saturated NaHCO$_3$. After ethyl acetate extraction the crude benzhydryl ester (19 g) was purified by silica gel chromatography using (3:97)ethyl acetate:hexane as eluant to give 18 g (72% yield) of benzhydryl ester as a yellow oil.

[α]$^{25}_D$= −74.86.9° (c 2.3, CHCl$_3$); IR (film) 1740, cm$^{-1}$; $^1$H NMR (300 MHz, CDCl$_3$) δ7.2-7.40 (m, 11H), 6.95 (s, 1H), 6.29 (dd, J=1.5, 3 Hz, 1H), 6.21 (br d, 1H), 4.46 (t, J=7 Hz, 1H), 4.14 (d, J=16 Hz, 1H) 4.01 (d, J=16 Hz, 1H), 1.77-2.05 (m, 2H), 1.13-1.44 (m, 4H), 0.86 (t, J=7 Hz, 3H); mass spectrum (FAB) 379 (M+H).

Anal. Calcd for C$_{24}$H$_{26}$O$_4$: C, 76.19; H, 6.87. Found: C, 76.94; H, 6.77.

EXAMPLE 88

(2S,4S) Methyl 2-benzyl-4-(2-furyl)-3-oxaoctanoate and (2R,4S) Methyl 2-benzyl-4-(2-furyl)-3-oxaoctanoate (4S) Methyl 4-(2-furyl)-3-oxaoctanoate (5.0 g, 22.1 mmol) in 40 mL freshly distilled THF was added dropwise to a solution of NaN(TMS)$_2$ (1.0M in THF, 22.1 mL, 22.1 mmol) at −80°±5° C. After 5 m, freshly filtered (through basic alumina) benzyl bromide (3.0 mL, 25.2 mmol) was added dropwise maintaining the reaction temperature at −80°±5° C. After 30 m, the reaction was warmed to 0° C. for 1 h before quenching with water. The mixture was extracted with ether. The combined ether extracts were washed with saturated NH$_4$Cl, 5% NaHCO$_3$, brine, and dried over MgSO$_4$. Purification of the residue by flash silica gel chromatography gave 1.2 g of the less polar (2S, 1S) diastereomer and 1.6 g of the more polar (2R, 1S) diastereomer, (18 and 25%, respectively, based upon a 7% recovery of unreacted starting material [[α]$^{25}_D$−84° (c 1.14, CHCl$_3$)]. (2S, 1S) diastereomer: [α]$^{25}_D$−74° (c 1.11, CHCl$_3$); $^1$H NMR (250 MHz, CDCl$_3$) δ7.19 (6H, m), 6.21 (1H, dd, J=1 Hz), 5.91 (1H, dd, J=1 Hz), 4.37 (1H, t, J=7 Hz), 4.06 (1H, dd, J=7 Hz), 3.69 (3H, s) 2.94 (2H, m), 1.83 (2H, m), 1.29 (4H, m), 0.88 (3H, t, J=7 Hz); mass spectrum (FAB): 334 (M+NH$_4$). (2R, 1S) diastereomer: [α]$^{25}_D$−53° (c 1.23, CHCl$_3$); $^1$H NMR (250 MHz, CDCl$_3$) δ7.37 (1H, m), 7.27 (5H, m), 6.38, (1H, dd, J=1 Hz), 6.19 (1H, dd, J=1 Hz), 4.08 (2H, m), 3.49 (3H, s), 2.98 (2H, d, J=7 Hz), 1.91 (1H, m), 1.72 (1H, m), 1.2 (4H, m), 0.79 (3H, t, J=7 Hz); mass spectrum (FAB): 334 (M+NH$_4$).

EXAMPLE 89

(2S,4S) t-Butyl 2-benzyl-4-(2-furyl)-3-oxaoctanoate and (2R, 4S) t-Butyl 2-benzyl-4-(2-furyl) -3-oxaoctanoate (4S) t-Butyl 4-(2-furyl)-3-oxaoctanoate ([α]$^{25}_D$−73° (c 1.19, CHCl$_3$), 10.0 g, 37.3 mmol) in 100 mL freshly distilled THF was added dropwise to a solution of NaN(TMS)$_2$ (1.0M in THF, 37.3 mL, 37.3 mmol) at −85°±5° C. After 5 m, freshly distilled and filtered (through basic alumina) benzyl bromide (5.0 mL, 42.0 mmol) was added dropwise maintaining the reaction temperature at −85°±5° C. After 30 m, the reaction was warmed to 0° C. for 1 h before quenching with water. The mixture was extracted with ether. The combined ether extracts were washed with saturated NH$_4$Cl, 5% NaHCO$_3$, brine, and dried over MgSO$_4$. Purification by flash silica gel chromatography (1:1) ethyl acetate:hexane gave 2.1 g (15%) of the less polar (2S,1S) diastereomer, 2.4 g (18%) of the more polar (2R,1S) diastereomer, and 2.0 g of a mixture of starting material and the two diastereomers. (2S, 1S) diastereomer: [α]$_D^{25}$−65° (c 1.19, CHCl$_3$); $^1$H NMR (300 MHz, CDCl$_3$) δ0.88 (3H, t, J=7 Hz), 1.3 (4H, m), 1.40 (9H, s), 1.83 (2H, m), 2.93 (2H, m), 3.91 (1H, dd, J=6 Hz), 4.38 (1H, t, J=7 Hz), 5.92 (1H, d, J=4 Hz), 6.22 (1H, dd, J=1 Hz), 7.20 (6H, m); mass spectrum (FAB): 376 (M+NH$_4$). (2R,1S) diastereomer: [α]$^{25}_D$−30° (c 1.26, CHCl$_3$); $^1$H NMR (300 MHz, CDCl$_3$) δ0.79 (3H, t, J=7 Hz), 1.15 (4H, m), 1.29 (9H, s), 1.69 (1H, m), 1.85 (1H, m), 2.95 (2H, m), 3.98 (1H, dd, J=7 Hz), 4.10 (1H, t, J=7 Hz), 6.20 (1H, dd, J=1 Hz), 6.28, (1H, dd, J=1 Hz), 7.26 (5H, m), 7.36 (1H, dd, J=1 Hz); mass spectrum (FAB): 376 ( M+NH$_4$)

EXAMPLE 90

(2S,4S) Benzhydryl 2-Benzyl-4-(2-furyl)-3-oxaoctanoate (4S) Benzhydryl 4-(2-furyl)-3-oxaoctanoate (2.0 g, 5.28 mmol) was dissolved in 20 mL freshly distilled THF and cooled to −80°±5° C. under dry argon. Sodium bis(trimethylsilyl)-amide (1.0M in THF, 5.6 mL, 5.6 mmol) was slowly added keeping the temperature at −80°±5° C. After 15 m, freshly distilled and filtered (through basic alumina) benzyl bromide (0.7 mL, 5.81 mmol) in HMPA (4 mL) was added dropwise maintaining the reaction temperature at −75°±5° C. After 15 m, the reaction was allowed to warm to 0° C. for 1 h before quenching with water and extraction with ether. The combined ether extracts were washed with saturated NH$_4$Cl, 5% NaHCO$_3$, brine,dried over MgSO$_4$, and purified by flash silica gel chromatography to give 771.3 mg (31%): [α]$^{25}_D$−65.5°; $^1$H NMR (300 MHz, CDCl$_3$) δ0.81 (t, 3H, J=7 Hz), 1.22 (m, 4H), 1.80 (m, 2H), 2.91 (m, 2H), 4.12 (dd, 1H, J=9 Hz), 4.30 (t, 1H, J=7 Hz), 5.86 (m, 1H), 6.19 (m, 1H), 6.69 (s, 1H), 7.2 (m, 16H); mass spectrum (FAB): 486 (M+NH$_4$).

EXAMPLE 91

(2R,4S) Benzhydryl 2-Benzyl-4-(2-furyl)-3-oxaoctanoate

Using the procedure in example 90 and (4S) benzhydryl 4-(2-furyl)-3-oxaoctanoate (5.0 g, 13.2 mmol), THF (50 mL), sodium bis(trimethylsilyl)amide (1.0M in THF, 14 mL, 14 mmol), and benzyl bromide (1.7 mL, 14 mmol) in 10 mL HMPA gave (2R,4S) benzhydryl 2-Benzyl-4-(2-furyl)-3-oxaoctanoate, 646.6 mg (10%) and 723 mg (12%) of the (2S 4S) diastereomer which was identical to the sample prepared in example 90. (2R,4S) diastereomer: $[\alpha]^{25}_D$—34.8° (c 1.12, CHCl$_3$); $^1$H NMR (300 MHz, CDCl$_3$) δ0.78 (t, 3H, J=7 Hz), 1.12 (m, 4H), 1.69 (m, 1H), 1.83 (m, 1H), 2.98 (m, 2H), 4.11 (t, 1H, J=7 Hz), 4.21 (dd, 1H, J=8 Hz), 6.07 (m, 2H), 6.72 (s, 1H), 7.26 (m, 16H); mass spectrum (FAB): 486 (M+NH$_4$).

EXAMPLE 92A

N-4-Methoxymethoxypiperidine Amide of (2S,4S) 2-Benzyl-4-(2-furyl)-3-oxaoctanoic Acid (2S,4S) Benzhydryl 2-benzyl-4-(2-furyl)-3-oxaoctanoate (502 mg, 1.07 mmol) was dissolved in EtOAc (3 mL) and shaken under 4 atm. H$_2$ with 10% Pd/C (50 mg) at room temperature. Filtration and evaporation gave 468.4 mg of product which contains diphenylmethane: $^1$H NMR δ0.88 (t, 3H, J=7 Hz), 1.29 (m, 4H), 1.83 (m, 2H), 2.99 (m, 2H), 4.42 (m, 1H), 4.53 (dd, 1H, J=8 Hz), 5.96 (d, 1H, J=3 Hz), 6.22 (dd, 1H, J=3 Hz), 7.21 (m, 5H); mass spectrum (FAB) 320 (M+NH$_4$).

The product from above reaction, 4-methoxymethoxypiperidine (0.16 g, 1.07 mmol), and 4-hydroxybenzotriazole (0.44 g, 2.89 mmol) were dissolved in DMF (10 mL) and cooled to −23° C. under dry argon. EDC (0.31 g, 1.61 mmol) was added, and the reaction was allowed to warm to rt overnight. 5% NaHCO$_3$ was added, and the mixture was extracted with EtOAc. The combined EtOAc extracts were washed with water and brine, dried over MgSO$_4$ and purified by flash silica gel chromatography (1:1) ethyl acetate:hexane) to give 230 mg (50%): $[\alpha^{25}_D$—24.1° (c 1.02, CHCl$_3$); $^1$H NMR (300 MHz, CDCl$_3$) δ0.86 (t, 3H, J=7 Hz), 0.89 (m, 1H), 1.11 (m, 1H), 1.28 (m, 5H), 1.53 (m, 1H), 1.85 (m, 2H), 2.95, (d, 2H, J=7 Hz), 3.25 (m, 1H), 3.36 (s, 3H), 3.48 (m, 1H), 3.68 (m, 3H), 3.93 (m, 1H), 4.31 (m, 2H), 4.66 (s, 2H), 6.07 (dd, 1H, J=10 Hz), 6.29 (m, 1H), 7.21 (m, 6H); mass spectrum (FAB) 430 (M+H).

EXAMPLE 92B

N-4-Methoxymethoxypiperidine Amide of (2S,4S) 2-Benzyl-4-carboxy-3-oxaoctanoic acid The compound prepared from example 92A (326.7 mg, 0.761 mmol) was dissolved in 5 mL glacial HOAc with 2.5 mL EtOAc and cooled in an ice bath as ozone was bubbled into the solution. After 30 m, 1 mL of water was added, and the mixture was allowed to stir at rt overnight. The reaction was evaporated to dryness, partitioned between ether and 5% NaHCO$_3$, and extracted with 5% NaHCO$_3$. The combined aqueous extracts were carefully acidified to pH 3 with 1M HCl and extracted with EtOAc. The EtOAc extracts were combined, dried over MgSO$_4$, and evaporated to give crude product which was dissolved in a minimum amount of EtOAc and triturated with CHCl$_3$ to remove most of the polar impurities to give 125.5 mg (40%): $[\alpha]^{25}_D$—17.1° (c 1.13, CHCl$_3$); $^1$H NMR (300 MHz, CDCl$_3$) δ0.85 (m, 1H), 0.89 (t, 3H, J=7 Hz), 1.32 (m, 6H), 1.61 (m, 1H), 1.79 (m, 2H), 3.06 (m, 2H), 3.25 (m, 1H), 3.38 (s, 3H), 3.47 (m, 1H), 3.58 (m, 1H), 3.74 (m, 1H), 3.86 (m, 1H), 3.98 (m, 1H), 4.57 (m, 1H), 4.68 (s, 2H), 7.29 (m, 5H); mas spectrum (FAB) 408 (M+H).

EXAMPLE 93

(3S,5S) 3,5-Dibenzyl-4-(tert-butoxycarbonyl)-2H-1,4-oxazin 2-one

To a solution of 17 ml (1M, 17 mmol) of sodium bis (hexamethylsilyl) amide in THF cooled to −70° C. (limited liquid nitrogen-diethyl ether bath) was added 5 g (17 mmol) of 4-(tert-butyloxycarbonyl)-5S-(benzyl)-2H-1,4-oxazin-2-one (PCT Patent Application No. WO90/03971, published Apr. 19, 1990) in 20 ml THF. After addition was complete 5.97 ml of dry HMPA was added. The reaction was stirred for 15 m between −70° and −80° C. and 5.1 ml of benzyl bromide was added. The reaction was stirred at −80° to −90° C. for a 40 m period. A dilute solution of sodium bisulfate was added and the reaction warmed to rt, poured into chloroform and the aqueous layer separated. The aqueous layer was extracted once with chloroform. The combined chloroform extracts were washed once with water,dried (MgSO$_4$), and evaporated to give 10.9 g of an oil. The pure lactone was obtained by silica gel chromatography using ethyl acetate:hexane as eluent: 3.9 g (60% yield) of a white solid. mp 149°-150° C.; $[\alpha]^{25}D = +105.07$° (c 1.28, CHCl$_3$); mass spectrum (FAB) 399 (M+NH$_4$).

Anal. Calcd for C$_{23}$H$_{27}$NO$_4$: C, 72.42; H, 7.13; N, 3.67. Found: C, 72.76; H, 7.25; N, 3.67.

EXAMPLE 94

(3R,5R) 3,5-Dibenzyl-4-(tert-butoxycarbonyl)-2H-1,4-oxazin 2-one

To a solution of 53 ml (1M, 53.1 mmol) of sodium bis(hexamethylsilyl) amide in THF cooled to −70° C. (limited liquid nitrogen-diethyl ether bath) was added 15.8 g (54.2 mmol) of 4-(tert-butyloxycarbonyl)-5R-(benzyl)-2H-1,4-oxazin-2-one (prepared using the procedure disclosed in PCT Patent Application No. WO90/03971, published Apr. 19, 1990, example 153 and replacing L-phenylalaninol with D-phenylalaninol) in 63 ml THF. After addition was complete 18.6 ml of dry HMPA was added. The reaction was stirred for 5 min between −70° and −80° C. and 16 ml of benzyl bromide was added. The reaction was stirred at −80° to −90° C. for a 40 m period. A dilute solution of sodium bisulfate was added and the reaction warmed to rt temperature, poured into chloroform and the aqueous layer separated. The aqueous layer was extracted once with chloroform. The combined chloroform extracts were washed once with water, (dried with MgSO$_4$), and evaporated to give 23 g of a crude oil. The pure lactone was obtained by silica gel chromatography using ethyl acetate:hexane as eluent: 12 g (58%) as white solid: mp 149°-150° C.; $[\alpha]^{25}_D = -107.9$° (c 1.28, CHCl3); IR (CHCl$_3$) 1743, 1690 cm$^{-1}$; $^1$H NMR (DMSO-d$_6$, 55° C.) δ7.31 (m, 4H), 7.24 (m, 2H), 7.15 (m, 4H), 4.54 (dd, 1H, J=2, 3.5 Hz), 3.88 (d, 1H, J=6 Hz), 2.89 (dd, 1H, 2, 7.5 Hz), 2.68 (dd, 1H, J=6, 9 Hz), 1.46 (s, 9H); mass spectrum (FAB) 382 (M+H).

Anal. Calcd for C$_{23}$H$_{27}$NO$_4$: C, 72.42; H, 7.13; N, 3.67. Found: C, 72,21; H, 7.16; N, 3.65.

EXAMPLE 95

(2S,4S)
3-[(tert-Butoxycarbonyl)aza]-2,4-dibenzyl-1,5-pentanediol

A solution of 0.8 g (2.1 mmol) of the product of Example 93 in 5 mL of THF and 4.1 mL (1M, 4.1 mmol) of diborane were stirred in an ice-water bath for 18 h. Methanol was added followed by aq. sodium bisulfate. The product was extracted with ethyl acetate, dried (MgSO$_4$), and evaporated. The crude residue was purified by flash chromatography using (1:2) ethyl acetate:-hexane to afforded 722 mg (89%) of product. $[\alpha]^{25}_D = -86.03$ (c 0.63 CHCl$_3$); IR (CDCl$_3$) 3120–3720 (OH), 1700 (carbamate C=O) cm$^{-1}$; $^1$H NMR (DMSO-d6) 7.33–7.09 (m, 10H, C$_6$H$_5$), 1.44 (s, 9H, t-butyl); mass spectrum (FAB) 385 (M+H).

Anal. Calcd for C$_{23}$H$_{31}$NO$_4$: C, 71.68; H, 8.05; N, 3.63. Found: C, 71.25; H, 8.07; N, 3.61.

EXAMPLE 96

(2R,4R)
3-[(tert-Butoxycarbonyl)aza]-2,4-dibenzyl-1,5-pentanediol

Using the procedure in example 95 and replacing the product of Example 93 with the product of Example 94 gave the title compound.

EXAMPLE 97

(2R,4R)-3-Aza-2,4-dibenzyl-1,5-pentanediol.Boron Complex

A solution of 0.846 g of (2R, 4R) N-Boc amino diol from example 96 was stirred with 10 mL of 4M HCl dioxane at room temperature for 1 h. The solvents were evaporated to give a white solid. Aqueous sodium bicarbonate was added and the amine was extracted with chloroform. The chloroform extracts were dried (MgSO$_4$), filtered, and concentrated to give a clear oil. Triethylborate (0.37 mL, 1 equiv.) was added to the oil and the homogenous solution solidified. The solid was heated at 100° C. for 2 h under high vacuum to remove excess ethanol to give the boron complex 13. mp 95°–100° C.; $^{11}$B NMR (CH$_2$Cl$_2$, BF$_3$ Et2O internal standard) 10.5; mass spectrum (FAB) 311 (M+NH$_4$), 286 (M+H, amino diol).

EXAMPLE 98

(5R)
4-(tert-Butoxycarbonyl)-5-phenyl-2H-1,4-oxazin-2-one

The title compound was prepared using the procedure disclosed in PCT Patent Application No. WO90/03971, published Apr. 19, 1990, example 153 and replacing L-phenylalaninol with D-phenylglycinol to give the desired product (see J. Dellaria et al. *Tetrahedron Letters* 1988, 29, 6079–82).

EXAMPLE 99

(2R) 3-Aza-2,5,5-triphenyl-1,5-pentanediol.Boron Complex

A solution of 2.7 g of the product of Example 98 was stirred with 10 mL of 4M HCl in dioxane. Solvents were removed under reduced pressure to give the amine salt. The crude salt was suspended in THF, cooled in an ice-water bath and 5 equiv. (45 mL) of 1M phenylmagnesium bromide was added and the reaction mixture stirred for 24 h at room temperature. The crude product was purified by flash chromatography using (1:1) ethyl acetate:hexane then (2-5:98-95) methanol:ethyl acetate to give the amino diol. Recrystallization of the amino diol from toluene:hexane gave a white crystalline solid, 500 mg. mp 117°–19° C.; $[\alpha]^{25}_D = -28.5°$ (c 0.91, CHCl$_3$); IR (CDCl$_3$) 3720–3200 (OH) cm$^{-1}$; $^1$H NMR (CDCl$_3$) $\delta$7.47–7.19 (m, 15H), 3.82 (dd, J=4,7 Hz, 1H), 3.70 (dd, J=4, 12 Hz, 1H), 3.55 (dd, J=7, 12 Hz, 1H), 3.27 (d, J=12 Hz, 1H), 3.18 (dd, J=12 Hz, 1H), 1.70–1.48 (br s, 1H); mass spectrum (FAB) 334 (M+H).

Anal. Calcd for C$_{22}$H$_{23}$NO$_3$: C, 79.27; H, 6.90; N, 4.20. Found: C, 79.27; H, 6.84; N, 4.14.

Using the procedure in example 97, and 109 mg of (2R) 3-aza-2,5,5-triphenyl-1,5-pentanediol that was prepared above and 0.055 mL (1 equiv.) of triethylborate in 2 mL of THF gave the boron complex. mp 125°–32° C.; mass spectrum (FAB) 334 (M+H for amino diol), 342 (M+H), 359 (M+NH$_4$).

EXAMPLE 100

Alternative Preparation of (S)-1-(2-Furyl)-1-pentanol

Using the procedure in example 83B, and replacing (3aR)-1,3,3-triphenyl pyrrolidino [1,2-c] [1,3,2] oxazaborole with the boron catalyst from example 98 gives the product.

EXAMPLE 101

Alternative Preparation of (S)-1-(2-Furyl)-1-pentanol

Using the procedure in example 83B, and replacing (3aR)-1,3,3-triphenyl pyrrolidino [1,2-c] [1,3,2] oxazaborole with the boron catalyst from example 99 gives the product.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters include a hydroxyl-substituted compound of formula (I) which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the present invention and serve to increase the solubility of these substances in the gastrointestinal tract. The prodrugs are metabolically converted in vivo to the parent compound of formula (I). The preparation of the prodrug esters is carried out by reacting a hydroxyl-substituted compound of formula (I) with an activated amino acyl, phosphoryl or hemisuccinyl derivative. The resulting product is then deprotected to provide the desired prodrug ester.

The novel compounds of the present invention possesses an excellent degree of activity and specificity in treating hypertension in a human or other mammal. The novel compounds of the present invention are also useful for treating congestive heart failure in a human or other mammal. The present invention also relates to the use of the novel compounds of the invention for treating vascular abnormalities in a human or other mammal, especially those vascular diseases associated with diabetes, such as diabetic nephropathy, diabetic neuropathy and diabetic retinopathy. The compounds of the invention are also useful for the treatment of renal diseases in a human or other mammal, in particular acute and chronic renal failure. The compounds of the invention are also useful for the treatment of psoriasis in a human or other mammal.

The ability of the compounds of the invention to inhibit human renal renin can be demonstrated in vitro by reacting a selected compound at varied concentrations with human renal renin, free from acid proteolytic activity, and with renin substrate (human angiotensinogen) at 37 degrees C. and pH of 6.0. At the end of the incubation, the amount of angiotensin I formed is measured by radioimmunoassay and the molar concentration required to cause 50% inhibition, expressed as the $IC_{50}$ is calculated. When tested in accordance with the foregoing procedure, the compounds of the invention demonstrated $IC_{50}$'s in the range of $10^{-9}M$ as seen in Table 1.

TABLE 1

| Example | $IC_{50}$ (nM) |
| --- | --- |
| 2c | 2.1 |
| 3 | 1.3 |
| 4 | 1.0 |
| 5b | 2.9 |
| 6c | 1.8 |
| 7b | 0.78 |
| 10 | 3.0 |
| 11 | 2.4 |
| 12b | 2.6 |
| 16 | 1.8 |
| 17 | 1.5 |
| 19c | 1.6 |
| 20 | 1.3 |
| 21 | 1.3 |
| 22c | 3.4 |
| 23 | 1.1 |
| 24 | 1.0 |
| 25 | 1.0 |
| 27 | 0.8 |
| 29b | 1.2 |
| 30 | 2.3 |
| 31 | 2.0 |
| 32 | 0.9 |
| 33 | 1.0 |
| 34 | 1.1 |
| 36 | 1.3 |

TABLE 1-continued

| Example | $IC_{50}$ (nM) |
| --- | --- |
| 37b | 1.7 |
| 37c | 1.4 |
| 42f | 11 |
| 43b | 33 |
| 44c | 5 |
| 45 | 23 |
| 46b | 27 |
| 47e | 1.7 |
| 48c | 3.6 |
| 49b | 2.8 |
| 51b | 1.0 |
| 52b | 1.4 |
| 53b | 1.2 |
| 55b | 2.4 |
| 56b | 1.1 |
| 57b | 0.94 |
| 62b | 2.4 |
| 73b | 1.2 |
| 77d | 5.2 |

Total daily dose of a compound of the invention administered to a human or other mammal in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection,, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present invention also relates to the use of novel compounds, pharmaceutical compositions containing the novel compounds and the use of the compounds and compositions to inhibit renin for treating glaucoma or reducing and/or controlling intraocular pressure. The present invention also relates to the use of novel compounds and pharmaceutical compositions which inhibit renin in combination with a beta-adrenergic antagonist agent or an angiotensin converting enzyme inhibiting compound for treating glaucoma or reducing and/or controlling intraocular pressure.

The present invention also relates to pharmaceutical compositions for treating the increase in intraocular pressure associated with the administration of steroidal antiinflammatory agents comprising novel renin inhibiting compounds in combination with a steroidal antiinflammatory compound in a pharmaceutically acceptable vehicle.

The present invention also relates to a kit comprising in individual containers in a single package a novel renin inhibiting compound in a suitable pharmaceutical vehicle and a steroidal antiinflammatory compound in a suitable pharmaceutical vehicle and/or a beta-adrenergic antagonist agent in a suitable pharmaceutical vehicle or an angiotensin converting enzyme inhibiting compound in a suitable pharmaceutical vehicle.

The compositions of the invention are administered as topical or systemic pharmaceutical compositions when used for treating or reducing and/or controlling intraocular pressure.

These compositions are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments and solid inserts.

Examples of suitable pharmaceutically acceptable vehicles for ophthalmic administration are water, propylene glycol and other pharmaceutically acceptable alcohols, sesame or peanut oil and other pharmaceutically acceptable vegetable oils, petroleum jelly, water soluble ophthalmologically acceptable non-toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xantham gum; and mixtures of these polymers. Such compositions may also contain adjuvants such as buffering, preserving, wetting, emulsifying, and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from 0.00001 to 1.0 (w/v) percent concentration. More preferably the active compound will be administered as an isotonic aqueous solution of from 0.00001 to 0.1 (w/v) percent concentration.

The term "controlling intraocular pressure" as used herein means the regulation, attenuation and modulation of increased intraocular tension. The term also means that the decrease, in the otherwise elevated intraocular pressure, obtained by the methods and compositions of the invention is maintained for a significant period of time as, for example, between consecutive doses of the composition of the invention.

The novel renin inhibiting compounds of the invention may be the only active ingredient for controlling intraocular pressure in the methods and compositions of the invention or may be used in combination with other ingredients which control intraocular pressure such as beta-adrenergic antagonist compounds.

The term "beta-adrenergic antagonist" as used herein means a compound which by binding to beta-adrenergic plasma membrane receptors reduces or eliminates sympathetic activity or blocks the effects of exogenously administered catecholamines or adrenergic drugs. Examples of beta-adrenergic antagonists are atenolol, metopropol, nadolol, propranolol, timolol, labetalol, betaxolol, carteolol and dilevalol and pharmaceutically acceptable salts thereof. Most preferably the beta-adrenergic antagonist is timolol.

Timolol is currently used for treating glaucoma or reducing and/or controlling intraocular pressure, but it has a number of adverse side effects. Accordingly, administration of a composition comprising a combination of a beta-adrenergic antagonist and a novel renin inhibiting compound of the invention could produce a reduction in intraocular pressure equivalent to that produced by a beta-adrenergic antagonist alone, but at a reduced dose level of the beta-adrenergic antagonist. This will result in a reduced level of the beta-adrenergic antagonist related adverse side effects.

The combination composition is administered as a single dosage form containing both the novel renin inhibitor and the beta-adrenergic antagonist. The beta adrenergic antagonist may comprise from 5 mg to about 125 mg of the composition of the invention. The preferred ranges of the components in the composition of the invention in unit dosage form are:

Renin inhibitor: 1 ng to 0.1 mg
Beta-adrenergic antagonist: 5 ug to 125 ug

When the beta-adrenergic antagonist and the novel renin inhibitor are administered as separate compositions the present invention relates to a kit comprising in two separate containers a pharmaceutically acceptable beta-adrenergic antagonist composition and a pharmaceutically acceptable novel renin inhibitor composition, in a single package. A preferred kit comprises a beta-adrenergic antagonist composition and a topical novel renin inhibitor composition. A most preferred kit comprises a topical ophthalmological beta-adrenergic antagonist composition and a topical ophthalmological novel renin inhibitor composition.

The novel renin inhibiting compounds of the invention may also be administered in combination with an angiotensin converting enzyme (ACE) inhibiting compound. Examples of angiotensin converting enzyme inhibiting compounds are captopril and enalapril. As was previously mentioned, ACE inhibitors have some undesirable side effects. Accordingly, administration of an ACE inhibitor in combination with a renin inhibitor could produce a reduction in intraocular pressure greater than or equivalent to that of an ACE inhibitor alone, but at a reduced dose level of the ACE inhibitor. This will result in a reduced level of the ACE inhibitor related adverse side effects.

The combination composition is administered as a single dose form containing both the novel renin inhibitor and the angiotensin converting enzyme inhibitor. The ACE inhibitor may comprise from 5 ng to about 50 ug of the composition of the invention. The preferred ranges of the components in the composition of the invention in unit dosage form are:

Renin inhibitor: 1 ng to 0.1 mg
ACE inhibitor: 5 ng to 50 ug

When the ACE inhibitor and the novel renin inhibitor are administered as separate compositions the present invention relates to a kit comprising in two separate containers a pharmaceutically acceptable ACE inhibitor composition and a pharmaceutically acceptable novel renin inhibitor composition, in a single package. A preferred kit comprises an ACE inhibitor composition and a topical novel renin inhibitor composition. A most preferred kit comprises a topical ophthalmological ACE inhibitor composition and a topical novel renin inhibitor composition.

Dosage levels of the active compounds in the compositions of the invention may be varied so as to obtain a desired therapeutic response depending on the route of administration, severity of the disease and the response of the patient.

Topical, ophthalmic and systemic administration of steroidal antiinflammatory agents can cause an increase in intraocular pressure. The increase in intraocular pressure can be reduced by the administration of a novel renin inhibiting compound of the invention. Steroidal antiinflammatory agents include hydrocortisone, cortisone, prednisone, prednisolone, dexamethasone, methylprednisolone, triamcinolone, betamethasone, alclometasone, flunisolide, beclomethasone, clorocortolone, diflorasone, halcinonide, fluocinonide, fluocinolone, desoximetasone, medrysone, paramethasone, and fluorometholone, and their pharmaceutically acceptable salts and esters. Preferred steroidal antiinflammatory agents are hydrocortisone, prednisolone, dexamethasone, medrysone and fluorometholone and their pharmaceutically acceptable salts and esters. The novel renin inhibitor is administered after use of a steroidal antiinflammatory agent or at the same time, causing reduction and/or control of intraocular pressure.

Various combinations of a topical or oral or injectible dosage form of a steroidal antiinflammatory agent and a topical or oral dosage form of the novel renin inhibitor may be used. A preferred combination comprises a topical steroidal antiinflammatory and a topical novel renin inhibitor. More preferred is a topical ophthalmic dosage form comprising both a steroidal antiinflammatory and a novel renin inhibitor.

When the steroidal antiinflammatory agent and the novel renin inhibitor are administered as separate compositions the present invention relates to a kit comprising in two separate containers a pharmaceutically acceptable steroidal antiinflammatory agent composition and a pharmaceutically acceptable novel renin inhibitor composition, in a single package. A preferred kit comprises a steroidal antiinflammatory composition and a topical novel renin inhibitor composition. A most preferred kit comprises a topical ophthamological steroidal antiinflammatory composition and a topical ophthamological novel renin inhibitor composition.

The combination composition of the invention may contain from about 0.00001 to 1.0 (w/v) percent of the novel renin inhibitor for combined or separate topical administration. More preferably the amount of the novel renin inhibitor is about 0.00001 to 0.1 (w/v) percent of the composition. The amount of the novel renin inhibitor in a unit dosage form for topical administration to the eye is from about 5 ng to about 0.5 mg, preferably from about 5 ng to about 25 ng. The dose required will depend on the potency of the particular novel renin inhibitor, the severity of the intraocular pressure increase and the response of the individual patient.

The combination composition of the invention may contain from about 0.05 to 1.5 (w/v) percent of the steroidal antiinflammatory for combined or separate topical administration. The amount of the steroidal antiinflammatory in a unit dosage form for topical administration to the eye is from about 20 ug to about 600 ug. The dose required will depend on the potency of the particular steroidal antiinflammatory, the severity of the disease and the response of the individual patient.

When the steroidal antiinflammatory agent of the combination therapeutic method of the invention is administered other than ophthalmically, appropriate doses are well known in the art.

The compositions of the invention may include other therapeutic agents in addition to the novel renin inhibitor, and other agents which reduce and/or control intraocular pressure.

The effect on intraocular pressure of the novel compounds of the invention can be determined in rabbits by using the following method.

Effects of Topically Administered Renin Inhibiting Compounds on Intraocular Pressure of Rabbits a. Method The antiglaucoma activity of the compounds was tested by measuring the effect on intraocular pressure in rabbits as described by Tinjum, A. M., Acta Ophthalmologica, 50, 677 (1972). Male albino, New Zealand rabbits were placed in restraining devices and the intraocular pressure was measured with an applamatic tonometer. Exactly 0.1 ml of an isotonic saline solution containing a test compound was instilled into the conjuctival sac and the intraocular pressure was measured at 5, 15, 30, 60, 90, 120 and 180 minutes afterwards.

The ability of a compound of the invention to treat vascular diseases, especially those associated with diabetes, can be demonstrated by comparing urinary protein excretion in control diabetic Wistar rats with urinary protein excretion in diabetic Wistar rats treated with a compound of the invention. Wistar rats are made diabetic by streptozocin treatment.

The present invention is also directed to the use of a compound of the formula I in combination with one or more cardiovascular agents independently selected from diuretics, adrenergic blocking agents, vasodilators, calcium channel blockers, angiotensin converting enzyme (ACE) inhibitors, potassium channel activators, antiserotoninergic agents, thromboxane synthetase inhibitors, angiotensin II (AII) antagonists and other agents useful for treating (in a human or other mammal) hypertension, congestive heart failure, vascular diseases related to diabetes or for treating renal diseases such as acute or chronic renal failure.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside, flosequinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Representative antiserotoninergic agents include ketanserin and the like or a pharmaceutically acceptable salt thereof.

Representative angiotensin II antagonists include DUP527 and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compound of formula I and the antihypertensive agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

In addition, the present invention is directed to the use of a compound of formula I to inhibit Candida acid protease in mammals, especially humans. The compounds of the present invention are also useful for preventing or treating infections caused by Candida species in mammals, especially humans. The present invention also relates to the use of the compounds of the invention in combination with one or more other antifungal agents. Other antifungal agents are selected from the group consisting of amphotericin B, nystatin, flucytosine, ketoconazole, miconazole, clotrimazole, fluconazole and itraconazole.

The ability of the compounds of the invention to inhibit Candida acid protease can be demonstrated in vitro by the following method.

Isolation and Purification of *Candida albicans* Acid Protease

Organism and growth conditions.

*Candida albicans* $ATCC_{10231}$ was grown overnight in Sabouraud broth (Difco) at 30° C. Cells were centrifuged at 10,000×g for 10 min (4° C.) and the cell pellet washed once with 10 mM phosphate buffered saline (PBS), pH7.0. Washed cells ($6 \times 10^6$ colony forming units per mL) were grown in yeast nitrogen base without ammonium sulfate or amino acids (Difco), plus 2% glucose and 0.1% casein (nitrogen source) at 37° C.

Proteinase isolation.

Maximum proteinase production was attained when the culture reached a pH of 3.5 to 4.0 (about 48 hrs). Cells were then harvested at 10,000×g for 20 min (4° C.) and the supernatant filtered through a 0.2μ acetate filter unit (Nalgen). The filtrate was concentrated on an Amicon concentrator (PM30 or YM10 membrane, 75 mm) and 30 mL of the concentrate was loaded onto a Cibacron blue F3GA-6% agarose (Pierce Chem.) column (1.5×44 cm) equilibrated with 10 mM sodium citrate, pH 6.5, containing 1 mM EDTA and 0.02% sodium azide (Ray, T. L., and Payne, C. D. Infection and Immunity 58: 508–514, 1990). Bovine serum albumin (BSA) was used as substrate to monitor the column for proteinase activity and to determine total proteolytic units. One BSA proteolytic unit was defined as an optical density (750 nm wavelength) increase of 0.100 under incubation conditions of 37° C. for 60 min (Remold, H., Fasold, H., and Staib, F. Biochimica et Biophysica Acta 167:399–406, 1968). Fractions with proteolytic activity were eluted in the void volume with equilibration buffer, pooled and stored at −70° C. Proteinase purity and molecular weight was determined by the Phast-gel (12.5% acrylamide) electrophoresis system (Pharmacia). Protein was determined by the Lowry method (Lowry, O. H., Rosenbrough, N. J., Farr, A. L., and Randall, R. J. Journal of Biological Chemistry 193:263–275, 1951). A fluorogenic substrate, A78331, may also be used to monitor proteinase production and purification. This substrate, DABCYL-Gaba-Ile-His-Pro-Phe-His-Leu-Val-Ile-His-Thr-EDANS (Holzman, T. F., Chung, C. C., Edalji, R., Egan, D. A., Gubbins, E. J., Rueter, A., Howard, G., Yang, L. K., Pederson, T. M., Krafft, G. A., and Wang, G. T. Journal of Protein Chemistry 9:663–672, 1990) contains the fluorescent EDANS group, [5-(2-aminoethyl)-amino]naphthalene-1-sulfonic acid, which is quenched by the DABCYL group, 4-(4-dimethyl-aminophenylazo)benzoic acid, as long as it is part of the molecule (Matayoshi, E. D., Wang, G. T., Krafft, G. A., and Erickson, J. Science 247:954–958, 1990). Proteolysis of this compound by the fungal proteinase releases Thr-EDANS, which when activated at 340 nm fluoresces at 490 nm with the same intensity as equimolar EDANS. Activity is expressed in terms of nmol EDANS released from 32 μM A78331 under incubation conditions of 22° C. for 60 min. One BSA proteolytic unit was equivalent to 1.03 nmol EDANS released.

In Vitro Inhibitor Assay Method.
Microtiter assay.

The assay for inhibitors of *C. albicans* acid proteinase is done in microtiter trays with the fluorogenic substrate A78331. Test compounds are initially tested at 1 μM, followed by a dose study ranging down to 0.2 nM for compounds having greater then 80% inhibition from control at the 1 μM dose. The reaction mixture consists of 5 μL test compound or dimethyl sulfoxide and 45 μL of fungal proteinase (0.13 BSA proteolytic units or 0.13 nmol EDANS released) in 50 mM sodium citrate, pH 4.5, which is preincubated at 22° C. for 30 min. The reaction is started with the addition of 50 μL fluorogenic substrate in citrate buffer and the incubation is continued at 22° C. for 90 min. The reaction is terminated with 150 μL pepstatin (final concentration of 1 μM) and 210 μL samples are transfered to microfluor plates for fluorescence quantitation in a luminescence spectrophotometer (Perkin-Elmer model LS-50). The excitation wavelength is 340 nm and the emission is monitored at 490 nm (430 nm filter employed). Inhibition is expressed as % change in relative intensity from the dimethyl sulfoxide control group (no inhibitor). $IC_{50}$'s are determined from plots of log dose versus % inhibition from control.

The ability of a compound of the invention to treat an infection caused by a Candida species can be demonstrated in vitro according to the methods outlined by El-Maghrabi, et al., Clin. Exp. Dermatol. 15 183 (1990); Ghannoum, J. Appl. Bacteriol. 68 163 (1990); and Ray, et al., J. Invest. Dermatol. 83 37 (1984).

The ability of a compound of the invention to treat an infection caused by a Candida species can be demonstrated in vitro according to the methods outlined by Ray, et al., J. Invest. Dermatol. 66 29 (1976); Ray, et al., Infect. Immun. 56 1942 (1988); Van Cutsem, et al., Sabouraudia 9 17 (1971); Sohnie, et al., J. Immunol. 117 523 (1976); Kobayashi, et al., Microb. Immunol. 33 709 (1989); Shimizu, et al., Microb. Immunol. 31 1045 (1987); Zotter, et al., Dermatol. Mon. Schr. 176 189 (1990); and Ruchel, et al., Zbl. Bakt. 273 391 (1990).

The ability of a compound of the invention to prevent an infection caused by a Candida species can be demonstrated according to the methods outlined by Meitner, et al., Infect. Immun. 58 2228 (1990) and Cole, et al., Mycoses 33 7 (1990).

Total daily dose of a compound of the invention administered to a human or other mammal for inhibiting Candida acid protease or treating or preventing an infection caused by a Candida species in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

In addition, the present invention is directed to the use of a compound of formula I to inhibit retroviral proteases and in particular to inhibit HIV-1 protease and HIV-2 protease. Compounds of formula I are useful for treatment or prophylaxis of diseases caused by retroviruses, especially acquired immune deficiency syndrome or an HIV infection.

The inhibitory potency of the compound of the invention against HIV protease can be determined by the following method.

Fluorogenic Assay for Screening Inhibitors of HIV Protease

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1M sodium chloride, 5 mM dithiothreitol, 0.5 mg/ml bovine serum albumin, 1.3 uM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmision 490 nM) is recorded as a function of time. The reaction rate is determined for the first six to eight minutes. The observed rate is directly proportional to the moles of substrate cleaved per unit time. The percent inhibition is 100×(1−(rate in presence of inhibitor)/(rate in absence of inhibitor)).

Fluorogenic substrate: Dabcyl-Ser-Gln-Asp-Tyr-Pro-Ile-Val-Gln-EDANS wherein DABCYL=4-(4-dimethylaminophenyl)azobenzoic acid and EDANS=5-((2-aminoethyl)amino)-naphthalene-1-sulfonic acid.

The antiviral activity of compound of the invention can be demonstrated using the following method.

A mixture of 0.1 ml (4×10⁶ cells/ml) of H9 cells and 0.1 ml (100 infectious units) of HIV-1$_{3B}$ is incubated on a shaker for 2 h. The resulting culture is washed three times, resuspended into 2 ml of medium, and treated with 10 μl of the compound of the invention (5 mM in dimethylsulfoxide). The control culture is treated in an identical manner except the last step was omitted. After incubation of the culture for eight days without change of medium, an aliquot (0.1 ml) of the supernatent is withdrawn and incubated with fresh H9 cells on a shaker for 2 h. The resulting culture is washed three times, resuspended into 2 ml of medium, and incubated. Virus infectivity is determined using the Abbott HTLV-III antigen E.I.A. method (Paul, et al., J. Med. Virol., 22 357 (1987)).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound of the formula:

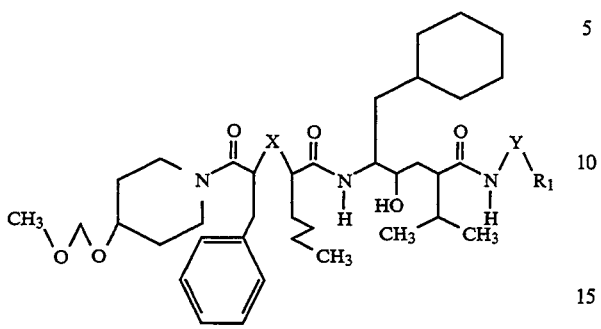

wherein X is O Y is $C_1$ to $C_6$ alkylene which is unsubstituted or substituted with one or two substituents independently selected from $C_1$ to $C_7$ loweralkyl, $C_1$ to $C_7$ alkoxy and $C_1$ to $C_7$ thioalkoxy; and $R_1$ is —$NHR_2$ wherein $R_2$ is hydrogen, $C_1$ to $C_7$ alkanoyl, $C_1$ to $C_7$ hydroxyalkyl, formyl, $C_1$ to $C_7$ alkoxycarbonyl, aroyl wherein aroyl is —$C(O)R_6$ wherein $R_6$ is phenyl, naphthyl, tetrahydronaphthyl, indanyl or indenyl, —C(O)$NHR_{17}$ wherein $R_{17}$ is hydrogen or $C_1$ to $C_7$ loweralkyl, —C(S)$NHR_{18}$ wherein $R_{18}$ is hydrogen or $C_1$ to $C_7$ loweralkyl, —C(=N—CN)—$NHR_{19}$ wherein $R_{19}$ is hydrogen or $C_1$ to $C_7$ loweralkyl, —C(=N—CN)—$SR_{22}$ wherein $R_{22}$ is $C_1$ to $C_7$ loweralkyl,

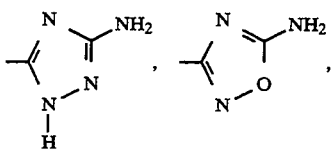

—C(O)O-benzyl, —$SO_2NR_{26a}R_{26b}$ wherein $R_{26a}$ and $R_{26b}$ are independently selected from $C_1$ to $C_7$ loweralkyl or —$SO_2R_{27}$ wherein $R_{27}$ is $C_1$ to $C_7$ loweralkyl; or a pharmaceutically acceptable salt or prodrug ester thereof.

2. The compound of claim 1 wherein X is O and $R_1$ is —$NHR_2$ wherein $R_2$ is hydrogen, $C_1$ to $C_7$ hydroxyalkyl, —C(O)$NHR_{17}$ wherein $R_{17}$ is hydrogen or $C_1$ to $C_7$ loweralkyl, —C(S)$NHR_{18}$ wherein $R_{18}$ is hydrogen or $C_1$ to $C_7$ loweralkyl, —C(=N—CN)—$NHR_{19}$ wherein $R_{19}$ is hydrogen or $C_1$ to $C_7$ loweralkyl, —C(=N—CN)—$SR_{22}$ wherein $R_{22}$ is $C_1$ to $C_7$ loweralkyl,

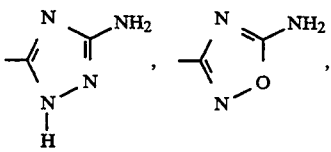

—C(O)O-benzyl, —$SO_2NR_{26a}R_{26b}$ wherein $R_{26a}$ and $R_{26b}$ are independently selected from $C_1$ to $C_7$ loweralkyl or —$SO_2R_{27}$ wherein $R_{27}$ is $C_1$ to $C_7$ loweralkyl.

3. A compound selected from the group consisting of:
N-(3-(2-Hydroxyethyl)amino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(3-(Aminocarbonylamino)propyl) 5(S)-2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(3-(Aminothionylamino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-amino-2-methylpropyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-Aminoethyl) 5(S)-(2(S)-(4-(methoxymethoxy)piperidin-1-yl)carbonyl-2-phenyl)ethoxyhexanamido)-6-cyclohexyl-4(S)-hydroxy-2-(S)-isopropylhexanamide;

N-(4-Aminobutyl) 5(S)-(2(S)-(4-(methoxymethoxy)piperidin-1-yl)carbonyl-2-phenyl)ethoxyhexanamido)-6-cyclohexyl-4(S)-hydroxy-2-(S)-isopropylhexanamide;

N-(5-Aminopentyl) 5(S)-(2(S)-(4-(methoxymethoxy)piperidin-1-yl)carbonyl-2-phenyl)ethoxyhexanamido)-6-cyclohexyl-4(S)-hydroxy-2-(S)-isopropylhexanamide;

N-(3-Amino-3-methylbutyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-Ureido)ethyl 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-(Thioureido)ethyl 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-Acetamidoethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-(S-Methyl-N'-cyanoisothioureido)ethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-(N'-cyanoureido)ethyl) 5(S)-(2(S)-(1(S)-(4-(methoxymethoxy)piperidin-1yl)carbonyl-2-phenyl)ethoxyhexanamido)-6-cyclohexyl-4(S)-hydroxy-2(S)-isopropylhexanamide;

N-(2-(N-Methyl-N'-cyanoureido)ethyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(2-((3-Amino-1H-1,2,4-triazol-5-yl)amino)ethyl) 2(S)-((3-(tert-butyloxycarbonyl)-2,2-dimethyl-4(S)-cyclohexylmethyl-5(S)-oxazolidinyl)methyl)-3-methylbutanamide;

N-(2-((5-Amino-1,2,4-oxadiazol-5-yl)amino)ethyl) 2(S)-((3-(tert-butyloxycarbonyl)-2,2-dimethyl-4(S)-cyclohexylmethyl-5(S)-oxazolidinyl)methyl)-3methylbutanamide;

N-(3-(S-Methyl-N'-cyanoisothioureido)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(3-(N-Methyl-N'-cyanoureido)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(3-(N'-cyanoureido)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide;

N-(3-((3-Amino-1H-1,2,4-triazol-5-yl)amino)propyl) 5(S)-(2(S)-(1(S)-(4-(methoxymethoxy)piperidin-1-yl)carbonyl-2-phenyl)ethoxyhexanamido)-6-cyclohexyl-4(S)-hydroxy-2(S)-isopropylhexanamide; and N-(3-((5-Amino-1,2,4-oxadiazol-5-yl)amino)propyl) 2(S)-((3-(tert-butyloxycarbonyl)-2,2-dimethyl-4(S)-cyclohexylmethyl-5(S)-oxazolidinyl)methyl)-3-methylbutanamide;

or a pharmaceutically acceptable salt or prodrug ester thereof.

4. A method for treating hypertension or treating congestive heart failure comprising administering to a mammal in need of such treatment a therapeutically effective amount of a compound of claim 1.

5. A pharmaceutical composition for treating hypertension or congestive heart failure, comprising a pharmaceutical carrier and a therapeutically effective amount of a compound of claim 1.

6. A method for inhibiting renin comprising administering to a mammal in need of such treatment a therapeutically effective amount of a compound of claim 1.

* * * * *